US007838658B2

(12) United States Patent
MacLachlan et al.

(10) Patent No.: US 7,838,658 B2
(45) Date of Patent: Nov. 23, 2010

(54) SIRNA SILENCING OF FILOVIRUS GENE EXPRESSION

(76) Inventors: Ian MacLachlan, 1544 Grant Street, Vancouver, BC (CA) V5L 2Y2; Vandana Sood, 955 Thurlow Street, Suite 303, Vancouver, BC (CA) V6E 1W5; Thomas W. Geisbert, 162 Quinn Lea Rd., Harpers Ferry, WV (US) 25425-5375; Lisa E. Hensley, 200 W. College Ter., Frederick, MD (US) 21701; Elliott Kagan, 4 Royal Oak Ct., Potomac, MD (US) 20854-2654

( * ) Notice: Subject to any disclaimer, the term of this patent is extended or adjusted under 35 U.S.C. 154(b) by 410 days.

(21) Appl. No.: 11/584,341

(22) Filed: Oct. 20, 2006

(65) Prior Publication Data

US 2007/0135370 A1 Jun. 14, 2007

Related U.S. Application Data

(60) Provisional application No. 60/729,476, filed on Oct. 20, 2005.

(51) Int. Cl.
*C07H 21/04* (2006.01)
*A61K 48/00* (2006.01)

(52) U.S. Cl. .................. 536/24.5; 536/24.31; 536/24.1; 435/6; 435/325; 435/375; 514/44

(58) Field of Classification Search ........................ None
See application file for complete search history.

(56) References Cited

U.S. PATENT DOCUMENTS

| 5,705,385 | A | 1/1998 | Bally et al. |
| 5,976,567 | A | 11/1999 | Wheeler et al. |
| 5,981,501 | A | 11/1999 | Wheeler et al. |
| 6,534,484 | B1 | 3/2003 | Wheeler et al. |
| 6,586,410 | B1 | 7/2003 | Wheeler et al. |
| 6,680,068 | B2 * | 1/2004 | Campbell et al. ............ 424/450 |
| 6,815,432 | B2 | 11/2004 | Wheeler et al. |
| 6,858,224 | B2 | 2/2005 | Wheeler et al. |
| 2003/0143732 | A1 * | 7/2003 | Fosnaugh et al. ............ 435/325 |
| 2004/0142892 | A1 | 7/2004 | Finn et al. |
| 2004/0253723 | A1 | 12/2004 | Tachas et al. |
| 2004/0259247 | A1 * | 12/2004 | Tuschl et al. ................ 435/375 |
| 2005/0064595 | A1 | 3/2005 | MacLachlan et al. |
| 2005/0282188 | A1 * | 12/2005 | Haeberli et al. ................ 435/6 |
| 2006/0008910 | A1 | 1/2006 | MacLachlan et al. |
| 2006/0205693 | A1 * | 9/2006 | Stein et al. ..................... 514/81 |
| 2007/0135372 | A1 | 6/2007 | MacLachlan et al. |

FOREIGN PATENT DOCUMENTS

| WO | WO 02/087541 A1 | 11/2002 |
| WO | WO 03/097805 A2 | 11/2003 |
| WO | WO 2004/065546 A2 | 8/2004 |
| WO | WO 2004/110499 A1 | 12/2004 |
| WO | WO 2005/007196 A2 | 1/2005 |
| WO | WO 2005/026372 A1 | 3/2005 |
| WO | WO 2005/120152 A2 | 12/2005 |
| WO | WO 2005/121348 A1 | 12/2005 |
| WO | WO 2006/074546 A1 | 7/2006 |
| WO | WO 2007/051303 A1 | 5/2007 |

OTHER PUBLICATIONS

Arpicco, S., et al., "Preparation and Characterization of Novel Cationic Lipids Developed for Gene Transfection," Proceed. Int'l Symp. Control. Rel. Bioact. Mater. (Controlled Release Society, Inc.), 1999, vol. 26, pp. 759-760.
Arpicco, S., et al., "Synthesis, characterization and transfection activity of new saturated and unsaturated cationic lipids," IL Farmaco, 2004, vol. 59, pp. 869-878.
Beale, G., et al., "Gene Silencing Nucleic Acids Designed by Scanning Arrays: Anti-EGFR Activity of siRNA, Ribozyme and DNA Enzymes Targeting a Single Hybridization-accessible Region using the Same Delivery System," Journal of Drug Targeting, 2003, vol. 11, No. 7, pp. 449-456.
Cevc, G., "How Membrane Chain-Melting Phase-Transition Temperature is Affected by the lipid Chain Asymmetry and Degree of Unsaturation: An Effective Chain-Length Model," Biochemistry, 1991, vol. 30, pp. 7186-7193.
Enterlein, Sven, et al., "VP35 Knockdown Inhibits Ebola Virus Amplification and Protects against Lethal Infection in Mice," Antimicrobial Agents and Chemotherapy, 2006, vol. 50, No. 3, pp. 984-993.
Feldmann, Heinz, et al., "Therapy and prophylaxis of Ebola virus infections," Current Opinion in Investigational Drugs, 2005, vol. 6, No. 8, pp. 823-830.
Fowler, Trent, et al., "Inhibition of Marburg virus protein expression and viral release by RNA interference," Journal of General Virology, 2005, vol. 86, pp. 1181-1188.
Geisbert, Thomas W., et al., "Postexposure Protection of Guinea Pigs against a Lethal Ebola Virus Challenge Is Conferred by RNA Interference," The Journal of Infectious Diseases, 2006, vol. 193, No. 12, pp. 1650-1657.
Jiang, L., et al., "Comparison of protein precipitation methods for sample preparation prior to proteomic analysis," Journal of Chromatography A, 2004, vol. 1023, pp. 317-320.
Keough, K., "Influence of chain unsaturation and chain position on thermotropism and intermolecular interactions in membranes," Biochem. Soc. Transactions, 1990, vol. 18, No. 5, pp. 835-837.
Paul, C., et al., "Effective expression of small interfering RNA in human cells," Nature Biotech., 2002, vol. 20, pp. 505-508.
Spagnou, S., et al., "Lipidic Carriers of siRNA: Differences in the Formulation, Cellular Uptake, and Delivery with Plasmid DNA," Biochemistry, 2004, vol. 43, pp. 13348-13356.

(Continued)

*Primary Examiner*—Kimberly Chong
(74) *Attorney, Agent, or Firm*—Townsend and Townsend and Crew LLP

(57) ABSTRACT

The present invention provides siRNA molecules that target Filovirus gene expression and methods of using such siRNA molecules to silence Filovirus gene expression. The present invention also provides nucleic acid-lipid particles that target Filovirus gene expression comprising an siRNA that silences Filovirus gene expression, a cationic lipid, and a non-cationic lipid.

45 Claims, 10 Drawing Sheets

OTHER PUBLICATIONS

Warfield, Kelly L., et al., "Gene-Specific Countermeasures against Ebola Virus Based on Antisense Phosphorodiamidate Morpholino Oligomers," PLoS Pathogens, 2006, vol. 2, No. 1, pp. 0005-0012.

Reynolds, A., et al., "Rational siRNA design for RNA interference," Nat. Biotech., 2004, vol. 22, No. 3, pp. 326-330.

* cited by examiner

SIRNA SILENCING OF FILOVIRUS GENE EXPRESSION

CROSS-REFERENCES TO RELATED APPLICATIONS

This application claims the benefit of U.S. Provisional Application No. 60/729,476, filed Oct. 20, 2005, the disclosure of which is hereby incorporated by reference in its entirety for all purposes.

REFERENCE TO A "SEQUENCE LISTING," A TABLE, OR A COMPUTER PROGRAM LISTING APPENDIX SUBMITTED ON A COMPACT DISK

The Sequence Listing written in file -56-1.APP, 7,880,704 bytes, machine format IBM-PC, MS-Windows operating system, created on Feb. 5, 2007 on duplicate copies of compact disc of the written form of the Sequence Listing, i.e., "Copy 1 of 3" and "Copy 2 of 3", and the sequence information recorded in computer readable form on compact disc , i.e., "Copy 3 of 3" for application Ser. No: 11/584,341, MacLachlan et al., siRNA SILENCING OF FILOVIRUS GENE EXPRESSION, is hereby incorporated by reference.

BACKGROUND OF THE INVENTION

Filoviruses (e.g., Ebola virus and Marburg virus) are among the most lethal and destructive viruses. They cause severe, often-fatal viral hemorrhagic fevers in humans and nonhuman primates (e.g., monkeys, gorillas, and chimpanzees). Filoviruses are of particular concern as possible biological weapons since they have the potential for aerosol dissemination and weaponization.

The incubation period for Filovirus infection ranges from 2 to 21 days. The onset of illness is abrupt and is characterized by high fever, headaches, joint and muscle aches, sore throat, fatigue, diarrhea, vomiting, and stomach pain. A rash, red eyes, hiccups and internal and external bleeding may be seen in some patients. Within one week of becoming infected with the virus, most patients experience chest pains and multiple organ failure, go into shock, and die. Some patients also experience blindness and extensive bleeding before dying.

Filoviridae are a family of RNA viruses. Two members of the Filoviridae family have been identified: Ebola virus and Marburg virus. There is one identified strain of Marburg virus and four identified subtypes (i.e., strains) of Ebola virus: Ebola-Zaire, Ebola-Sudan, Ebola-Ivory Coast (i.e., Ebola-Tai), and Ebola-Reston. The exact origin, locations, and natural habitat of Filoviridae unknown. However, on the basis of available evidence and the nature of similar viruses, it is postulated that Filoviridae are zoonotic (i.e., animal-borne) and are normally maintained in an animal host that is native to the African continent.

Because the natural reservoir of the virus is unknown, the manner in which the virus first appears in a human at the start of an outbreak has not been determined. It is hypothesized that the first patient becomes infected through contact with an infected animal. After the first case-patient in an outbreak setting is infected, the virus can be transmitted in several ways. People can be exposed to the virus from direct contact with the blood and/or secretions of an infected person. Thus, the virus is often spread through families and friends because they come in close contact with such secretions when caring for infected persons. People can also be exposed to the virus through contact with objects contaminated with infected secretions (e.g., needles or syringes). All Filoviridae species have also displayed the ability to be spread through airborne particles (i.e., via aerosol).

Prevention and treatment for Filovirus infection presents many challenges. Because the identity and location of the natural reservoir of the viruses are unknown, there are few effective preventative measures. There is currently no treatment for Filovirus infection. Patients receive supportive therapy, i.e., electrolyte and fluid balancing, oxygen, blood pressure maintenance, and treatment for any secondary infections.

Thus, there is a need for compositions and methods for treating and preventing filovirus infection, e.g., by specifically modulating filovirus gene expression. The present invention addresses these and other needs.

SUMMARY OF THE INVENTION

The present invention provides siRNA molecules that target Filovirus gene (e.g., L-pol, VP24, VP30, VP35, VP40, nucleoprotein (NP), and/or glycoprotein (GP)) expression and methods of using such siRNA molecules to silence Filovirus (e.g., Ebola virus or Marburg virus) gene expression.

In one aspect, the present invention provides an siRNA molecule comprising a double-stranded sequence of about 15 to about 60 nucleotides in length (e.g., about 15-60, 15-50, 15-40, 15-30, 15-25, or 19-25 nucleotides in length), wherein the siRNA molecule silences expression of a Filovirus gene such as L-pol, VP24, VP30, VP35, VP40, NP, and/or GP from Ebola virus or Marburg virus. In certain instances, the double-stranded sequence comprises a hairpin loop structure.

In some embodiments, the siRNA molecule has 3' overhangs of one, two, three, four, or more nucleotides on one or both sides of the double-stranded region. In other embodiments, the siRNA molecule lacks overhangs (i.e., have blunt ends). Preferably, the siRNA molecule has 3' overhangs of two nucleotides on each side of the double-stranded region. Examples of 3' overhangs include, but are not limited to, 3' deoxythymidine (dT) overhangs of one, two, three, four, or more nucleotides.

In certain instances, the siRNA molecule comprises at least one modified nucleotide in the sense and/or antisense of the sequence. As a non-limiting example, the siRNA molecule can be selectively modified at less than about 20% of the nucleotides in the sequence. Preferably, the modified siRNA contains at least one 2'OMe purine or pyrimidine nucleotide such as a 2'OMe-guanosine, 2'OMe-uridine, 2'OMe-adenosine, and/or 2'OMe-cytosine nucleotide. The modified siRNA molecule is notably less immunostimulatory than a corresponding unmodified siRNA sequence and is capable of silencing expression of the target Filovirus gene.

The siRNA molecule may comprise at least one, two, three, four, five, six, seven, eight, nine, ten, or more of the sequences set forth in Tables 1-15. In some embodiments, the siRNA molecule comprises at least one, two, three, four, five, six, seven, eight, nine, ten, or more of the sequences set forth in Tables 1-13. Preferably, the siRNA molecule comprises at least one, two, three, four, five, six, seven, eight, nine, ten, or more of the sequences set forth in Tables 1-2, such as, e.g., EK1, EK2, EK3, and/or EK4.

In some embodiments, the siRNA molecule described herein further comprises a carrier system, e.g., to deliver the siRNA molecule into a cell of a mammal. Non-limiting examples of carrier systems suitable for use in the present invention include nucleic acid-lipid particles, liposomes, micelles, virosomes, nucleic acid complexes, and mixtures thereof. In certain instances, the siRNA molecule is complexed with a lipid such as a cationic lipid to form a lipoplex. In certain other instances, the siRNA molecule is complexed with a polymer such as a cationic polymer (e.g., polyethylenimine (PEI)) to form a polyplex. The siRNA molecule may also be complexed with cyclodextrin or a polymer thereof. Preferably, the siRNA molecule is encapsulated in a nucleic acid-lipid particle.

The present invention also provides a pharmaceutical composition comprising a siRNA molecule described herein and a pharmaceutically acceptable carrier.

In another aspect, the present invention provides a nucleic acid-lipid particle that targets expression of a Filovirus gene such as L-pol, VP24, VP30, VP35, VP40, NP, and/or GP from Ebola virus or Marburg virus. The nucleic acid-lipid particle comprises an siRNA molecule described herein, a cationic lipid, and a non-cationic lipid. In certain instances, the nucleic acid-lipid particle further comprises a conjugated lipid that inhibits aggregation of particles. Preferably, the nucleic acid-lipid particle comprises an siRNA molecule described herein, a cationic lipid, a non-cationic lipid, and a conjugated lipid that inhibits aggregation of particles.

The cationic lipid may be, e.g., N,N-dioleyl-N,N-dimethylammonium chloride (DODAC), N,N-distearyl-N,N-dimethylammonium bromide (DDAB), N-(1-(2,3-dioleoyloxy)propyl)-N,N,N-trimethylammonium chloride (DOTAP), N-(1-(2,3-dioleyloxy)propyl)-N,N,N-trimethylammonium chloride (DOTMA), N,N-dimethyl-2,3-dioleyloxypropylamine (DODMA), 1,2-DiLinoleyloxy-N,N-dimethylaminopropane (DLinDMA), 1,2-Dilinolenyloxy-N,N-dimethylaminopropane (DLendMA), or mixtures thereof. The cationic lipid may comprise from about 20 mol % to about 50 mol % or about 40 mol % of the total lipid present in the particle.

The non-cationic lipid may be an anionic lipid or a neutral lipid including, but not limited to, distearoylphosphatidylcholine (DSPC), dioleoylphosphatidylethanolamine (DOPE), palmitoyloleoyl-phosphatidylcholine (POPC), palmitoyloleoyl-phosphatidylethanolamine (POPE), palmitoyloleyol-phosphatidylglycerol (POPG), dipalmitoyl-phosphatidylethanolamine (DPPE), dimyristoyl-phosphatidylethanolamine (DMPE), distearoyl-phosphatidylethanolamine (DSPE), monomethyl-phosphatidylethanolamine, dimethylphosphatidylethanolamine, dielaidoyl-phosphatidylethanolamine (DEPE), stearoyloleoyl-phosphatidylethanolamine (SOPE), egg phosphatidylcholine (EPC), cholesterol, or mixtures thereof. The non-cationic lipid may comprise from about 5 mol % to about 90 mol % or about 20 mol % of the total lipid present in the particle.

The conjugated lipid that inhibits aggregation of particles may be a polyethyleneglycol (PEG)-lipid conjugate, a polyamide (ATTA)-lipid conjugate, a cationic-polymer-lipid conjugates (CPLs), or mixtures thereof. In one preferred embodiment, the nucleic acid-lipid particles comprise either a PEG-lipid conjugate or an ATTA-lipid conjugate. In certain embodiments, the PEG-lipid conjugate or ATTA-lipid conjugate is used together with a CPL. The conjugated lipid that inhibits aggregation of particles may comprise a polyethyleneglycol-lipid including, e.g., a PEG-diacylglycerol (DAG), a PEG dialkyloxypropyl (DAA), a PEG-phospholipid, a PEG-ceramide (Cer), or mixtures thereof. The PEG-DAA conjugate may be PEG-dilauryloxypropyl (C12), a PEG-dimyristyloxypropyl (C14), a PEG-dipalmityloxypropyl (C16), and a PEG-distearyloxypropyl (C18). In some embodiments, the conjugated lipid that inhibits aggregation of particles is a CPL that has the formula: A-W—Y, wherein A is a lipid moiety, W is a hydrophilic polymer, and Y is a polycationic moiety. W may be a polymer selected from the group consisting of polyethyleneglycol (PEG), polyamide, polylactic acid, polyglycolic acid, polylactic acid/polyglycolic acid copolymers, or combinations thereof, the polymer having a molecular weight of from about 250 to about 7000 daltons. In some embodiments, Y has at least 4 positive charges at a selected pH. In some embodiments, Y may be lysine, arginine, asparagine, glutamine, derivatives thereof, or combinations thereof. The conjugated lipid that prevents aggregation of particles may be from 0 mol % to about 20 mol % or about 2 mol % of the total lipid present in the particle.

In some embodiments, the nucleic acid-lipid particle further comprises cholesterol at, e.g., about 10 mol % to about 60 mol %, about 30 mol % to about 50 mol %, or about 48 mol % of the total lipid present in the particle.

In certain embodiments, the siRNA molecule in the nucleic acid-lipid particle is not substantially degraded after exposure of the particle to a nuclease at 37° C. for at least 20, 30, 45, or 60 minutes; or after incubation of the particle in serum at 37° C. for at least 30, 45, or 60 minutes.

In some embodiments, the siRNA molecule is fully encapsulated in the nucleic acid-lipid particle. In other embodiments, the siRNA molecule is complexed with the lipid portion of the particle.

The present invention further provides pharmaceutical compositions comprising the nucleic acid-lipid particles described herein and a pharmaceutically acceptable carrier.

In yet another aspect, the siRNA molecule described herein is used in methods for silencing expression of a Filovirus gene such as L-pol, VP24, VP30, VP35, VP40, NP, and/or GP from Ebola virus or Marburg virus. In particular, it is an object of the present invention to provide in vitro and in vivo methods for treatment of a disease or disorder in a mammal by down-regulating or silencing the transcription and/or translation of a target Filovirus gene of interest. In one embodiment, the present invention provides a method for introducing an siRNA that silences expression (e.g., mRNA and/or protein levels) of a Filovirus gene into a cell by contacting the cell with an siRNA molecule described herein. In another embodiment, the present invention provides a method for in vivo delivery of an siRNA that silences expression of a Filovirus gene by administering to a mammal an siRNA molecule described herein. Administration of the siRNA molecule can be by any route known in the art, such as, e.g., oral, intranasal, intravenous, intraperitoneal, intramuscular, intra-articular, intralesional, intratracheal, subcutaneous, or intradermal.

In these methods, the siRNA molecule is typically formulated with a carrier system, and the carrier system comprising the siRNA molecule is administered to a mammal requiring such treatment. Examples of carrier systems suitable for use in the present invention include, but are not limited to, nucleic acid-lipid particles, liposomes, micelles, virosomes, nucleic acid complexes (e.g., lipoplexes, polyplexes, etc.), and mixtures thereof. Alternatively, cells are removed from a mammal such as a human, the siRNA molecule is delivered in vitro, and the cells are then administered to the mammal, such as by injection. The siRNA molecule may comprise at least one, two, three, four, five, six, seven, eight, nine, ten, or more of the sequences set forth in Tables 1-15 (e.g., Tables 1-13). Preferably, the siRNA molecule comprises at least one, two, three, four, five, six, seven, eight, nine, ten, or more of the sequences set forth in Tables 1-2, e.g., EK1, EK2, EK3, and/or EK4.

In some embodiments, the siRNA molecule is in a nucleic acid-lipid particle comprising the siRNA molecule, a cationic lipid, and a non-cationic lipid. Preferably, the siRNA molecule is in a nucleic acid-lipid particle comprising the siRNA molecule, a cationic lipid, a non-cationic lipid, and a conjugated lipid that inhibits aggregation of particles. A therapeutically effective amount of the nucleic acid-lipid particle can be administered to the mammalian subject (e.g., a rodent such as a mouse or a primate such as a human, chimpanzee, or monkey). In certain instances, the mammalian subject has been exposed to a second mammal infected with a Filovirus prior to administration of the particles. In certain other instances, the mammalian subject has been exposed to a fomite contaminated with a Filovirus prior to administration of the particles.

In another embodiment, at least about 1%, 2%, 4%, 6%, 8%, or 10% of the total administered dose of the nucleic acid-lipid particles is present in plasma at about 1, 2, 4, 6, 8, 12, 16, 18, or 24 hours after administration. In a further embodiment, more than about 20%, 30%, or 40% or as much as about 60%, 70%, or 80% of the total administered dose of the nucleic acid-lipid particles is present in plasma at about 1, 4, 6, 8, 10, 12, 20, or 24 hours after administration. In one embodiment, the effect of an siRNA molecule (e.g., down-regulation of the target Filovirus sequence) at a site proximal or distal to the site of administration is detectable at about 12, 24, 48, 72, or 96 hours, or at about 6, 8, 10, 12, 14, 16, 18, 19, 20, 22, 24, 26, or 28 days after administration of the nucleic acid-lipid particles. In another embodiment, downregulation of expression of the target Filovirus sequence is detectable at about 12, 24, 48, 72, or 96 hours, or at about 6, 8, 10, 12, 14, 16, 18, 19, 20, 22, 24, 26, or 28 days after administration. In certain instances, downregulation of expression of a Filovirus gene sequence is detected by measuring Filovirus mRNA or protein levels in a biological sample from the mammal. In certain other instances, downregulation of expression of a Filovirus gene sequence is detected by measuring Filovirus load in a biological sample from the mammal. In some embodiments, downregulation of expression of a Filovirus gene sequence is detected by monitoring symptoms associated with Filovirus infection in the mammal.

The nucleic acid-lipid particles are suitable for use in intravenous nucleic acid delivery as they are stable in circulation, of a size required for pharmacodynamic behavior resulting in access to extravascular sites, and target cell populations. The present invention also provides pharmaceutically acceptable compositions comprising nucleic acid-lipid particles.

Other objects, features, and advantages of the present invention will be apparent to one of skill in the art from the following detailed description and figures.

DETAILED DESCRIPTION OF THE INVENTION

I. Introduction

The present invention is based on the discovery that silencing Filovirus gene expression is an effective means to treat Filovirus (e.g., Ebola virus or Marburg virus) infection. Accordingly, the present invention provides siRNA molecules comprising a double-stranded sequence of about 15 to about 60 nucleotides in length that silence expression of a Filovirus gene (e.g., L-pol, VP24, VP30, VP35, VP40, NP, and/or GP). The present invention also provides nucleic acid-lipid particles that target Filovirus gene expression comprising an siRNA that silences Filovirus gene expression, a cationic lipid, and a non-cationic lipid. In certain instances, the nucleic acid-lipid particles can further comprise a conjugated lipid that inhibits aggregation of particles. The present invention further provides methods of silencing Filovirus gene expression by administering the siRNA molecules described herein to a mammalian subject. In addition, the present invention provides methods of treating a subject who has been exposed to Filovirus or is exhibiting symptoms of Filovirus infection by administering the siRNA molecules described herein.

II. Definitions

Figure 1:
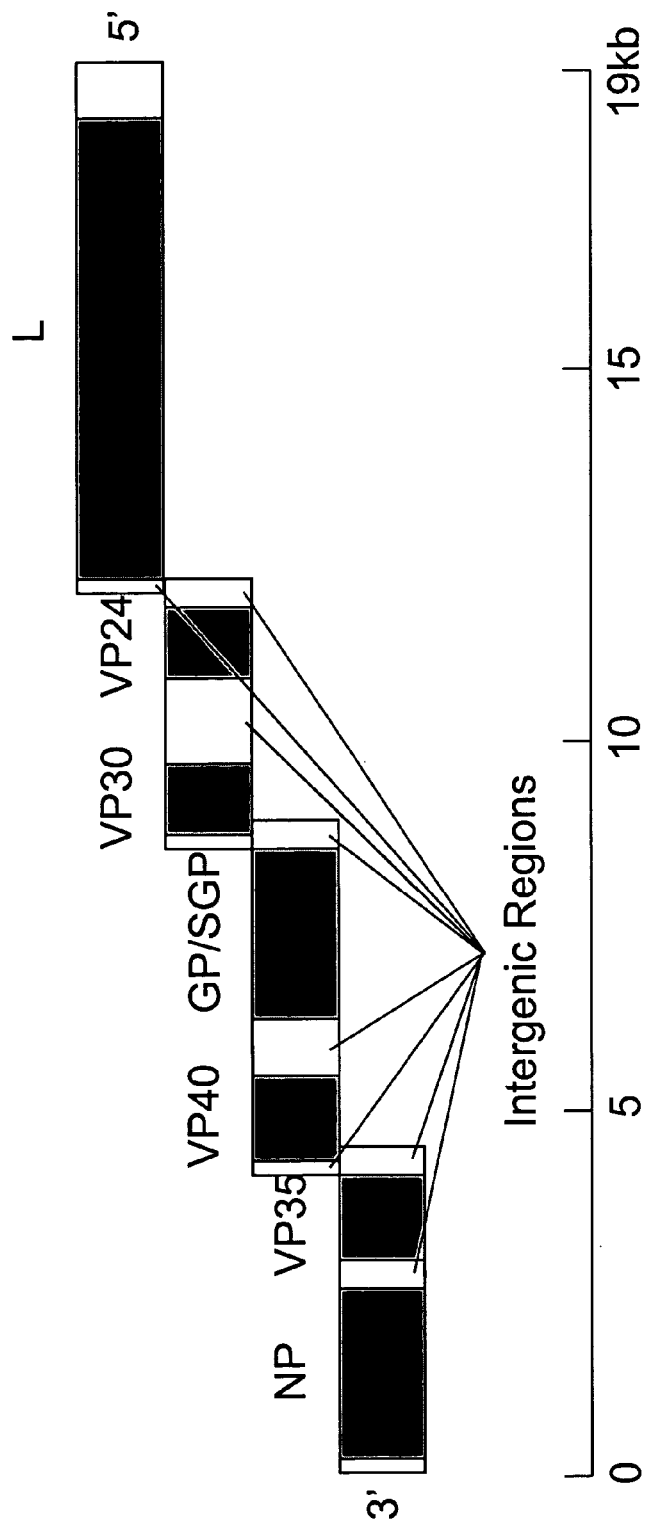
FIG. 1 illustrates the organization of the Ebola virus genome.

The term "Filovirus" or "Filoviridae" refers to single-stranded negative sense RNA viruses that typically infect primates. Filoviruses are able to multiply in virtually all cell types. The Filovirus antigens and virions are found primarily in fibroblasts and interstitium of an infected individual. There are two identified genera of Filoviruses: the Ebola viruses (four species) and the Marburg virus (Marburgvirus). The virions (viral particles) are characteristically shaped as long, cylindrical, filamentous particles which may be straight, curved, coiled, or found in a "6" or "U" shaped configuration. They are occasionally branched and the particles vary greatly in length, but the diameter (about 80 nm) is consistent. The filovirus genome comprises seven genes that encode 4 virion structural proteins (VP30, VP35, nucleoprotein, and a polymerase protein (L-pol)) and 3 membrane-associated proteins (VP40, glycoprotein (GP), and VP24). The GP gene is found fourth from the 3' end of the 7 linearly arranged genes. NP, VP30, VP35, and L-pol are required for viral replication and RNA translation. FIG. 1 shows the organization of the Ebola virus genome. Complete genome sequences for Ebola virus are set forth in, e.g., Genbank Accession Nos. NC_002549

(SEQ ID NO:1); AY769362; NC_006432; NC_004161; AY729654; AY354458; AY142960; AB050936; AF522874; AF499101; AF272001; and AF086833. Ebola virus VP24 sequences are set forth in, e.g., Genbank Accession Nos. U77385 and AY058897. Ebola virus L-pol sequences are set forth in, e.g., Genbank Accession No. X67110. Ebola virus VP40 sequences are set forth in, e.g., Genbank Accession No. AY058896. Ebola virus NP sequences are set forth in, e.g., Genbank Accession No. AY058895. Ebola virus GP sequences are set forth in, e.g., Genbank Accession No. AY058898; Sanchez et al., *Virus Res.,* 29: 215-240 (1993); Will et al., *J. Virol.,* 67: 1203-1210 (1993); Volchkov et al., *FEBS Lett.,* 305:181-184 (1992); and U.S. Pat. No. 6,713, 069. Additional Ebola virus sequences are set forth in, e.g., Genbank Accession Nos. L11365 and X61274. Complete genome sequences for Marburg virus are set forth in, e.g., Genbank Accession Nos. NC_001608 (SEQ ID NO:2); AY430365; AY430366; and AY358025. Marburg virus GP sequences are set forth in, e.g., Genbank Accession Nos. AF005734; AF005733; and AF005732. Marburg virus VP35 sequences are set forth in, e.g., Genbank Accession Nos. AF005731 and AF005730. Additional Marburg virus sequences are set forth in, e.g., Genbank Accession Nos. X64406; Z29337; AF005735; and Z12132.

The term "interfering RNA" or "RNAi" or "interfering RNA sequence" refers to double-stranded RNA (i.e., duplex RNA) that targets (i.e., silences, reduces, or inhibits) expression of a target gene (i.e., by mediating the degradation of mRNAs which are complementary to the sequence of the interfering RNA) when the interfering RNA is in the same cell as the target gene. Interfering RNA thus refers to the double-stranded RNA formed by two complementary strands or by a single, self-complementary strand. Interfering RNA typically has substantial or complete identity to the target gene. The sequence of the interfering RNA can correspond to the full length target gene, or a subsequence thereof.

Interfering RNA includes "small-interfering RNA" or "siRNA," i.e., interfering RNA of about 15-60, 15-50, 15-50, or 15-40 (duplex) nucleotides in length, more typically about 15-30, 15-25, or 19-25 (duplex) nucleotides in length, and is preferably about 20-24, 21-22, or 21-23 (duplex) nucleotides in length (e.g., each complementary sequence of the double-stranded siRNA is about 15-60, 15-50, 15-50, 15-40, 15-30, 15-25, or 19-25 nucleotides in length, preferably about 20-24, 21-22, or 21-23 nucleotides in length, and the double-stranded siRNA is about 15-60, 15-50, 15-50, 15-40, 15-30, 15-25, or 19-25 base pairs in length, preferably about 20-24, 21-22, or 21-23 base pairs in length). siRNA duplexes may comprise 3' overhangs of about 1 to about 4 nucleotides, preferably of about 2 to about 3 nucleotides and 5' phosphate termini. Examples of siRNA include, without limitation, a double-stranded polynucleotide molecule assembled from two separate oligonucleotides, wherein one strand is the sense strand and the other is the complementary antisense strand; a double-stranded polynucleotide molecule assembled from a single oligonucleotide, where the sense and antisense regions are linked by a nucleic acid-based or non-nucleic acid-based linker; a double-stranded polynucleotide molecule with a hairpin secondary structure having self-complementary sense and antisense regions; and a circular single-stranded polynucleotide molecule with two or more loop structures and a stem having self-complementary sense and antisense regions, where the circular polynucleotide can be processed in vivo or in vitro to generate an active double-stranded siRNA molecule.

The siRNA can be chemically synthesized or may be encoded by a plasmid (e.g., transcribed as sequences that automatically fold into duplexes with hairpin loops). siRNA can also be generated by cleavage of longer dsRNA (e.g., dsRNA greater than about 25 nucleotides in length) with the *E coli* RNase III or Dicer. These enzymes process the dsRNA into biologically active siRNA (see, e.g., Yang et al., *PNAS USA,* 99:9942-9947 (2002); Calegari et al., *PNAS USA,* 99:14236 (2002); Byrom et al., *Ambion TechNotes,* 10(1): 4-6 (2003); Kawasaki et al., *Nucleic Acids Res.,* 31: 981-987 (2003); Knight and Bass, *Science,* 293: 2269-2271 (2001); and Robertson et al., *J. Biol. Chem.,* 243: 82 (1968)). Preferably, dsRNA are at least 50 nucleotides to about 100, 200, 300, 400, or 500 nucleotides in length. A dsRNA may be as long as 1000, 1500, 2000, or 5000 nucleotides in length, or longer. The dsRNA can encode for an entire gene transcript or a partial gene transcript.

"Substantial identity" refers to a sequence that hybridizes to a reference sequence under stringent conditions, or to a sequence that has a specified percent identity over a specified region of a reference sequence.

The phrase "stringent hybridization conditions" refers to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assay"(1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization.

Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C. For PCR, a temperature of about 36° C. is typical for low stringency amplification, although annealing temperatures may vary between about 32° C. and 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90° C.-95° C. for 30 sec-2 min., an annealing phase lasting 30 sec.-2 min., and an extension phase of about 72° C. for 1-2 min. Protocols and guidelines for low and high stringency amplification reactions are provided, e.g., in Innis et al. (1990) *PCR Protocols, A Guide to Methods and Applications*, Academic Press, Inc. N.Y.).

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous references, e.g., Current Protocols in Molecular Biology, Ausubel, et al., eds.

The terms "substantially identical" or "substantial identity," in the context of two or more nucleic acids, refer to two or more sequences or subsequences that are the same or have a specified percentage of nucleotides that are the same (i.e., at least about 60%, preferably 65%, 70%, 75%, preferably 80%, 85%, 90%, or 95% identity over a specified region), when compared and aligned for maximum correspondence over a comparison window, or designated region as measured using one of the following sequence comparison algorithms or by manual alignment and visual inspection. This definition, when the context indicates, also refers analogously to the complement of a sequence. Preferably, the substantial identity exists over a region that is at least about 5, 10, 15, 20, 25, 30, 35, 40, 45, 50, 75, or 100 nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window," as used herein, includes reference to a segment of any one of a number of contiguous positions selected from the group consisting of from 20 to 600, usually about 50 to about 200, more usually about 100 to about 150, in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith and Waterman, *Adv. Appl. Math.,* 2:482 (1981), by the homology alignment algorithm of Needleman and Wunsch, *J. Mol. Biol.,* 48:443 (1970), by the search for similarity method of Pearson and Lipman, *Proc. Nat'l Acad. Sci. USA,* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology,* Ausubel et al., eds. (1995 supplement)).

A preferred example of algorithms that are suitable for determining percent sequence identity and sequence similarity are the BLAST and BLAST 2.0 algorithms, which are described in Altschul et al., *Nuc. Acids Res.,* 25:3389-3402 (1977) and Altschul et al., *J. Mol. Biol.,* 215:403-410 (1990), respectively. BLAST and BLAST 2.0 are used with the parameters described herein to determine percent sequence identity for the nucleic acids and proteins of the present invention. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin and Altschul, *Proc. Nat'l. Acad. Sci., USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

The phrase "inhibiting expression of a target gene" refers to the ability of an siRNA molecule of the present invention to silence, reduce, or inhibit expression of a target gene (e.g., a Filovirus gene). To examine the extent of gene silencing, a test sample (e.g., a biological sample from an organism of interest expressing the target gene or a sample of cells in culture expressing the target gene) is contacted with an siRNA that silences, reduces, or inhibits expression of the target gene. Expression of the target gene in the test sample is compared to expression of the target gene in a control sample that is not contacted with the siRNA. Control samples are assigned a value of 100%. Silencing, inhibition, or reduction of expression of a target gene is achieved when the value of test the test sample relative to the control sample is about 95%, 90%, 85%, 80%, 75%, 70%, 65%, 60%, 55%, 50%, 45%, 40%, 35%, 30%, 25%, 20%, or 10%. Suitable assays include, e.g., examination of protein or mRNA levels using techniques known to those of skill in the art such as dot blots, Northern blots, in situ hybridization, ELISA, immunoprecipitation, enzyme function, as well as phenotypic assays known to those of skill in the art.

The term "nucleic acid" or "polynucleotide" refers to a polymer containing at least two deoxyribonucleotides or ribonucleotides in either single- or double-stranded form and include DNA and RNA. DNA may be in the form of, e.g., antisense oligonucleotides, plasmid DNA, pre-condensed DNA, a PCR product, vectors (P1, PAC, BAC, YAC, artificial chromosomes), expression cassettes, chimeric sequences, chromosomal DNA, or derivatives and combinations of these groups. RNA may be in the form of siRNA, mRNA, rRNA, tRNA, vRNA, and combinations thereof. The term encompasses nucleic acids containing known nucleotide analogs or modified backbone residues or linkages which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2'-O-methyl ribonucleotides, and peptide-nucleic acids (PNAs). Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.*, 19:5081 (1991); Ohtsuka et al., *J. Biol. Chem.*, 260:2605-2608 (1985); Rossolini et al., *Mol. Cell. Probes*, 8:91-98 (1994)). "Nucleotides" contain a sugar deoxyribose (DNA) or ribose (RNA), a base, and a phosphate group. Nucleotides are linked together through the phosphate groups. "Bases" include purines and pyrimidines, which further include natural compounds adenine, thymine, guanine, cytosine, uracil, inosine, and natural analogs, and synthetic derivatives of purines and pyrimidines, which include, but are not limited to, modifications which place new reactive groups such as, but not limited to, amines, alcohols, thiols, carboxylates, and alkylhalides.

The term "gene" refers to a nucleic acid (e.g., DNA or RNA) sequence that comprises partial length or entire length coding sequences necessary for the production of a polypeptide or precursor (e.g., Ebola virus or Marburg virus L-pol, VP24, VP30, VP35, VP40, NP, or GP).

"Gene product," as used herein, refers to a product of a gene such as an RNA transcript.

An "effective amount" or "therapeutically effective amount" of an siRNA molecule is an amount sufficient to produce the desired effect, e.g., a decrease in the expression of a target sequence, in comparison to the normal expression level detected in the absence of the siRNA molecule.

The term "lipid" refers to a group of organic compounds that include, but are not limited to, esters of fatty acids and are characterized by being insoluble in water, but soluble in many organic solvents. They are usually divided into at least three classes: (1) "simple lipids" which include fats and oils as well as waxes; (2) "compound lipids" which include phospholipids and glycolipids; and (3) "derived lipids" such as steroids.

"Lipid vesicle" refers to any lipid composition that can be used to deliver a compound such as an siRNA including, but not limited to, liposomes, wherein an aqueous volume is encapsulated by an amphipathic lipid bilayer; or wherein the lipids coat an interior comprising a large molecular component, such as a plasmid comprising an interfering RNA sequence, with a reduced aqueous interior; or lipid aggregates or micelles, wherein the encapsulated component is contained within a relatively disordered lipid mixture. The term lipid vesicle encompasses any of a variety of lipid-based carrier systems including, without limitation, SPLPs, pSPLPs, SNALPs, liposomes, micelles, virosomes, lipid-nucleic acid complexes, and mixtures thereof.

As used herein, "lipid encapsulated" can refer to a lipid formulation that provides a compound such as an siRNA with full encapsulation, partial encapsulation, or both. In some embodiments, the nucleic acid is fully encapsulated in the lipid formulation (e.g., to form an SPLP, pSPLP, SNALP, or other nucleic acid-lipid particle).

As used herein, the term "SNALP" refers to a stable nucleic acid-lipid particle, including SPLP. A SNALP represents a vesicle of lipids coating a reduced aqueous interior comprising a nucleic acid (e.g., siRNA, ssDNA, dsDNA, ssRNA, micro RNA (miRNA), short hairpin RNA (shRNA), dsRNA, or a plasmid, including plasmids from which an interfering RNA is transcribed). As used herein, the term "SPLP" refers to a nucleic acid-lipid particle comprising a nucleic acid (e.g., a plasmid) encapsulated within a lipid vesicle. SNALPs and SPLPs typically contain a cationic lipid, a non-cationic lipid, and a lipid that prevents aggregation of the particle (e.g., a PEG-lipid conjugate). SNALPs and SPLPs are extremely useful for systemic applications, as they exhibit extended circulation lifetimes following intravenous (i.v.) injection, accumulate at distal sites (e.g., sites physically separated from the administration site) and can mediate expression of the transfected gene at these distal sites. SPLPs include "pSPLP," which comprise an encapsulated condensing agent-nucleic acid complex as set forth in PCT Publication No. WO 00/03683.

The nucleic acid-lipid particles of the present invention typically have a mean diameter of about 50 nm to about 150 nm, more typically about 60 nm to about 130 nm, more typically about 70 nm to about 110 nm, most typically about 70 to about 90 nm, and are substantially nontoxic. In addition, the nucleic acids when present in the nucleic acid-lipid particles of the present invention are resistant in aqueous solution to degradation with a nuclease. Nucleic acid-lipid particles and their method of preparation are disclosed in, e.g., U.S. Pat. Nos. 5,976,567; 5,981,501; 6,534,484; 6,586,410; 6,815,432; and WO 96/40964.

The term "vesicle-forming lipid" is intended to include any amphipathic lipid having a hydrophobic moiety and a polar head group, and which by itself can form spontaneously into bilayer vesicles in water, as exemplified by most phospholipids.

The term "vesicle-adopting lipid" is intended to include any amphipathic lipid that is stably incorporated into lipid bilayers in combination with other amphipathic lipids, with its hydrophobic moiety in contact with the interior, hydrophobic region of the bilayer membrane, and its polar head group moiety oriented toward the exterior, polar surface of the membrane. Vesicle-adopting lipids include lipids that on their own tend to adopt a nonlamellar phase, yet which are capable of assuming a bilayer structure in the presence of a bilayer-stabilizing component. A typical example is dioleoylphosphatidylethanolamine (DOPE). Bilayer stabilizing components include, but are not limited to, conjugated lipids that inhibit aggregation of nucleic acid-lipid particles, polyamide oligomers (e.g., ATTA-lipid derivatives), peptides, proteins, detergents, lipid-derivatives, PEG-lipid derivatives such as PEG coupled to dialkyloxypropyls, PEG coupled to diacylglycerols, PEG coupled to phosphatidyl-ethanolamines, PEG conjugated to ceramides (see, e.g., U.S. Pat. No. 5,885,613), cationic PEG lipids, and mixtures thereof. PEG can be conjugated directly to the lipid or may be linked to the lipid via a linker moiety. Any linker moiety suitable for coupling the PEG to a lipid can be used including, e.g., non-ester containing linker moieties and ester-containing linker moieties.

The term "amphipathic lipid" refers, in part, to any suitable material wherein the hydrophobic portion of the lipid material orients into a hydrophobic phase, while the hydrophilic portion orients toward the aqueous phase. Amphipathic lipids are usually the major component of a lipid vesicle. Hydrophilic characteristics derive from the presence of polar or charged groups such as carbohydrates, phosphate, carboxylic, sulfato, amino, sulfhydryl, nitro, hydroxyl, and other like groups. Hydrophobicity can be conferred by the inclusion of apolar groups that include, but are not limited to, long chain saturated and unsaturated aliphatic hydrocarbon groups and such groups substituted by one or more aromatic, cycloaliphatic, or heterocyclic group(s). Examples of amphipathic compounds include, but are not limited to, phospholipids, aminolipids and sphingolipids. Representative examples of phospholipids include, but are not limited to, phosphatidylcholine, phosphatidylethanolamine, phosphatidylserine, phosphatidylinositol, phosphatidic acid, palmitoyloleoyl phosphatidylcholine, lysophosphatidylcholine, lysophosphatidylethanolamine, dipalmitoylphosphatidylcholine, dioleoylphosphatidylcholine, distearoylphosphatidylcholine, and dilinoleoylphosphatidylcholine. Other compounds lacking in phosphorus, such as sphingolipid, glycosphingolipid families, diacylglycerols, and β-acyloxyacids, are also within the group designated as amphipathic lipids. Additionally, the amphipathic lipid described above can be mixed with other lipids including triglycerides and sterols.

The term "neutral lipid" refers to any of a number of lipid species that exist either in an uncharged or neutral zwitterionic form at a selected pH. At physiological pH, such lipids include, for example, diacylphosphatidylcholine, diacylphosphatidylethanolamine, ceramide, sphingomyelin, cephalin, cholesterol, cerebrosides, and diacylglycerols.

The term "non-cationic lipid" refers to any neutral lipid as described above as well as anionic lipids.

The term "anionic lipid" refers to any lipid that is negatively charged at physiological pH. These lipids include, but are not limited to, phosphatidylglycerols, cardiolipins, diacylphosphatidylserines, diacylphosphatidic acids, N-dodecanoyl phosphatidylethanolamines, N-succinyl phosphatidylethanolamines, N-glutarylphosphatidylethanolamines, lysylphosphatidylglycerols, palmitoyloleyolphosphatidylglycerol (POPG), and other anionic modifying groups joined to neutral lipids.

Various suitable cationic lipids may be used in the present invention, either alone or in combination with one or more other cationic lipid species or non-cationic lipid species.

The term "cationic lipid" refers to any of a number of lipid species that carry a net positive charge at a selected pH, such as physiological pH (e.g., pH of about 7.0). It has been surprisingly found that cationic lipids comprising alkyl chains with multiple sites of unsaturation, e.g., at least two or three sites of unsaturation, are particularly useful for forming nucleic acid-lipid particles with increased membrane fluidity. A number of cationic lipids and related analogs, which are also useful in the present invention, are described in U.S. Patent Publication No. 20060083780; U.S. Pat. Nos. 5,208,036; 5,264,618; 5,279,833; 5,283,185; 5,753,613; and 5,785,992; and PCT Publication No. WO 96/10390. Examples of cationic lipids include, but are not limited to, N,N-dioleyl-N,N-dimethylammonium chloride (DODAC), dioctadecyldimethylammonium (DODMA), distearyldimethylammonium (DSDMA), N-(1-(2,3-dioleyloxy)propyl)-N,N,N-trimethylammonium chloride (DOTMA), N,N-distearyl-N,N-dimethylammonium bromide (DDAB), N-(1-(2,3-dioleoyloxy)propyl)-N,N,N-trimethylammonium chloride (DOTAP), 3-(N—(N',N'-dimethylaminoethane)-carbamoyl)cholesterol (DC-Chol), N-(1,2-dimyristyloxyprop-3-yl)-N,N-dimethyl-N-hydroxyethyl ammonium bromide (DMRIE), 1,2-DiLinoleyloxy-N,N-dimethylaminopropane (DLinDMA), 1,2-Dilinolenyloxy-N,N-dimethylaminopropane (DLenDMA), and mixtures thereof. As a non-limiting example, cationic lipids that have a positive charge below physiological pH include, but are not limited to, DODAP, DODMA, and DMDMA. In some cases, the cationic lipids comprise a protonatable tertiary amine head group, $C_{1-8}$ alkyl chains, ether linkages between the head group and alkyl chains, and 0 to 3 double bonds. Such lipids include, e.g., DSDMA, DLinDMA, DLenDMA, and DODMA. The cationic lipids may also comprise ether linkages and pH titratable head groups. Such lipids include, e.g., DODMA.

The term "hydrophobic lipid" refers to compounds having apolar groups that include, but are not limited to, long chain saturated and unsaturated aliphatic hydrocarbon groups and such groups optionally substituted by one or more aromatic, cycloaliphatic, or heterocyclic group(s). Suitable examples include, but are not limited to, diacylglycerol, dialkylglycerol, N—N-dialkylamino, 1,2-diacyloxy-3-aminopropane, and 1,2-dialkyl-3-aminopropane.

The term "fusogenic" refers to the ability of a liposome, a SNALP, or other drug delivery system to fuse with membranes of a cell. The membranes can be either the plasma membrane or membranes surrounding organelles, e.g., endosome, nucleus, etc.

As used herein, the term "aqueous solution" refers to a composition comprising in whole, or in part, water.

As used herein, the term "organic lipid solution" refers to a composition comprising in whole, or in part, an organic solvent having a lipid.

"Distal site," as used herein, refers to a physically separated site, which is not limited to an adjacent capillary bed, but includes sites broadly distributed throughout an organism.

"Serum-stable" in relation to nucleic acid-lipid particles means that the particle is not significantly degraded after exposure to a serum or nuclease assay that would significantly degrade free DNA or RNA. Suitable assays include, for example, a standard serum assay, a DNAse assay, or an RNAse assay.

"Systemic delivery," as used herein, refers to delivery that leads to a broad biodistribution of a compound such as an siRNA within an organism. Some techniques of administration can lead to the systemic delivery of certain compounds, but not others. Systemic delivery means that a useful, preferably therapeutic, amount of a compound is exposed to most parts of the body. To obtain broad biodistribution generally requires a blood lifetime such that the compound is not rapidly degraded or cleared (such as by first pass organs (liver, lung, etc.) or by rapid, nonspecific cell binding) before reaching a disease site distal to the site of administration. Systemic delivery of nucleic acid-lipid particles can be by any means known in the art including, for example, intravenous, subcutaneous, and intraperitoneal. In some embodiments, systemic delivery of nucleic acid-lipid particles is by intravenous delivery.

"Local delivery," as used herein, refers to delivery of a compound such as an siRNA directly to a target site within an organism. For example, a compound can be locally delivered by direct injection into a disease site such as a tumor or other target site such as a site of inflammation or a target organ such as the liver, heart, pancreas, kidney, and the like.

The term "mammal" refers to any mammalian species such as a human, mouse, rat, dog, cat, hamster, guinea pig, rabbit, livestock, and the like.

"Fomite" as used herein refers to any inanimate object that when contaminated with a viable pathogen (e.g., a Filovirus) can transfer the pathogen to a host. Typical fomites include, e.g., hospital and clinic waiting and examination room surfaces (e.g., floors, walls, ceilings, curtains, carpets), needles, syringes, scalpels, catheters, brushes, stethoscopes, laryngoscopes, thermometers, tables, bedding, towels, eating utensils, and the like.

III. siRNAs

The present invention provides an interfering RNA that silences (e.g., partially or completely inhibits) expression of a gene of interest (i.e., a Filovirus gene). An interfering RNA can be provided in several forms. For example, an interfering RNA can be provided as one or more isolated small-interfering RNA (siRNA) duplexes, longer double-stranded RNA (dsRNA), or as siRNA or dsRNA transcribed from a transcriptional cassette in a DNA plasmid. The interfering RNA may also be chemically synthesized. The interfering RNA can be administered alone or co-administered (i.e., concurrently or consecutively) with conventional agents used to treat a Filovirus infection.

In one aspect, the interfering RNA is an siRNA molecule that is capable of silencing expression of a target sequence (e.g., RNA-dependent polymerase (L-pol); glycoprotein (GP); nucleoprotein (NP); viral proteins VP24, VP30, VP35, and VP40) from an Ebola virus or Marburg virus. Suitable siRNA sequences are set forth in, e.g., Tables 1-15, preferably Tables 1-13. Particularly preferred siRNA sequences are set forth in Tables 1-2 (e.g., Ebola L-pol siRNA sequences EK1, EK2, EK3, and/or EK4). For any of the sequences set forth in Tables 1-15, thymine (i.e., "T") can substituted with uracil (i.e., "U") and uracil can be substituted with thymine. In some embodiments, the siRNA molecules are about 15 to 60 nucleotides in length. The synthesized or transcribed siRNA can have 3' overhangs of about 1-4 nucleotides, preferably of about 2-3 nucleotides, and 5' phosphate termini. In some embodiments, the siRNA lacks terminal phosphates.

In certain embodiments, the siRNA molecules of the present invention (e.g., the siRNA sequences set forth in Tables 1-15) are chemically modified as described herein. In certain preferred embodiments, the siRNA molecules of the present invention (e.g., the siRNA sequences set forth in Tables 1-15) comprise less than about 20% modified nucleotides (see, U.S. Provisional Patent Application Nos. 60/711,494 and 60/817,933). The modified siRNA molecule is notably less immunostimulatory than a corresponding unmodified siRNA sequence and retains full RNAi activity against the target sequence. Preferably, the modified siRNA contains at least one 2'OMe purine or pyrimidine nucleotide such as a 2'OMe-guanosine, 2'OMe-uridine, 2'OMe-adenosine, and/or 2'OMe-cytosine nucleotide. The modified nucleotides can be present in one strand (i.e., sense or antisense) or both strands of the siRNA.

Importantly, siRNA molecules that are immunostimulatory can be modified to decrease their immunostimulatory properties without having a negative impact on RNAi activity. For example, an immunostimulatory siRNA can be modified by replacing one or more nucleotides in the sense and/or antisense strand with a modified nucleotide, thereby generating a modified siRNA with reduced immunostimulatory properties that is still capable of silencing expression of the target sequence. In preferred embodiments, one or more of the uridine and/or guanosine nucleotides are modified. Preferably, the modified nucleotide is a 2'OMe nucleotide such as a 2'OMe-guanosine, 2'OMe-uridine, and/or 2'OMe-adenosine nucleotide.

It is also preferred that the modified siRNA comprises less than about 20% modified nucleotides (e.g., less than about 20%, 19%, 18%, 17%, 16%, 15%, 14%, 13%, 12%, 11%, 10%, 9%, 8%, 7%, 6%, 5%, 4%, 3%, 2%, or 1% modified nucleotides) or between about 1%-20% modified nucleotides (e.g., between about 1%-20%, 2%-20%, 3%-20%, 4%-20%, 5%-20%, 6%-20%, 7%-20%, 8%-20%, 9%-20%, 10%-20%, 11%-20%, 12%-20%, 13%-20%, 14%-20%, 15-20%, 16%-20%, 17%-20%, 18%-20%, or 19%-20% modified nucleotides). However, when one or both strands of the siRNA are selectively modified at uridine and/or guanosine nucleotides, the resulting modified siRNA molecule can comprise less than about 25% modified nucleotides (e.g., less than about 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2%, or 1% modified nucleotides) or between about 1%-25% modified nucleotides (e.g., between about 1%-25%, 2%-25%, 3%-25%, 4%-25%, 5%-25%, 6%-25%, 7%-25%, 8%-25%, 9%-25%, 10%-25%, 11%-25%, 12%-25%, 13%-25%, 14%-25%, 15-25%, 16%-25%, 17%-25%, 18%-25%, 19%-25%, 20%-25%, 21%-25%, 22%-25%, 23%-25%, or 24%-25% modified nucleotides).

A. Selection of siRNA Sequences

Suitable siRNA sequences can be identified using any means known in the art. Typically, the methods described in Elbashir et al., *Nature,* 411:494-498 (2001) and Elbashir et al., *EMBO J,* 20:6877-6888 (2001) are combined with rational design rules set forth in Reynolds et al., *Nature Biotech.,* 22(3):326-330 (2004).

Generally, the sequence within about 50 to about 100 nucleotides 3' of the AUG start codon of a transcript from the target gene of interest is scanned for dinucleotide sequences (e.g., AA, NA, CC, GG, or UU, wherein N=C, G, or U) (see, e.g., Elbashir et al., *EMBO J.* 20:6877-6888 (2001)). The nucleotides immediately 3' to the dinucleotide sequences are identified as potential siRNA target sequences. Typically, the 19, 21, 23, 25, 27, 29, 31, 33, 35, or more nucleotides immediately 3' to the dinucleotide sequences are identified as potential siRNA target sites. In some embodiments, the dinucleotide sequence is an AA or NA sequence and the 19 nucleotides immediately 3' to the AA or NA dinucleotide are identified as a potential siRNA target site. siRNA target sites are usually spaced at different positions along the length of the target gene. To further enhance silencing efficiency of the siRNA sequences, potential siRNA target sites may be analyzed to identify sites that do not contain regions of homology to other coding sequences, e.g., in the target cell or organism. For example, a suitable siRNA target site of about 21 base pairs typically will not have more than 16-17 contiguous base pairs of homology to coding sequences in the target cell or organism. If the siRNA sequences are to be expressed from an RNA Pol III promoter, siRNA target sequences lacking more than 4 contiguous A's or T's are selected.

Once a potential siRNA sequence has been identified, the sequence can be analyzed using a variety of criteria known in the art. For example, to enhance their silencing efficiency, the siRNA sequences may be analyzed by a rational design algorithm to identify sequences that have one or more of the following features: (1) G/C content of about 25% to about 60% G/C; (2) at least 3 A/Us at positions 15-19 of the sense strand; (3) no internal repeats; (4) an A at position 19 of the sense strand; (5) an A at position 3 of the sense strand; (6) a U at position 10 of the sense strand; (7) no G/C at position 19 of the sense strand; and (8) no G at position 13 of the sense strand. siRNA design tools that incorporate algorithms that assign suitable values of each of these features and are useful for selection of siRNA can be found at, e.g., http://boz094.ust.hk/RNAi/siRNA. One of skill in the art will appreciate that sequences with one or more of the foregoing characteristics may be selected for further analysis and testing as potential siRNA sequences. siRNA sequences complementary to the siRNA target sites may also be designed.

Additionally, potential siRNA target sequences with one or more of the following criteria can often be eliminated as siRNA: (1) sequences comprising a stretch of 4 or more of the same base in a row; (2) sequences comprising homopolymers of Gs (i.e., to reduce possible non-specific effects due to structural characteristics of these polymers; (3) sequences comprising triple base motifs (e.g., GGG, CCC, AAA, or TTT); (4) sequences comprising stretches of 7 or more G/Cs in a row; and (5) sequences comprising direct repeats of 4 or more bases within the candidates resulting in internal foldback structures. However, one of skill in the art will appreciate that sequences with one or more of the foregoing characteristics may still be selected for further analysis and testing as potential siRNA sequences.

In some embodiments, potential siRNA target sequences may be further analyzed based on siRNA duplex asymmetry as described in, e.g., Khvorova et al., Cell, 115:209-216 (2003); and Schwarz et al., Cell, 115:199-208 (2003). In other embodiments, potential siRNA target sequences may be further analyzed based on secondary structure at the mRNA target site as described in, e.g., Luo et al., Biophys. Res. Commun., 318:303-310 (2004). For example, mRNA secondary structure can be modeled using the Mfold algorithm (available at http://www.bioinfo.rpi.edu/applications/mfold/ma/forml.cgi) to select siRNA sequences which favor accessibility at the mRNA target site where less secondary structure in the form of base-pairing and stem-loops is present.

Once a potential siRNA sequence has been identified, the sequence can be analyzed for the presence of any immunostimulatory properties, e.g., using an in vitro cytokine assay or an in vivo animal model. Motifs in the sense and/or antisense strand of the siRNA sequence such as GU-rich motifs can also provide an indication of whether the sequence may be immunostimulatory. Once an siRNA molecule is found to be immunostimulatory, it can then be modified to decrease its immunostimulatory properties as described herein. As a non-limiting example, an siRNA sequence can be contacted with a mammalian responder cell under conditions such that the cell produces a detectable immune response to determine whether the siRNA is an immunostimulatory or a non-immunostimulatory siRNA. The mammalian responder cell may be from a naïve mammal (i.e., a mammal that has not previously been in contact with the gene product of the siRNA sequence). The mammalian responder cell may be, e.g., a peripheral blood mononuclear cell (PBMC), a macrophage, and the like. The detectable immune response may comprise production of a cytokine or growth factor such as, e.g., TNF-$\alpha$, TNF-$\beta$, IFN-$\alpha$, IFN-$\gamma$, IL-6, IL-12, or a combination thereof. An siRNA molecule identified as being immunostimulatory can then be modified to decrease its immunostimulatory properties by replacing at least one of the nucleotides on the sense and/or antisense strand with modified nucleotides. For example, less than about 20% of the nucleotides in the siRNA duplex can be replaced with modified nucleotides such as 2'OMe nucleotides. The modified siRNA can then be contacted with a mammalian responder cell as described above to confirm that its immunostimulatory properties have been reduced or abrogated.

Suitable in vitro assays for detecting an immune response include, but are not limited to, the double monoclonal antibody sandwich immunoassay technique of David et al. (U.S. Pat. No. 4,376,110); monoclonal-polyclonal antibody sandwich assays (Wide et al., in Kirkham and Hunter, eds., Radioimmunoassay Methods, E. and S. Livingstone, Edinburgh (1970)); the "Western blot" method of Gordon et al. (U.S. Pat. No. 4,452,901); immunoprecipitation of labeled ligand (Brown et al., J. Biol. Chem., 255:4980-4983 (1980)); enzyme-linked immunosorbent assays (ELISA) as described, for example, by Raines et al., J. Biol. Chem., 257:5154-5160 (1982); immunocytochemical techniques, including the use of fluorochromes (Brooks et al., Clin. Exp. Immunol., 39:477 (1980)); and neutralization of activity (Bowen-Pope et al., Proc. Natl. Acad. Sci. USA, 81:2396-2400 (1984)). In addition to the immunoassays described above, a number of other immunoassays are available, including those described in U.S. Pat. Nos. 3,817,827; 3,850,752; 3,901,654; 3,935,074; 3,984,533; 3,996,345; 4,034,074; and 4,098,876.

A non-limiting example of an in vivo model for detecting an immune response includes an in vivo mouse cytokine induction assay that can be performed as follows: (1) siRNA can be administered by standard intravenous injection in the lateral tail vein; (2) blood can be collected by cardiac puncture about 6 hours after administration and processed as plasma for cytokine analysis; and (3) cytokines can be quantified using sandwich ELISA kits according to the manufacturers' instructions (e.g., mouse and human IFN-$\alpha$ (PBL Biomedical; Piscataway, N.J.); human IL-6 and TNF-$\alpha$ (eBioscience; San Diego, Calif.); and mouse IL-6, TNF-$\alpha$, and IFN-$\gamma$ (BD Biosciences; San Diego, Calif.)).

Monoclonal antibodies that specifically bind cytokines and growth factors are commercially available from multiple sources and can be generated using methods known in the art (see, e.g., Kohler and Milstein, Nature, 256: 495-497 (1975); and Harlow and Lane, ANTIBODIES, A LABORATORY MANUAL, Cold Spring Harbor Publication, New York (1999)). Generation of monoclonal antibodies has been previously described and can be accomplished by any means known in the art (see, e.g., Buhring et al. in Hybridoma, Vol. 10, No. 1, pp. 77-78 (1991)). In some methods, the monoclonal antibody is labeled (e.g., with any composition detectable by spectroscopic, photochemical, biochemical, electrical, optical, chemical means, and the like) to facilitate detection.

B. Generating siRNA siRNA molecules can be provided in several forms including, e.g., as one or more isolated small-interfering RNA (siRNA) duplexes, as longer double-stranded RNA (dsRNA), or as siRNA or dsRNA transcribed from a transcriptional cassette in a DNA plasmid. The siRNA sequences may have overhangs (e.g., 3' or 5' overhangs as described in Elbashir et al., Genes Dev., 15:188 (2001) or Nykänen et al., Cell, 107: 309 (2001), or may lack overhangs (i.e., have blunt ends).

An RNA population can be used to provide long precursor RNAs, or long precursor RNAs that have substantial or complete identity to a selected target sequence can be used to make the siRNA. The RNAs can be isolated from cells or tissue, synthesized, and/or cloned according to methods well known to those of skill in the art. The RNA can be a mixed population (obtained from cells or tissue, transcribed from cDNA, subtracted, selected, etc.), or can represent a single target sequence. RNA can be naturally occurring (e.g., isolated from tissue or cell samples), synthesized in vitro (e.g., using T7 or SP6 polymerase and PCR products or a cloned cDNA), or chemically synthesized.

To form a long dsRNA, for synthetic RNAs, the complement is also transcribed in vitro and hybridized to form a dsRNA. If a naturally occuring RNA population is used, the RNA complements are also provided (e.g., to form dsRNA for digestion by E. coli RNAse III or Dicer), e.g., by transcribing cDNAs corresponding to the RNA population, or by using RNA polymerases. The precursor RNAs are then hybridized to form double stranded RNAs for digestion. The dsRNAs can be directly administered to a subject or can be digested in vitro prior to administration.

Alternatively, one or more DNA plasmids encoding one or more siRNA templates are used to provide siRNA. siRNA can be transcribed as sequences that automatically fold into duplexes with hairpin loops from DNA templates in plasmids having RNA polymerase III transcriptional units, for example, based on the naturally occurring transcription units for small nuclear RNA U6 or human RNase P RNA H1 (see, Brummelkamp et al., *Science*, 296:550 (2002); Donzé et al., *Nucleic Acids Res.*, 30:e46 (2002); Paddison et al., *Genes Dev.*, 16:948 (2002); Yu et al., *Proc. Natl. Acad. Sci. USA*, 99:6047 (2002); Lee et al., *Nat. Biotech.*, 20:500 (2002); Miyagishi et al., *Nat. Biotech.*, 20:497 (2002); Paul et al., *Nat. Biotech.*, 20:505 (2002); and Sui et al., *Proc. Natl. Acad. Sci. USA*, 99:5515 (2002)). Typically, a transcriptional unit or cassette will contain an RNA transcript promoter sequence, such as an H1-RNA or a U6 promoter, operably linked to a template for transcription of a desired siRNA sequence and a termination sequence, comprised of 2-3 uridine residues and a polythymidine (T5) sequence (polyadenylation signal) (Brummelkamp et al., supra). The selected promoter can provide for constitutive or inducible transcription. Compositions and methods for DNA-directed transcription of RNA interference molecules is described in detail in U.S. Pat. No. 6,573,099. The transcriptional unit is incorporated into a plasmid or DNA vector from which the interfering RNA is transcribed. Plasmids suitable for in vivo delivery of genetic material for therapeutic purposes are described in detail in U.S. Pat. Nos. 5,962,428 and 5,910,488. The selected plasmid can provide for transient or stable delivery of a target cell. It will be apparent to those of skill in the art that plasmids originally designed to express desired gene sequences can be modified to contain a transcriptional unit cassette for transcription of siRNA.

Methods for isolating RNA, synthesizing RNA, hybridizing nucleic acids, making and screening cDNA libraries, and performing PCR are well known in the art (see, e.g., Gubler and Hoffman, *Gene* 25:263-269 (1983); Sambrook et al., supra; Ausubel et al., supra), as are PCR methods (see, U.S. Pat. Nos. 4,683,195 and 4,683,202; *PCR Protocols: A Guide to Methods and Applications* (Innis et al., eds, 1990)). Expression libraries are also well known to those of skill in the art. Additional basic texts disclosing the general methods of use in this invention include Sambrook et al., *Molecular Cloning, A Laboratory Manual* (2nd ed. 1989); Kriegler, *Gene Transfer and Expression: A Laboratory Manual* (1990); and *Current Protocols in Molecular Biology* (Ausubel et al., eds., 1994).

Preferably, siRNA are chemically synthesized. The oligonucleotides that comprise the siRNA molecule can be synthesized using any of a variety of techniques known in the art, such as those described in Usman et al., *J. Am. Chem. Soc.*, 109:7845 (1987); Scaringe et al., *Nuc. Acids Res.*, 18:5433 (1990); Wincott et al., *Nuc. Acids Res.*, 23:2677-2684 (1995); and Wincott et al., *Methods Mol. Bio.*, 74:59 (1997). The synthesis of oligonucleotides makes use of common nucleic acid protecting and coupling groups, such as dimethoxytrityl at the 5'-end and phosphoramidites at the 3'-end. As a non-limiting example, small scale syntheses can be conducted on an Applied Biosystems synthesizer using a 0.2 µmol scale protocol with a 2.5 min. coupling step for 2'-O-methylated nucleotides. Alternatively, syntheses at the 0.2 µmol scale can be performed on a 96-well plate synthesizer from Protogene (Palo Alto, Calif.). However, a larger or smaller scale of synthesis is also within the scope of the present invention. Suitable reagents for oligonucleotide synthesis, methods for RNA deprotection, and methods for RNA purification are known to those of skill in the art.

The siRNA molecules can also be synthesized via a tandem synthesis technique, wherein both strands are synthesized as a single continuous oligonucleotide fragment or strand separated by a cleavable linker that is subsequently cleaved to provide separate fragments or strands that hybridize to form the siRNA duplex. The linker can be a polynucleotide linker or a non-nucleotide linker. The tandem synthesis of siRNA can be readily adapted to both multiwell/multiplate synthesis platforms as well as large scale synthesis platforms employing batch reactors, synthesis columns, and the like. Alternatively, the siRNA molecules can be assembled from two distinct oligonucleotides, wherein one oligonucleotide comprises the sense strand and the other comprises the antisense strand of the siRNA. For example, each strand can be synthesized separately and joined together by hybridization or ligation following synthesis and/or deprotection. In certain other instances, the siRNA molecules can be synthesized as a single continuous oligonucleotide fragment, where the self-complementary sense and antisense regions hybridize to form an siRNA duplex having hairpin secondary structure.

C. Modifying siRNA Sequences

In certain aspects, the siRNA molecules of the present invention (e.g., the siRNA sequences set forth in Tables 1-15) comprise a duplex having two strands and at least one modified nucleotide in the sense and/or antisense strand, wherein each strand is about 15 to about 60 nucleotides in length. In some embodiments, the siRNA molecules described herein comprise less than about 20% modified nucleotides (e.g., less than about 20%, 15%, 10%, or 5% modified nucleotides) or between about 1%-20% modified nucleotides (e.g., between about 1%-20%, 5%-20%, 10%-20%, or 15-20% modified nucleotides). Preferably, the modified siRNA contains less than about 20% or between about 1%-20% of 2'OMe purine and/or pyrimidine nucleotides such as a 2'OMe-guanosine, 2'OMe-uridine, 2'OMe-adenosine, and/or 2'OMe-cytosine nucleotide. In certain preferred embodiments, one or more of the uridine and/or guanosine nucleotides are modified in the siRNA sequence. Advantageously, the modified siRNA is less immunostimulatory than a corresponding unmodified siRNA sequence, but retains the capability of silencing the expression of a target sequence.

Examples of modified nucleotides suitable for use in the present invention include, but are not limited to, ribonucleotides having a 2'-O-methyl (2'OMe), 2'-deoxy-2'-fluoro, 2'-deoxy, 5-C-methyl, 2'-methoxyethyl, 4'-thio, 2'-amino, or 2'-C-allyl group. Modified nucleotides having a Northern conformation such as those described in, e.g., Saenger, *Principles of Nucleic Acid Structure*, Springer-Verlag Ed. (1984), are also suitable for use in the siRNA molecules of the present invention. Such modified nucleotides include, without limitation, locked nucleic acid (LNA) nucleotides (e.g., 2'-O, 4'-C-methylene-(D-ribofuranosyl) nucleotides), 2'-methoxyethoxy (MOE) nucleotides, 2'-methyl-thio-ethyl nucleotides, 2'-deoxy-2'-fluoro nucleotides, 2'-deoxy-2'-chloro nucleotides, and 2'-azido nucleotides. In certain instances, the siRNA molecule includes one or more G-clamp nucleotides. A G-clamp nucleotide refers to a modified cytosine analog wherein the modifications confer the ability to hydrogen bond both Watson-Crick and Hoogsteen faces of a complementary guanine nucleotide within a duplex (see, e.g., Lin et al., *J. Am. Chem. Soc.*, 120:8531-8532 (1998)). In addition, nucleotides having a nucleotide base analog such as, for example, C-phenyl, C-naphthyl, other aromatic derivatives, inosine, azole carboxamides, and nitroazole derivatives such as 3-nitropyrrole, 4-nitroindole, 5-nitroindole, and 6-nitroindole (see, e.g., Loakes, *Nucl. Acids Res.*, 29:2437-2447 (2001)) can be incorporated into the siRNA molecule.

In certain embodiments, the siRNA molecule can comprise one or more chemical modifications such as terminal cap moieties, phosphate backbone modifications, and the like. Examples of terminal cap moieties include, without limitation, inverted deoxy abasic residues, glyceryl modifications, 4',5'-methylene nucleotides, 1-(β-D-erythrofuranosyl) nucleotides, 4'-thio nucleotides, carbocyclic nucleotides, 1,5-anhydrohexitol nucleotides, L-nucleotides, α-nucleotides, modified base nucleotides, threo-pentofuranosyl nucleotides, acyclic 3',4'-seco nucleotides, acyclic 3,4-dihydroxybutyl nucleotides, acyclic 3,5-dihydroxypentyl nucleotides, 3'-3'-inverted nucleotide moieties, 3'-3'-inverted abasic moieties, 3'-2'-inverted nucleotide moieties, 3'-2'-inverted abasic moieties, 5'-5'-inverted nucleotide moieties, 5'-5'-inverted abasic moieties, 3'-5'-inverted deoxy abasic moieties, 5'-amino-alkyl phosphate, 1,3-diamino-2-propyl phosphate, 3-aminopropyl phosphate, 6-aminohexyl phosphate, 1,2-aminododecyl phosphate, hydroxypropyl phosphate, 1,4-butanediol phosphate, 3'-phosphoramidate, 5'-phosphoramidate, hexylphosphate, aminohexyl phosphate, 3'-phosphate, 5'-amino, 3'-phosphorothioate, 5'-phosphorothioate, phosphorodithioate, and bridging or non-bridging methylphosphonate or 5'-mercapto moieties (see, e.g., U.S. Pat. No. 5,998,203; Beaucage et al., *Tetrahedron*, 49:1925 (1993)). Non-limiting examples of phosphate backbone modifications (i.e., resulting in modified internucleotide linkages) include phosphorothioate, phosphorodithioate, methylphosphonate, phosphotriester, morpholino, amidate, carbamate, carboxymethyl, acetamidate, polyamide, sulfonate, sulfonamide, sulfamate, formacetal, thioformacetal, and alkylsilyl substitutions (see, e.g., Hunziker et al., *Nucleic Acid Analogues: Synthesis and Properties*, in *Modern Synthetic Methods*, VCH, 331-417 (1995); Mesmaeker et al., *Novel Backbone Replacements for Oligonucleotides*, in *Carbohydrate Modifications in Antisense Research*, ACS, 24-39 (1994)). Such chemical modifications can occur at the 5'-end and/or 3'-end of the sense strand, antisense strand, or both strands of the siRNA.

In some embodiments, the sense and/or antisense strand can comprise a 3'-terminal overhang having about 1 to about 4 (e.g., 1, 2, 3, or 4) 2'-deoxy ribonucleotides and/or any combination of modified and unmodified nucleotides. Additional examples of modified nucleotides and types of chemical modifications that can be introduced into the modified siRNA molecule are described, e.g., in UK Patent No. GB 2,397,818 B and U.S. Patent Publication Nos. 20040192626 and 20050282188.

The siRNA molecules described herein can optionally comprise one or more non-nucleotides in one or both strands of the siRNA. As used herein, the term "non-nucleotide" refers to any group or compound that can be incorporated into a nucleic acid chain in the place of one or more nucleotide units, including sugar and/or phosphate substitutions, and allows the remaining bases to exhibit their activity. The group or compound is abasic in that it does not contain a commonly recognized nucleotide base such as adenosine, guanine, cytosine, uracil, or thymine and therefore lacks a base at the 1'-position.

In other embodiments, chemical modification of the siRNA comprises attaching a conjugate to the siRNA molecule. The conjugate can be attached at the 5' and/or 3'-end of the sense and/or antisense strand of the siRNA via a covalent attachment such as, e.g., a biodegradable linker. The conjugate can also be attached to the siRNA, e.g., through a carbamate group or other linking group (see, e.g., U.S. Patent Publication Nos. 20050074771, 20050043219, and 20050158727). In certain instances, the conjugate is a molecule that facilitates the delivery of the siRNA into a cell. Examples of conjugate molecules suitable for attachment to an siRNA include, without limitation, steroids such as cholesterol, glycols such as polyethylene glycol (PEG), human serum albumin (HSA), fatty acids, carotenoids, terpenes, bile acids, folates (e.g., folic acid, folate analogs and derivatives thereof), sugars (e.g., galactose, galactosamine, N-acetyl galactosamine, glucose, mannose, fructose, fucose, etc.), phospholipids, peptides, ligands for cellular receptors capable of mediating cellular uptake, and combinations thereof (see, e.g., U.S. Patent Publication Nos. 20030130186, 20040110296, and 20040249178; U.S. Pat. No. 6,753,423). Other examples include the lipophilic moiety, vitamin, polymer, peptide, protein, nucleic acid, small molecule, oligosaccharide, carbohydrate cluster, intercalator, minor groove binder, cleaving agent, and cross-linking agent conjugate molecules described in U.S. Patent Publication Nos. 20050119470 and 20050107325. Yet other examples include the 2'-O-alkyl amine, 2'-O-alkoxyalkyl amine, polyamine, C5-cationic modified pyrimidine, cationic peptide, guanidinium group, amidininium group, cationic amino acid conjugate molecules described in U.S. Patent Publication No. 20050153337. Additional examples include the hydrophobic group, membrane active compound, cell penetrating compound, cell targeting signal, interaction modifier, and steric stabilizer conjugate molecules described in U.S. Patent Publication No. 20040167090. Further examples include the conjugate molecules described in U.S. Patent Publication No. 20050239739. The type of conjugate used and the extent of conjugation to the siRNA molecule can be evaluated for improved pharmacokinetic profiles, bioavailability, and/or stability of the siRNA. As such, one skilled in the art can screen siRNA molecules having various conjugates attached thereto to identify ones having improved properties using any of a variety of well-known in vitro cell culture or in vivo animal models.

IV. Carrier Systems Containing siRNA

In one aspect, the present invention provides carrier systems containing the siRNA molecules described herein. In some embodiments, the carrier system is a lipid-based carrier system such as a stabilized nucleic acid-lipid particle (e.g., SNALP or SPLP), cationic lipid or liposome nucleic acid complexes (i.e., lipoplexes), a liposome, a micelle, a virosome, or a mixture thereof. In other embodiments, the carrier system is a polymer-based carrier system such as a cationic polymer-nucleic acid complex (i.e., polyplex). In additional embodiments, the carrier system is a cyclodextrin-based carrier system such as a cyclodextrin polymer-nucleic acid complex. In further embodiments, the carrier system is a protein-based carrier system such as a cationic peptide-nucleic acid complex. Preferably, the carrier system is a stabilized nucleic acid-lipid particle such as a SNALP or SPLP. One skilled in the art will appreciate that the siRNA molecule of the present invention can also be delivered as a naked siRNA molecule.

A. Stabilized Nucleic Acid-Lipid Particles

The stabilized nucleic acid-lipid particles (SNALPs) of the present invention typically comprise an siRNA molecule that targets expression of a Filovirus gene (e.g., an Ebola virus or Marburg virus gene), a cationic lipid (e.g., a cationic lipid of Formula I or II), and a non-cationic lipid. The SNALPs can further comprise a bilayer stabilizing component (i.e., a conjugated lipid that inhibits aggregation of the particles). The SNALPs may comprise at least 1, 2, 3, 4, 5, 6, 7, 8, 9, 10, or more of the sequences set forth in Tables 1-15.

The SNALPs of the present invention typically have a mean diameter of about 50 nm to about 150 nm, more typically about 60 nm to about 130 nm, more typically about 70 nm to about 110 nm, most typically about 70 to about 90 nm, and are substantially nontoxic. In addition, the nucleic acids are resistant in aqueous solution to degradation with a nuclease when present in the nucleic acid-lipid particles. Nucleic acid-lipid particles and their method of preparation are disclosed in, e.g., U.S. Pat. Nos. 5,753,613; 5,785,992; 5,705,385; 5,976,567; 5,981,501; 6,110,745; and 6,320,017; and PCT Publication No. WO 96/40964.

1. Cationic Lipids

Any of a variety of cationic lipids may be used in the stabilized nucleic acid-lipid particles of the present invention, either alone or in combination with one or more other cationic lipid species or non-cationic lipid species.

Cationic lipids which are useful in the present invention can be any of a number of lipid species which carry a net positive charge at physiological pH. Such lipids include, but are not limited to, DODAC, DODMA, DSDMA, DOTMA, DDAB, DOTAP, DOSPA, DOGS, DC-Chol, DMRIE, and mixtures thereof. A number of these lipids and related analogs have been described in U.S. Patent Publication No. 20060083780; U.S. Pat. Nos. 5,208,036; 5,264,618; 5,279,833; 5,283,185; and 5,753,613; and 5,785,992; and PCT Publication No. WO 96/10390. Additionally, a number of commercial preparations of cationic lipids are available and can be used in the present invention. These include, for example, LIPOFECTIN® (commercially available cationic liposomes comprising DOTMA and DOPE, from GIBCO/BRL, Grand Island, N.Y., USA); LIPOFECTAMINE® (commercially available cationic liposomes comprising DOSPA and DOPE, from GIBCO/BRL); and TRANSFECTAM® (commercially available cationic liposomes comprising DOGS from Promega Corp., Madison, Wis., USA).

Furthermore, cationic lipids of Formula I having the following structures are useful in the present invention.

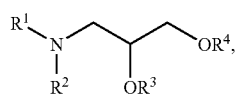

(I)

wherein $R^1$ and $R^2$ are independently selected and are H or $C_1$-$C_3$ alkyls, $R^3$ and $R^4$ are independently selected and are alkyl groups having from about 10 to about 20 carbon atoms, and at least one of $R^3$ and $R^4$ comprises at least two sites of unsaturation. In certain instances, $R^3$ and $R^4$ are both the same, i.e., $R^3$ and $R^4$ are both linoleyl (C18), etc. In certain other instances, $R^3$ and $R^4$ are different, i.e., $R^3$ is tetradectrienyl (C14) and $R^4$ is linoleyl (C18). In a preferred embodiment, the cationic lipid of Formula I is symmetrical, i.e., $R^3$ and $R^4$ are both the same. In another preferred embodiment, both $R^3$ and $R^4$ comprise at least two sites of unsaturation. In some embodiments, $R^3$ and $R^4$ are independently selected from dodecadienyl, tetradecadienyl, hexadecadienyl, linoleyl, and icosadienyl. In a preferred embodiment, $R^3$ and $R^4$ are both linoleyl. In some embodiments, $R^3$ and $R^4$ comprise at least three sites of unsaturation and are independently selected from, e.g., dodecatrienyl, tetradectrienyl, hexadectrienyl, linolenyl, and icosatrienyl. In a particularly preferred embodiments, the cationic lipid of Formula I is DLinDMA or DLenDMA.

Moreover, cationic lipids of Formula II having the following structures are useful in the present invention.

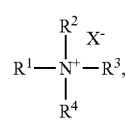

(II)

wherein $R^1$ and $R^2$ are independently selected and are H or $C_1$-$C_3$ alkyls, $R^3$ and $R^4$ are independently selected and are alkyl groups having from about 10 to about 20 carbon atoms, and at least one of $R^3$ and $R^4$ comprises at least two sites of unsaturation. In certain instances, $R^3$ and $R^4$ are both the same, i.e., $R^3$ and $R^4$ are both linoleyl (C18), etc. In certain other instances, $R^3$ and $R^4$ are different, i.e., $R^3$ is tetradectrienyl (C14) and $R^4$ is linoleyl (C18). In a preferred embodiment, the cationic lipids of the present invention are symmetrical, i.e., $R^3$ and $R^4$ are both the same. In another preferred embodiment, both $R^3$ and $R^4$ comprise at least two sites of unsaturation. In some embodiments, $R^3$ and $R^4$ are independently selected from dodecadienyl, tetradecadienyl, hexadecadienyl, linoleyl, and icosadienyl. In a preferred embodiment, $R^3$ and $R^4$ are both linoleyl. In some embodiments, $R^3$ and $R^4$ comprise at least three sites of unsaturation and are independently selected from, e.g., dodecatrienyl, tetradectrienyl, hexadectrienyl, linolenyl, and icosatrienyl.

The cationic lipid typically comprises from about 2 mol % to about 60 mol %, from about 5 mol % to about 50 mol %, from about 10 mol % to about 50 mol %, from about 20 mol % to about 50 mol %, from about 20 mol % to about 40 mol %, from about 30 mol % to about 40 mol %, or about 40 mol % of the total lipid present in the particle. It will be readily apparent to one of skill in the art that depending on the intended use of the particles, the proportions of the components can be varied and the delivery efficiency of a particular formulation can be measured using, e.g., an endosomal release parameter (ERP) assay. For example, for systemic delivery, the cationic lipid may comprise from about 5 mol % to about 15 mol % of the total lipid present in the particle, and for local or regional delivery, the cationic lipid may comprise from about 30 mol % to about 50 mol %, or about 40 mol % of the total lipid present in the particle.

2. Non-cationic Lipids

The non-cationic lipids used in the stabilized nucleic acid-lipid particles of the present invention can be any of a variety of neutral uncharged, zwitterionic, or anionic lipids capable of producing a stable complex. They are preferably neutral, although they can alternatively be positively or negatively charged. Examples of non-cationic lipids include, without limitation, phospholipid-related materials such as lecithin, phosphatidylethanolamine, lysolecithin, lysophosphatidylethanolamine, phosphatidylserine, phosphatidylinositol, sphingomyelin, egg sphingomyelin (ESM), cephalin, cardiolipin, phosphatidic acid, cerebrosides, dicetylphosphate, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoylphosphatidylethanolamine (DOPE), palmitoyloleoyl-phosphatidylcholine (POPC), palmitoyloleoyl-phosphatidylethanolamine (POPE), palmitoyloleyol-phosphatidylglycerol (POPG), dioleoylphosphatidylethanolamine 4-(N-maleimidomethyl)-cyclohexane-1-carboxylate (DOPE-mal), dipalmitoyl-phosphatidylethanolamine (DPPE), dimyristoyl-phosphatidylethanolamine (DMPE), distearoyl-phosphatidylethanolamine (DSPE), monomethyl-phosphatidylethanolamine, dimethyl-phosphatidylethanolamine, dielaidoyl-phosphatidylethanolamine (DEPE), and stearoyloleoyl-phosphatidylethanolamine (SOPE). Non-cationic lipids or sterols such as cholesterol may also be present. Additional nonphosphorous containing lipids include, e.g., stearylamine, dodecylamine, hexadecylamine, acetyl palmitate, glycerolricinoleate, hexadecyl stereate, isopropyl myristate, amphoteric acrylic polymers, triethanolamine-lauryl sulfate, alkyl-aryl sulfate polyethyloxylated fatty acid amides, dioctadecyldimethyl ammonium bromide, ceramide, diacylphosphatidylcholine, diacylphosphatidylethanolamine, and the like. Other lipids such as lysophosphatidylcholine and lysophosphatidylethanolamine may be present. Non-cationic lipids also include polyethylene glycol-based polymers such as PEG 2000, PEG 5000, and polyethylene glycol conjugated to phospholipids or to ceramides (referred to as PEG-Cer), as described in U.S. patent application Ser. No. 08/316,429.

In preferred embodiments, the non-cationic lipids are diacylphosphatidylcholine (e.g., distearoylphosphatidylcholine, dioleoylphosphatidylcholine, dipalmitoylphosphatidylcholine, and dilinoleoylphosphatidylcholine), diacylphosphatidylethanolamine (e.g., dioleoylphosphatidylethanolamine and palmitoyloleoyl-phosphatidylethanolamine), ceramide, or sphingomyelin. The acyl groups in these lipids are preferably acyl groups derived from fatty acids having $C_{10}$-$C_{24}$ carbon chains. More preferably, the acyl groups are lauroyl, myristoyl, palmitoyl, stearoyl, or oleoyl. In particularly preferred embodiments, the non-cationic lipid includes one or more of cholesterol, DOPE, or ESM.

The non-cationic lipid typically comprises from about 5 mol % to about 90 mol %, from about 10 mol % to about 85 mol %, from about 20 mol % to about 80 mol %, or about 20 mol % of the total lipid present in the particle. The particles may further comprise cholesterol. If present, the cholesterol typically comprises from about 0 mol % to about 10 mol %, from about 2 mol % to about 10 mol %, from about 10 mol % to about 60 mol %, from about 12 mol % to about 58 mol %, from about 20 mol % to about 55 mol %, from about 30 mol % to about 50 mol %, or about 48 mol % of the total lipid present in the particle.

3. Bilayer Stabilizing Component

In addition to cationic and non-cationic lipids, the stabilized nucleic acid-lipid particles of the present invention can comprise a bilayer stabilizing component (BSC) such as an ATTA-lipid or a PEG-lipid such as PEG coupled to dialkyloxypropyls (PEG-DAA) as described in, e.g., PCT Publication No. WO 05/026372, PEG coupled to diacylglycerol (PEG-DAG) as described in, e.g., U.S. Patent Publication Nos. 20030077829 and 2005008689, PEG coupled to phospholipids such as phosphatidylethanolamine (PEG-PE), PEG conjugated to ceramides, or a mixture thereof (see, e.g., U.S. Pat. No. 5,885,613). In a preferred embodiment, the BSC is a conjugated lipid that prevents the aggregation of particles. Suitable conjugated lipids include, but are not limited to, PEG-lipid conjugates, ATTA-lipid conjugates, cationic-polymer-lipid conjugates (CPLs), and mixtures thereof. In another preferred embodiment, the particles comprise either a PEG-lipid conjugate or an ATTA-lipid conjugate together with a CPL.

PEG is a linear, water-soluble polymer of ethylene PEG repeating units with two terminal hydroxyl groups. PEGs are classified by their molecular weights; for example, PEG 2000 has an average molecular weight of about 2,000 daltons, and PEG 5000 has an average molecular weight of about 5,000 daltons. PEGs are commercially available from Sigma Chemical Co. and other companies and include, for example, the following: monomethoxypolyethylene glycol (MePEG-OH), monomethoxypolyethylene glycol-succinate (MePEG-S), monomethoxypolyethylene glycol-succinimidyl succinate (MePEG-S—NHS), monomethoxypolyethylene glycolamine (MePEG-NH$_2$), monomethoxypolyethylene glycol-tresylate (MePEG-TRES), and monomethoxypolyethylene glycol-imidazolyl-carbonyl (MePEG-IM). In addition, monomethoxypolyethyleneglycol-acetic acid (MePEG-CH$_2$COOH) is particularly useful for preparing the PEG-lipid conjugates including, e.g., PEG-DAA conjugates.

In a preferred embodiment, the PEG has an average molecular weight of from about 550 daltons to about 10,000 daltons, more preferably from about 750 daltons to about 5,000 daltons, more preferably from about 1,000 daltons to about 5,000 daltons, more preferably from about 1,500 daltons to about 3,000 daltons, and even more preferably about 2,000 daltons or about 750 daltons. The PEG can be optionally substituted by an alkyl, alkoxy, acyl, or aryl group. The PEG can be conjugated directly to the lipid or may be linked to the lipid via a linker moiety. Any linker moiety suitable for coupling the PEG to a lipid can be used including, e.g., non-ester containing linker moieties and ester-containing linker moieties. In a preferred embodiment, the linker moiety is a non-ester containing linker moiety. As used herein, the term "non-ester containing linker moiety" refers to a linker moiety that does not contain a carboxylic ester bond (—OC(O)—). Suitable non-ester containing linker moieties include, but are not limited to, amido (—C(O)NH—), amino (—NR—), carbonyl (—C(O)—), carbamate (—NHC(O)O—), urea (—NHC(O)NH—), disulphide (—S—S—), ether (—O—), succinyl (—(O)CCH$_2$CH$_2$C(O)—), succinamidyl (—NHC(O)CH$_2$CH$_2$C(O)NH—), ether, disulphide, as well as combinations thereof (such as a linker containing both a carbamate linker moiety and an amido linker moiety). In a preferred embodiment, a carbamate linker is used to couple the PEG to the lipid.

In other embodiments, an ester containing linker moiety is used to couple the PEG to the lipid. Suitable ester containing linker moieties include, e.g., carbonate (—OC(O)O—), succinoyl, phosphate esters (—O—(O)POH—O—), sulfonate esters, and combinations thereof.

Phosphatidylethanolamines having a variety of acyl chain groups of varying chain lengths and degrees of saturation can be conjugated to PEG to form the bilayer stabilizing component. Such phosphatidylethanolamines are commercially available, or can be isolated or synthesized using conventional techniques known to those of skilled in the art. Phosphatidylethanolamines containing saturated or unsaturated fatty acids with carbon chain lengths in the range of $C_{10}$ to $C_{20}$ are preferred. Phosphatidylethanolamines with mono- or diunsaturated fatty acids and mixtures of saturated and unsaturated fatty acids can also be used. Suitable phosphatidylethanolamines include, but are not limited to, dimyristoyl-phosphatidylethanolamine (DMPE), dipalmitoyl-phosphatidylethanolamine (DPPE), dioleoylphosphatidylethanolamine (DOPE), and distearoyl-phosphatidylethanolamine (DSPE).

The term "ATTA" or "polyamide" refers to, without limitation, compounds disclosed in U.S. Pat. Nos. 6,320,017 and 6,586,559. These compounds include a compound having the formula:

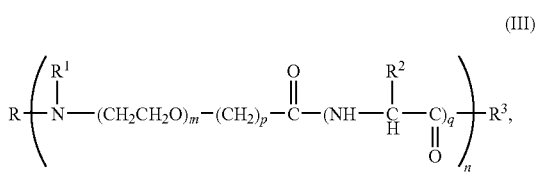

(III)

(VI)

wherein R is a member selected from the group consisting of hydrogen, alkyl and acyl; $R^1$ is a member selected from the group consisting of hydrogen and alkyl; or optionally, R and $R^1$ and the nitrogen to which they are bound form an azido moiety; $R^2$ is a member of the group selected from hydrogen, optionally substituted alkyl, optionally substituted aryl and a side chain of an amino acid; $R^3$ is a member selected from the group consisting of hydrogen, halogen, hydroxy, alkoxy, mercapto, hydrazino, amino and $NR^4R^5$, wherein $R^4$ and $R^5$ are independently hydrogen or alkyl; n is 4 to 80; m is 2 to 6; p is 1 to 4; and q is 0 or 1. It will be apparent to those of skill in the art that other polyamides can be used in the compounds of the present invention.

The term "diacylglycerol" refers to a compound having 2 fatty acyl chains, $R^1$ and $R^2$, both of which have independently between 2 and 30 carbons bonded to the 1- and 2-position of glycerol by ester linkages. The acyl groups can be saturated or have varying degrees of unsaturation. Suitable acyl groups include, but are not limited to, lauryl (C12), myristyl (C14), palmityl (C16), stearyl (C18), and icosyl (C20). In preferred embodiments, $R^1$ and $R^2$ are the same, i.e., $R^1$ and $R^2$ are both myristyl (i.e., dimyristyl), $R^1$ and $R^2$ are both stearyl (i.e., distearyl), etc. Diacylglycerols have the following general formula:

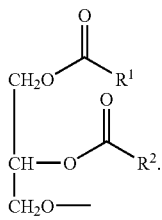

(IV)

The term "dialkyloxypropyl" refers to a compound having 2 alkyl chains, $R^1$ and $R^2$, both of which have independently between 2 and 30 carbons. The alkyl groups can be saturated or have varying degrees of unsaturation. Dialkyloxypropyls have the following general formula:

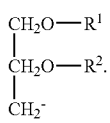

(V)

In a preferred embodiment, the PEG-lipid is a PEG-DAA conjugate having the following formula:

wherein $R^1$ and $R^2$ are independently selected and are long-chain alkyl groups having from about 10 to about 22 carbon atoms; PEG is a polyethyleneglycol; and L is a non-ester containing linker moiety or an ester containing linker moiety as described above. The long-chain alkyl groups can be saturated or unsaturated. Suitable alkyl groups include, but are not limited to, lauryl (C12), myristyl (C14), palmityl (C16), stearyl (C18), and icosyl (C20). In preferred embodiments, $R^1$ and $R^2$ are the same, i.e., $R^1$ and $R^2$ are both myristyl (i.e., dimyristyl), $R^1$ and $R^2$ are both stearyl (i.e., distearyl), etc.

In Formula VI above, the PEG has an average molecular weight ranging from about 550 daltons to about 10,000 daltons, more preferably from about 750 daltons to about 5,000 daltons, more preferably from about 1,000 daltons to about 5,000 daltons, more preferably from about 1,500 daltons to about 3,000 daltons, and even more preferably about 2,000 daltons or about 750 daltons. The PEG can be optionally substituted with alkyl, alkoxy, acyl, or aryl. In a preferred embodiment, the terminal hydroxyl group is substituted with a methoxy or methyl group.

In a preferred embodiment, "L" is a non-ester containing linker moiety. Suitable non-ester containing linkers include, but are not limited to, an amido linker moiety, an amino linker moiety, a carbonyl linker moiety, a carbamate linker moiety, a urea linker moiety, an ether linker moiety, a disulphide linker moiety, a succinamidyl linker moiety, and combinations thereof. In a preferred embodiment, the non-ester containing linker moiety is a carbamate linker moiety (i.e., a PEG-C-DAA conjugate). In another preferred embodiment, the non-ester containing linker moiety is an amido linker moiety (i.e., a PEG-A-DAA conjugate). In yet another preferred embodiment, the non-ester containing linker moiety is a succinamidyl linker moiety (i.e., a PEG-S-DAA conjugate).

The PEG-DAA conjugates are synthesized using standard techniques and reagents known to those of skill in the art. It will be recognized that the PEG-DAA conjugates will contain various amide, amine, ether, thio, carbamate, and urea linkages. Those of skill in the art will recognize that methods and reagents for forming these bonds are well known and readily available. See, e.g., March, ADVANCED ORGANIC CHEMISTRY (Wiley 1992), Larock, COMPREHENSIVE ORGANIC TRANSFORMATIONS (VCH 1989); and Fumiss, VOGEL'S TEXTBOOK OF PRACTICAL ORGANIC CHEMISTRY 5th ed. (Longman 1989). It will also be appreciated that any functional groups present may require protection and deprotection at different points in the synthesis of the PEG-DAA conjugates. Those of skill in the art will recognize that such techniques are well known. See, e.g., Green and Wuts, PROTECTIVE GROUPS IN ORGANIC SYNTHESIS (Wiley 1991).

Preferably, the PEG-DAA conjugate is a dilauryloxypropyl (C12)-PEG conjugate, dimyristyloxypropyl (C14)-PEG conjugate, a dipalmityloxypropyl (C16)-PEG conjugate, or a distearyloxypropyl (C18)-PEG conjugate. Those of skill in the art will readily appreciate that other dialkyloxypropyls can be used in the PEG-DAA conjugates of the present invention.

In addition to the foregoing, it will be readily apparent to those of skill in the art that other hydrophilic polymers can be used in place of PEG. Examples of suitable polymers that can be used in place of PEG include, but are not limited to, polyvinylpyrrolidone, polymethyloxazoline, polyethyloxazoline, polyhydroxypropyl methacrylamide, polymethacrylamide and polydimethylacrylamide, polylactic acid, polyglycolic acid, and derivatized celluloses such as hydroxymethylcellulose or hydroxyethylcellulose.

In addition to the foregoing components, the particles (e.g., SNALPs or SPLPs) of the present invention can further comprise cationic poly(ethylene glycol) (PEG) lipids or CPLs that have been designed for insertion into lipid bilayers to impart a positive charge (see, e.g., Chen et al., *Bioconj. Chem.*, 11:433-437 (2000)). Suitable SPLPs and SPLP-CPLs for use in the present invention, and methods of making and using SPLPs and SPLP-CPLs, are disclosed, e.g., in U.S. Pat. No. 6,852,334 and PCT Publication No. WO 00/62813. Cationic polymer lipids (CPLs) useful in the present invention have the following architectural features: (1) a lipid anchor, such as a hydrophobic lipid, for incorporating the CPLs into the lipid bilayer; (2) a hydrophilic spacer, such as a polyethylene glycol, for linking the lipid anchor to a cationic head group; and (3) a polycationic moiety, such as a naturally occurring amino acid, to produce a protonizable cationic head group.

Suitable CPLs include compounds of Formula VII:

A-W—Y      (VII), wherein A, W, and Y are as described below.

With reference to Formula VII, "A" is a lipid moiety such as an amphipathic lipid, a neutral lipid, or a hydrophobic lipid that acts as a lipid anchor. Suitable lipid examples include vesicle-forming lipids or vesicle adopting lipids and include, but are not limited to, diacylglycerolyls, dialkylglycerolyls, N—N-dialkylaminos, 1,2-diacyloxy-3-aminopropanesi, and 1,2-dialkyl-3-aminopropanes.

"W" is a polymer or an oligomer such as a hydrophilic polymer or oligomer. Preferably, the hydrophilic polymer is a biocompatible polymer that is nonimmunogenic or possesses low inherent immunogenicity. Alternatively, the hydrophilic polymer can be weakly antigenic if used with appropriate adjuvants. Suitable nonimmunogenic polymers include, but are not limited to, PEG, polyamides, polylactic acid, polyglycolic acid, polylactic acid/polyglycolic acid copolymers, and combinations thereof. In a preferred embodiment, the polymer has a molecular weight of from about 250 to about 7,000 daltons.

"Y" is a polycationic moiety. The term polycationic moiety refers to a compound, derivative, or functional group having a positive charge, preferably at least 2 positive charges at a selected pH, preferably physiological pH. Suitable polycationic moieties include basic amino acids and their derivatives such as arginine, asparagine, glutamine, lysine, and histidine; spermine; spermidine; cationic dendrimers; polyamines; polyamine sugars; and amino polysaccharides. The polycationic moieties can be linear, such as linear tetralysine, branched or dendrimeric in structure. Polycationic moieties have between about 2 to about 15 positive charges, preferably between about 2 to about 12 positive charges, and more preferably between about 2 to about 8 positive charges at selected pH values. The selection of which polycationic moiety to employ may be determined by the type of particle application which is desired.

The charges on the polycationic moieties can be either distributed around the entire particle moiety, or alternatively, they can be a discrete concentration of charge density in one particular area of the particle moiety e.g., a charge spike. If the charge density is distributed on the particle, the charge density can be equally distributed or unequally distributed. All variations of charge distribution of the polycationic moiety are encompassed by the present invention.

The lipid "A" and the nonimmunogenic polymer "W" can be attached by various methods and preferably by covalent attachment. Methods known to those of skill in the art can be used for the covalent attachment of "A" and "W." Suitable linkages include, but are not limited to, amide, amine, carboxyl, carbonate, carbamate, ester, and hydrazone linkages. It will be apparent to those skilled in the art that "A" and "W" must have complementary functional groups to effectuate the linkage. The reaction of these two groups, one on the lipid and the other on the polymer, will provide the desired linkage. For example, when the lipid is a diacylglycerol and the terminal hydroxyl is activated, for instance with NHS and DCC, to form an active ester, and is then reacted with a polymer which contains an amino group, such as with a polyamide (see, e.g., U.S. Pat. Nos. 6,320,017 and 6,586,559), an amide bond will form between the two groups.

In certain instances, the polycationic moiety can have a ligand attached, such as a targeting ligand or a chelating moiety for complexing calcium. Preferably, after the ligand is attached, the cationic moiety maintains a positive charge. In certain instances, the ligand that is attached has a positive charge. Suitable ligands include, but are not limited to, a compound or device with a reactive functional group and include lipids, amphipathic lipids, carrier compounds, bioaffinity compounds, biomaterials, biopolymers, biomedical devices, analytically detectable compounds, therapeutically active compounds, enzymes, peptides, proteins, antibodies, immune stimulators, radiolabels, fluorogens, biotin, drugs, haptens, DNA, RNA, polysaccharides, liposomes, virosomes, micelles, immunoglobulins, functional groups, other targeting moieties, or toxins.

The bilayer stabilizing component (e.g., PEG-lipid) typically comprises from about 0 mol % to about 20 mol %, from about 0.5 mol % to about 20 mol %, from about 1.5 mol % to about 18 mol %, from about 4 mol % to about 15 mol %, from about 5 mol % to about 12 mol %, or about 2 mol % of the total lipid present in the particle. One of ordinary skill in the art will appreciate that the concentration of the bilayer stabilizing component can be varied depending on the bilayer stabilizing component employed and the rate at which the nucleic acid-lipid particle is to become fusogenic.

By controlling the composition and concentration of the bilayer stabilizing component, one can control the rate at which the bilayer stabilizing component exchanges out of the nucleic acid-lipid particle and, in turn, the rate at which the nucleic acid-lipid particle becomes fusogenic. For instance, when a polyethyleneglycol-phosphatidylethanolamine conjugate or a polyethyleneglycol-ceramide conjugate is used as the bilayer stabilizing component, the rate at which the nucleic acid-lipid particle becomes fusogenic can be varied, for example, by varying the concentration of the bilayer stabilizing component, by varying the molecular weight of the polyethyleneglycol, or by varying the chain length and degree of saturation of the acyl chain groups on the phosphatidylethanolamine or the ceramide. In addition, other variables including, for example, pH, temperature, ionic strength, etc. can be used to vary and/or control the rate at which the nucleic acid-lipid particle becomes fusogenic. Other methods which can be used to control the rate at which the nucleic acid-lipid particle becomes fusogenic will become apparent to those of skill in the art upon reading this disclosure.

B. Additional Carrier Systems

Non-limiting examples of additional lipid-based carrier systems suitable for use in the present invention include lipoplexes (see, e.g., U.S. Patent Publication No. 20030203865; and Zhang et al., *J. Control Release*, 100:165-180 (2004)), pH-sensitive lipoplexes (see, e.g., U.S. Patent Publication No. 20020192275), reversibly masked lipoplexes (see, e.g., U.S. Patent Publication Nos. 20030180950), cationic lipid-based compositions (see, e.g., U.S. Pat. No. 6,756,054; and U.S. Patent Publication No. 20050234232), cationic liposomes (see, e.g., U.S. Patent Publication Nos. 20030229040, 20020160038, and 20020012998; U.S. Pat. No. 5,908,635; and PCT Publication No. WO 01/72283), anionic liposomes (see, e.g., U.S. Patent Publication No. 20030026831), pH-sensitive liposomes (see, e.g., U.S. Patent Publication No. 20020192274; and AU 2003210303), antibody-coated liposomes (see, e.g., U.S. Patent Publication No. 20030108597; and PCT Publication No. WO 00/50008), cell-type specific liposomes (see, e.g., U.S. Patent Publication No. 20030198664), liposomes containing nucleic acid and peptides (see, e.g., U.S. Pat. No. 6,207,456), liposomes containing lipids derivatized with releasable hydrophilic polymers (see, e.g., U.S. Patent Publication No. 20030031704), lipid-entrapped nucleic acid (see, e.g., PCT Publication Nos. WO 03/057190 and WO 03/059322), lipid-encapsulated nucleic acid (see, e.g., U.S. Patent Publication No. 20030129221; and U.S. Pat. No. 5,756,122), other liposomal compositions (see, e.g., U.S. Patent Publication Nos. 20030035829 and 20030072794; and U.S. Pat. No. 6,200,599), stabilized mixtures of liposomes and emulsions (see, e.g., EP1304160), emulsion compositions (see, e.g., U.S. Pat. No. 6,747,014), and nucleic acid micro-emulsions (see, e.g., U.S. Patent Publication No. 20050037086).

Examples of polymer-based carrier systems suitable for use in the present invention include, but are not limited to, cationic polymer-nucleic acid complexes (i.e., polyplexes). To form a polyplex, a nucleic acid (e.g., siRNA) is typically complexed with a cationic polymer having a linear, branched, star, or dendritic polymeric structure that condenses the nucleic acid into positively charged particles capable of interacting with anionic proteoglycans at the cell surface and entering cells by endocytosis. In some embodiments, the polyplex comprises nucleic acid (e.g., siRNA) complexed with a cationic polymer such as polyethylenimine (PEI) (see, e.g., U.S. Pat. No. 6,013,240; commercially available from Qbiogene, Inc. (Carlsbad, Calif.) as In vivo jetPEI™, a linear form of PEI), polypropylenimine (PPI), polyvinylpyrrolidone (PVP), poly-L-lysine (PLL), diethylaminoethyl (DEAE)-dextran, poly(β-amino ester) (PAE) polymers (see, e.g., Lynn et al., *J. Am. Chem. Soc.*, 123:8155-8156 (2001)), chitosan, polyamidoamine (PAMAM) dendrimers (see, e.g., Kukowska-Latallo et al., *Proc. Natl. Acad. Sci. USA*, 93:4897-4902 (1996)), porphyrin (see, e.g., U.S. Pat. No. 6,620,805), polyvinylether (see, e.g., U.S. Patent Publication No. 20040156909), polycyclic amidinium (see, e.g., U.S. Patent Publication No. 20030220289), other polymers comprising primary amine, imine, guanidine, and/or imidazole groups (see, e.g., U.S. Pat. No. 6,013,240; PCT Publication No. WO/9602655; PCT Publication No. WO95/21931; Zhang et al., *J. Control Release*, 100:165-180 (2004); and Tiera et al., *Curr. Gene Ther.*, 6:59-71 (2006)), and a mixture thereof. In other embodiments, the polyplex comprises cationic polymer-nucleic acid complexes as described in U.S. Patent Publication Nos. 20060211643, 20050222064, 20030125281, and 20030185890, and PCT Publication No. WO 03/066069; biodegradable poly(β-amino ester) polymer-nucleic acid complexes as described in U.S. Patent Publication No. 20040071654; microparticles containing polymeric matrices as described in U.S. Patent Publication No. 20040142475; other microparticle compositions as described in U.S. Patent Publication No. 20030157030; condensed nucleic acid complexes as described in U.S. Patent Publication No. 20050123600; and nanocapsule and microcapsule compositions as described in AU 2002358514 and PCT Publication No. WO 02/096551.

In certain instances, the siRNA molecule may be complexed with cyclodextrin or a polymer thereof. Non-limiting examples of cyclodextrin-based carrier systems include the cyclodextrin-modified polymer-nucleic acid complexes described in U.S. Patent Publication No. 20040087024; the linear cyclodextrin copolymer-nucleic acid complexes described in U.S. Pat. Nos. 6,509,323, 6,884,789, and 7,091,192; and the cyclodextrin polymer-complexing agent-nucleic acid complexes described in U.S. Pat. No. 7,018,609. In certain other instances, the siRNA molecule may be complexed with a peptide or polypeptide. An example of a protein-based carrier system includes, but is not limited to, the cationic oligopeptide-nucleic acid complex described in PCT Publication No. WO95/21931.

V. Preparation of Nucleic Acid-Lipid Particles

The serum-stable nucleic acid-lipid particles of the present invention, in which the siRNA described herein is encapsulated in a lipid bilayer and is protected from degradation, can be formed by any method known in the art including, but not limited to, a continuous mixing method, a direct dilution process, a detergent dialysis method, or a modification of a reverse-phase method which utilizes organic solvents to provide a single phase during mixing of the components.

In preferred embodiments, the cationic lipids are lipids of Formula I and II or combinations thereof. In other preferred embodiments, the non-cationic lipids are egg sphingomyelin (ESM), distearoylphosphatidylcholine (DSPC), dioleoylphosphatidylcholine (DOPC), 1-palmitoyl-2-oleoyl-phosphatidylcholine (POPC), monomethyl-phosphatidylethanolamine, dimethyl-phosphatidylethanolamine, 14:0 PE (1,2-dimyristoyl-phosphatidylethanolamine (DMPE)), 16:0 PE (1,2-dipalmitoyl-phosphatidylethanolamine (DPPE)), 18:0 PE (1,2-distearoyl-phosphatidylethanolamine (DSPE)), 18:1 PE (1,2-dioleoyl-phosphatidylethanolamine (DOPE)), 18:1 trans PE (1,2-dielaidoyl-phosphatidylethanolamine (DEPE)), 18:0-18:1 PE (1-stearoyl-2-oleoyl-phosphatidylethanolamine (SOPE)), 16:0-18:1 PE (1-palmitoyl-2-oleoyl-phosphatidylethanolamine (POPE)), polyethylene glycol-based polymers (e.g., PEG 2000, PEG 5000, PEG-modified diacylglycerols, or PEG-modified dialkyloxypropyls), cholesterol, or combinations thereof. In still other preferred embodiments, the organic solvents are methanol, chloroform, methylene chloride, ethanol, diethyl ether, or combinations thereof.

In a preferred embodiment, the present invention provides for nucleic acid-lipid particles produced via a continuous mixing method, e.g., process that includes providing an aqueous solution comprising a nucleic acid such as an siRNA in a first reservoir, providing an organic lipid solution in a second reservoir, and mixing the aqueous solution with the organic lipid solution such that the organic lipid solution mixes with the aqueous solution so as to substantially instantaneously produce a liposome encapsulating the nucleic acid (e.g., siRNA). This process and the apparatus for carrying this process are described in detail in U.S. Patent Publication No. 20040142025.

The action of continuously introducing lipid and buffer solutions into a mixing environment, such as in a mixing chamber, causes a continuous dilution of the lipid solution with the buffer solution, thereby producing a liposome substantially instantaneously upon mixing. As used herein, the phrase "continuously diluting a lipid solution with a buffer solution" (and variations) generally means that the lipid solution is diluted sufficiently rapidly in a hydration process with sufficient force to effectuate vesicle generation. By mixing the aqueous solution comprising a nucleic acid with the organic lipid solution, the organic lipid solution undergoes a continuous stepwise dilution in the presence of the buffer solution (i.e., aqueous solution) to produce a nucleic acid-lipid particle.

The serum-stable nucleic acid-lipid particles formed using the continuous mixing method typically have a size of from about 50 nm to about 150 nm, from about 60 nm to about 130 nm, from about 70 nm to about 110 nm, or from about 70 nm to about 90 nm. The particles thus formed do not aggregate and are optionally sized to achieve a uniform particle size.

In another embodiment, the present invention provides for nucleic acid-lipid particles produced via a direct dilution process that includes forming a liposome solution and immediately and directly introducing the liposome solution into a collection vessel containing a controlled amount of dilution buffer. In preferred aspects, the collection vessel includes one or more elements configured to stir the contents of the collection vessel to facilitate dilution. In one aspect, the amount of dilution buffer present in the collection vessel is substantially equal to the volume of liposome solution introduced thereto. As a non-limiting example, a liposome solution in 45% ethanol when introduced into the collection vessel containing an equal volume of ethanol will advantageously yield smaller particles in about 22.5%, about 20%, or about 15% ethanol.

In yet another embodiment, the present invention provides for nucleic acid-lipid particles produced via a direct dilution process in which a third reservoir containing dilution buffer is fluidly coupled to a second mixing region. In this embodiment, the liposome solution formed in a first mixing region is immediately and directly mixed with dilution buffer in the second mixing region. In preferred aspects, the second mixing region includes a T-connector arranged so that the liposome solution and the dilution buffer flows meet as opposing 180° flows; however, connectors providing shallower angles can be used, e.g., from about 27° to about 180°. A pump mechanism delivers a controllable flow of buffer to the second mixing region. In one aspect, the flow rate of dilution buffer provided to the second mixing region is controlled to be substantially equal to the flow rate of liposome solution introduced thereto from the first mixing region. This embodiment advantageously allows for more control of the flow of dilution buffer mixing with the liposome solution in the second mixing region, and therefore also the concentration of liposome solution in buffer throughout the second mixing process. Such control of the dilution buffer flow rate advantageously allows for small particle size formation at reduced concentrations.

These processes and the apparatuses for carrying out these direct dilution processes is described in detail in U.S. patent application Ser. No. 11/495,150.

The serum-stable nucleic acid-lipid particles formed using the direct dilution process typically have a size of from about 50 nm to about 150 nm, from about 60 nm to about 130 nm, from about 70 nm to about 110 nm, or from about 70 nm to about 90 nm. The particles thus formed do not aggregate and are optionally sized to achieve a uniform particle size.

In some embodiments, the particles are formed using detergent dialysis. Without intending to be bound by any particular mechanism of formation, a nucleic acid such as an siRNA is contacted with a detergent solution of cationic lipids to form a coated nucleic acid complex. These coated nucleic acids can aggregate and precipitate. However, the presence of a detergent reduces this aggregation and allows the coated nucleic acids to react with excess lipids (typically, non-cationic lipids) to form particles in which the nucleic acid is encapsulated in a lipid bilayer. Thus, the serum-stable nucleic acid-lipid particles can be prepared as follows:

(a) combining a nucleic acid with cationic lipids in a detergent solution to form a coated nucleic acid-lipid complex;

(b) contacting non-cationic lipids with the coated nucleic acid-lipid complex to form a detergent solution comprising a nucleic acid-lipid complex and non-cationic lipids; and (c) dialyzing the detergent solution of step (b) to provide a solution of serum-stable nucleic acid-lipid particles, wherein the nucleic acid is encapsulated in a lipid bilayer and the particles are serum-stable and have a size of from about 50 to about 150 nm.

An initial solution of coated nucleic acid-lipid complexes is formed by combining the nucleic acid with the cationic lipids in a detergent solution. In these embodiments, the detergent solution is preferably an aqueous solution of a neutral detergent having a critical micelle concentration of 15-300 mM, more preferably 20-50 mM. Examples of suitable detergents include, for example, N,N'-((octanoylimino)-bis-(trimethylene))-bis-(D-gluconamide) (BIGCHAP); BRIJ 35; Deoxy-BIGCHAP; dodecylpoly(ethylene glycol) ether; Tween 20; Tween 40; Tween 60; Tween 80; Tween 85; Mega 8; Mega 9; Zwittergent® 3-08; Zwittergent® 3-10; Triton X-405; hexyl-, heptyl-, octyl- and nonyl-β-D-glucopyranoside; and heptylthioglucopyranoside; with octyl β-D-glucopyranoside and Tween-20 being the most preferred. The concentration of detergent in the detergent solution is typically about 100 mM to about 2 M, preferably from about 200 mM to about 1.5 M.

The cationic lipids and nucleic acids will typically be combined to produce a charge ratio (+/−) of about 1:1 to about 20:1, in a ratio of about 1:1 to about 12:1, or in a ratio of about 2:1 to about 6:1. Additionally, the overall concentration of nucleic acid in solution will typically be from about 25 μg/mL to about 1 mg/mL, from about 25 μg/mL to about 200 μg/mL, or from about 50 μg/mL to about 100 μg/mL. The combination of nucleic acids and cationic lipids in detergent solution is kept, typically at room temperature, for a period of time which is sufficient for the coated complexes to form. Alternatively, the nucleic acids and cationic lipids can be combined in the detergent solution and warmed to temperatures of up to about 37° C., about 50° C., about 60° C., or about 70° C. For nucleic acids which are particularly sensitive to temperature, the coated complexes can be formed at lower temperatures, typically down to about 4° C.

In some embodiments, the nucleic acid to lipid ratios (mass/mass ratios) in a formed nucleic acid-lipid particle will range from about 0.01 to about 0.2, from about 0.03 to about 0.1, or from about 0.01 to about 0.08. The ratio of the starting materials also falls within this range. In other embodiments, the nucleic acid-lipid particle preparation uses about 400 μg nucleic acid per 10 mg total lipid or a nucleic acid to lipid ratio of about 0.01 to about 0.08 and, more preferably, about 0.04, which corresponds to 1.25 mg of total lipid per 50 μg of nucleic acid.

The detergent solution of the coated nucleic acid-lipid complexes is then contacted with non-cationic lipids to provide a detergent solution of nucleic acid-lipid complexes and non-cationic lipids. The non-cationic lipids which are useful in this step include, diacylphosphatidylcholine, diacylphosphatidylethanolamine, ceramide, sphingomyelin, cephalin, cardiolipin, and cerebrosides. In preferred embodiments, the non-cationic lipids are diacylphosphatidylcholine, diacylphosphatidylethanolamine, ceramide, or sphingomyelin. The acyl groups in these lipids are preferably acyl groups derived from fatty acids having $C_{10}$-$C_{24}$ carbon chains. More preferably, the acyl groups are lauroyl, myristoyl, palmitoyl, stearoyl, or oleoyl. In particularly preferred embodiments, the non-cationic lipids are DSPC, DOPE, POPC, egg phosphatidylcholine (EPC), cholesterol, or a mixture thereof. In the most preferred embodiments, the nucleic acid-lipid particles are fusogenic particles with enhanced properties in vivo and the non-cationic lipid is DSPC or DOPE. In addition, the nucleic acid-lipid particles of the present invention may further comprise cholesterol. In other preferred embodiments, the non-cationic lipids can further comprise polyethylene glycol-based polymers such as PEG 2,000, PEG 5,000, and PEG conjugated to a diacylglycerol, a ceramide, or a phospholipid, as described in, e.g., U.S. Pat. No. 5,820,873 and U.S. Patent Publication No. 20030077829. In further preferred embodiments, the non-cationic lipids can further comprise polyethylene glycol-based polymers such as PEG 2,000, PEG 5,000, and PEG conjugated to a dialkyloxypropyl.

The amount of non-cationic lipid which is used in the present methods is typically from about 2 to about 20 mg of total lipids to 50 μg of nucleic acid. Preferably, the amount of total lipid is from about 5 to about 10 mg per 50 μg of nucleic acid.

Following formation of the detergent solution of nucleic acid-lipid complexes and non-cationic lipids, the detergent is removed, preferably by dialysis. The removal of the detergent results in the formation of a lipid-bilayer which surrounds the nucleic acid providing serum-stable nucleic acid-lipid particles which have a size of from about 50 nm to about 150 nm, from about 60 nm to about 130 nm, from about 70 nm to about 110 nm, or from about 70 nm to about 90 nm. The particles thus formed do not aggregate and are optionally sized to achieve a uniform particle size.

The serum-stable nucleic acid-lipid particles can be sized by any of the methods available for sizing liposomes. The sizing may be conducted in order to achieve a desired size range and relatively narrow distribution of particle sizes.

Several techniques are available for sizing the particles to a desired size. One sizing method, used for liposomes and equally applicable to the present particles, is described in U.S. Pat. No. 4,737,323. Sonicating a particle suspension either by bath or probe sonication produces a progressive size reduction down to particles of less than about 50 nm in size. Homogenization is another method which relies on shearing energy to fragment larger particles into smaller ones. In a typical homogenization procedure, particles are recirculated through a standard emulsion homogenizer until selected particle sizes, typically between about 60 and about 80 nm, are observed. In both methods, the particle size distribution can be monitored by conventional laser-beam particle size discrimination, or QELS.

Extrusion of the particles through a small-pore polycarbonate membrane or an asymmetric ceramic membrane is also an effective method for reducing particle sizes to a relatively well-defined size distribution. Typically, the suspension is cycled through the membrane one or more times until the desired particle size distribution is achieved. The particles may be extruded through successively smaller-pore membranes, to achieve a gradual reduction in size.

In another group of embodiments, the serum-stable nucleic acid-lipid particles can be prepared as follows:

(a) preparing a mixture comprising cationic lipids and non-cationic lipids in an organic solvent;

(b) contacting an aqueous solution of nucleic acid with the mixture in step (a) to provide a clear single phase; and (c) removing the organic solvent to provide a suspension of nucleic acid-lipid particles, wherein the nucleic acid is encapsulated in a lipid bilayer and the particles are stable in serum and have a size of from about 50 to about 150 nm.

The nucleic acids (e.g., siRNA), cationic lipids, and non-cationic lipids which are useful in this group of embodiments are as described for the detergent dialysis methods above.

The selection of an organic solvent will typically involve consideration of solvent polarity and the ease with which the solvent can be removed at the later stages of particle formation. The organic solvent, which is also used as a solubilizing agent, is in an amount sufficient to provide a clear single phase mixture of nucleic acid and lipids. Suitable solvents include, but are not limited to, chloroform, dichloromethane, diethylether, cyclohexane, cyclopentane, benzene, toluene, methanol, or other aliphatic alcohols such as propanol, isopropanol, butanol, tert-butanol, iso-butanol, pentanol and hexanol. Combinations of two or more solvents may also be used in the present invention.

Contacting the nucleic acid with the organic solution of cationic and non-cationic lipids is accomplished by mixing together a first solution of nucleic acid, which is typically an aqueous solution, and a second organic solution of the lipids. One of skill in the art will understand that this mixing can take place by any number of methods, for example, by mechanical means such as by using vortex mixers.

After the nucleic acid has been contacted with the organic solution of lipids, the organic solvent is removed, thus forming an aqueous suspension of serum-stable nucleic acid-lipid particles. The methods used to remove the organic solvent will typically involve evaporation at reduced pressures or blowing a stream of inert gas (e.g., nitrogen or argon) across the mixture.

The serum-stable nucleic acid-lipid particles thus formed will typically be sized from about 50 nm to about 150 nm, from about 60 nm to about 130 nm, from about 70 nm to about 110 nm, or from about 70 nm to about 90 nm. To achieve further size reduction or homogeneity of size in the particles, sizing can be conducted as described above.

In other embodiments, the methods will further comprise adding non-lipid polycations which are useful to effect the delivery to cells using the present compositions. Examples of suitable non-lipid polycations include, but are limited to, hexadimethrine bromide (sold under the brand name POLYBRENE®, from Aldrich Chemical Co., Milwaukee, Wis., USA) or other salts of heaxadimethrine. Other suitable polycations include, for example, salts of poly-L-ornithine, poly-L-arginine, poly-L-lysine, poly-D-lysine, polyallylamine, and polyethyleneimine.

In certain embodiments, the formation of the nucleic acid-lipid particles can be carried out either in a mono-phase system (e.g., a Bligh and Dyer monophase or similar mixture of aqueous and organic solvents) or in a two-phase system with suitable mixing.

When formation of the complexes is carried out in a mono-phase system, the cationic lipids and nucleic acids are each dissolved in a volume of the mono-phase mixture. Combination of the two solutions provides a single mixture in which the complexes form. Alternatively, the complexes can form in two-phase mixtures in which the cationic lipids bind to the nucleic acid (which is present in the aqueous phase), and "pull" it into the organic phase.

In another embodiment, the serum-stable nucleic acid-lipid particles can be prepared as follows:

(a) contacting nucleic acids with a solution comprising non-cationic lipids and a detergent to form a nucleic acid-lipid mixture;

(b) contacting cationic lipids with the nucleic acid-lipid mixture to neutralize a portion of the negative charge of the nucleic acids and form a charge-neutralized mixture of nucleic acids and lipids; and (c) removing the detergent from the charge-neutralized mixture to provide the nucleic acid-lipid particles in which the nucleic acids are protected from degradation.

In one group of embodiments, the solution of non-cationic lipids and detergent is an aqueous solution. Contacting the nucleic acids with the solution of non-cationic lipids and detergent is typically accomplished by mixing together a first solution of nucleic acids and a second solution of the lipids and detergent. One of skill in the art will understand that this mixing can take place by any number of methods, for example, by mechanical means such as by using vortex mixers. Preferably, the nucleic acid solution is also a detergent solution. The amount of non-cationic lipid which is used in the present method is typically determined based on the amount of cationic lipid used, and is typically of from about 0.2 to about 5 times the amount of cationic lipid, preferably from about 0.5 to about 2 times the amount of cationic lipid used.

In some embodiments, the nucleic acids are precondensed as described in, e.g., U.S. patent application Ser. No. 09/744,103.

The nucleic acid-lipid mixture thus formed is contacted with cationic lipids to neutralize a portion of the negative charge which is associated with the nucleic acids (or other polyanionic materials) present. The amount of cationic lipids used will typically be sufficient to neutralize at least 50% of the negative charge of the nucleic acid. Preferably, the negative charge will be at least 70% neutralized, more preferably at least 90% neutralized. Cationic lipids which are useful in the present invention, include, for example, DLinDMA and DLenDMA. These lipids and related analogs are described in U.S. Patent Publication No. 20060083780.

Contacting the cationic lipids with the nucleic acid-lipid mixture can be accomplished by any of a number of techniques, preferably by mixing together a solution of the cationic lipid and a solution containing the nucleic acid-lipid mixture. Upon mixing the two solutions (or contacting in any other manner), a portion of the negative charge associated with the nucleic acid is neutralized. Nevertheless, the nucleic acid remains in an uncondensed state and acquires hydrophilic characteristics.

After the cationic lipids have been contacted with the nucleic acid-lipid mixture, the detergent (or combination of detergent and organic solvent) is removed, thus forming the nucleic acid-lipid particles. The methods used to remove the detergent will typically involve dialysis. When organic solvents are present, removal is typically accomplished by evaporation at reduced pressures or by blowing a stream of inert gas (e.g., nitrogen or argon) across the mixture.

The particles thus formed will typically be sized from about 50 nm to several microns, about 50 nm to about 150 nm, from about 60 nm to about 130 nm, from about 70 nm to about 110 nm, or from about 70 nm to about 90 nm. To achieve further size reduction or homogeneity of size in the particles, the nucleic acid-lipid particles can be sonicated, filtered, or subjected to other sizing techniques which are used in liposomal formulations and are known to those of skill in the art.

In other embodiments, the methods will further comprise adding non-lipid polycations which are useful to effect the lipofection of cells using the present compositions. Examples of suitable non-lipid polycations include, hexadimethrine bromide (sold under the brandname POLYBRENE®, from Aldrich Chemical Co., Milwaukee, Wis., USA) or other salts of hexadimethrine. Other suitable polycations include, for example, salts of poly-L-ornithine, poly-L-arginine, poly-L-lysine, poly-D-lysine, polyallylamine, and polyethyleneimine. Addition of these salts is preferably after the particles have been formed.

In another aspect, the serum-stable nucleic acid-lipid particles can be prepared as follows:

(a) contacting an amount of cationic lipids with nucleic acids in a solution; the solution comprising from about 15-35% water and about 65-85% organic solvent and the amount of cationic lipids being sufficient to produce a +/−charge ratio of from about 0.85 to about 2.0, to provide a hydrophobic nucleic acid-lipid complex;

(b) contacting the hydrophobic, nucleic acid-lipid complex in solution with non-cationic lipids, to provide a nucleic acid-lipid mixture; and (c) removing the organic solvents from the nucleic acid-lipid mixture to provide nucleic acid-lipid particles in which the nucleic acids are protected from degradation.

The nucleic acids (e.g., siRNA), non-cationic lipids, cationic lipids, and organic solvents which are useful in this aspect of the invention are the same as those described for the methods above which used detergents. In one group of embodiments, the solution of step (a) is a mono-phase. In another group of embodiments, the solution of step (a) is two-phase.

In preferred embodiments, the non-cationic lipids are ESM, DSPC, DOPC, POPC, monomethyl-phosphatidylethanolamine, dimethyl-phosphatidylethanolamine, DMPE, DPPE, DSPE, DOPE, DEPE, SOPE, POPE, PEG-based polymers (e.g., PEG 2000, PEG 5000, PEG-modified diacylglycerols, or PEG-modified dialkyloxypropyls), cholesterol, or combinations thereof. In still other preferred embodiments, the organic solvents are methanol, chloroform, methylene chloride, ethanol, diethyl ether or combinations thereof.

In one embodiment, the nucleic acid is an siRNA as described herein; the cationic lipid is DLindMA, DLenDMA, DODAC, DDAB, DOTMA, DOSPA, DMRIE, DOGS, or combinations thereof; the non-cationic lipid is ESM, DOPE, PEG-DAG, DSPC, DPPE, DMPE, monomethyl-phosphatidylethanolamine, dimethyl-phosphatidylethanolamine, DMPE, DPPE, DSPE, DOPE, DEPE, SOPE, POPE, cholesterol, or combinations thereof (e.g., DSPC and PEG-DAA); and the organic solvent is methanol, chloroform, methylene chloride, ethanol, diethyl ether or combinations thereof.

As above, contacting the nucleic acids with the cationic lipids is typically accomplished by mixing together a first solution of nucleic acids and a second solution of the lipids, preferably by mechanical means such as by using vortex mixers. The resulting mixture contains complexes as described above. These complexes are then converted to particles by the addition of non-cationic lipids and the removal of the organic solvent. The addition of the non-cationic lipids is typically accomplished by simply adding a solution of the non-cationic lipids to the mixture containing the complexes. A reverse addition can also be used. Subsequent removal of organic solvents can be accomplished by methods known to those of skill in the art and also described above.

The amount of non-cationic lipids which is used in this aspect of the invention is typically an amount of from about 0.2 to about 15 times the amount (on a mole basis) of cationic lipids which was used to provide the charge-neutralized nucleic acid-lipid complex. Preferably, the amount is from about 0.5 to about 9 times the amount of cationic lipids used.

In one embodiment, the nucleic acid-lipid particles preparing according to the above-described methods are either net charge neutral or carry an overall charge which provides the particles with greater gene lipofection activity. Preferably, the nucleic acid component of the particles is a nucleic acid which interferes with the production of an undesired protein. In other preferred embodiments, the non-cationic lipid may further comprise cholesterol.

A variety of general methods for making SNALP-CPLs (CPL-containing SNALPs) are discussed herein. Two general techniques include "post-insertion" technique, that is, insertion of a CPL into for example, a pre-formed SNALP, and the "standard" technique, wherein the CPL is included in the lipid mixture during for example, the SNALP formation steps. The post-insertion technique results in SNALPs having CPLs mainly in the external face of the SNALP bilayer membrane, whereas standard techniques provide SNALPs having CPLs on both internal and external faces. The method is especially useful for vesicles made from phospholipids (which can contain cholesterol) and also for vesicles containing PEG-lipids (such as PEG-DAAs and PEG-DAGs). Methods of making SNALP-CPL, are taught, for example, in U.S. Pat. Nos. 5,705,385; 6,586,410; 5,981,501; 6,534,484; and 6,852,334; U.S. Patent Publication No. 20020072121; and PCT Publication No. WO 00/62813.

VI. Kits

The present invention also provides nucleic acid-lipid particles in kit form. The kit may comprise a container which is compartmentalized for holding the various elements of the nucleic acid-lipid particles (e.g., the nucleic acids and the individual lipid components of the particles). In some embodiments, the kit may further comprise an endosomal membrane destabilizer (e.g., calcium ions). The kit typically contains the nucleic acid-lipid particle compositions of the present invention, preferably in dehydrated form, with instructions for their rehydration and administration. In certain instances, the particles and/or compositions comprising the particles may have a targeting moiety attached to the surface of the particle. Methods of attaching targeting moieties (e.g., antibodies, proteins) to lipids (such as those used in the present particles) are known to those of skill in the art.

VII. Administration of Nucleic Acid-Lipid Particles

Once formed, the serum-stable nucleic acid-lipid particles of the present invention are useful for the introduction of nucleic acids (i.e., siRNA that silences expression of a Filovirus gene) into cells. Accordingly, the present invention also provides methods for introducing a nucleic acid (e.g., siRNA and/or plasmid) into a cell. The methods are carried out in vitro or in vivo by first forming the particles as described above and then contacting the particles with the cells for a period of time sufficient for delivery of the nucleic acid to the cells to occur.

The nucleic acid-lipid particles of the present invention can be adsorbed to almost any cell type with which they are mixed or contacted. Once adsorbed, the particles can either be endocytosed by a portion of the cells, exchange lipids with cell membranes, or fuse with the cells. Transfer or incorporation of the nucleic acid portion of the particle can take place via any one of these pathways. In particular, when fusion takes place, the particle membrane is integrated into the cell membrane and the contents of the particle combine with the intracellular fluid.

The nucleic acid-lipid particles of the present invention can be administered either alone or in a mixture with a physiologically-acceptable carrier (such as physiological saline or phosphate buffer) selected in accordance with the route of administration and standard pharmaceutical practice. Generally, normal saline will be employed as the pharmaceutically acceptable carrier. Other suitable carriers include, e.g., water, buffered water, 0.4% saline, 0.3% glycine, and the like, including glycoproteins for enhanced stability, such as albumin, lipoprotein, globulin, etc.

The pharmaceutical carrier is generally added following particle formation. Thus, after the particle is formed, the particle can be diluted into pharmaceutically acceptable carriers such as normal saline.

The concentration of particles in the pharmaceutical formulations can vary widely, i.e., from less than about 0.05%, usually at or at least about 2-5% to as much as 10 to 30% by weight and will be selected primarily by fluid volumes, viscosities, etc., in accordance with the particular mode of administration selected. For example, the concentration may be increased to lower the fluid load associated with treatment. This may be particularly desirable in patients having atherosclerosis-associated congestive heart failure or severe hypertension. Alternatively, particles composed of irritating lipids may be diluted to low concentrations to lessen inflammation at the site of administration.

The pharmaceutical compositions of the present invention may be sterilized by conventional, well known sterilization techniques. Aqueous solutions can be packaged for use or filtered under aseptic conditions and lyophilized, the lyophilized preparation being combined with a sterile aqueous solution prior to administration. The compositions can contain pharmaceutically acceptable auxiliary substances as required to approximate physiological conditions, such as pH adjusting and buffering agents, tonicity adjusting agents and the like, for example, sodium acetate, sodium lactate, sodium chloride, potassium chloride, and calcium chloride. Additionally, the particle suspension may include lipid-protective agents which protect lipids against free-radical and lipid-peroxidative damages on storage. Lipophilic free-radical quenchers, such as alphatocopherol and water-soluble iron-specific chelators, such as ferrioxamine, are suitable.

The nucleic acid-lipid particles can be incorporated into a broad range of topical dosage forms including, but not limited to, gels, oils, emulsions, topical creams, pastes, ointments, lotions, foams, and the like.

A. In vivo administration

Systemic delivery for in vivo therapy, i.e., delivery of a therapeutic nucleic acid to a distal target cell via body systems such as the circulation, has been achieved using nucleic acid-lipid particles such as those disclosed in PCT Publication No. WO 96/40964 and U.S. Pat. Nos. 5,705,385; 5,976,567; 5,981,501; and 6,410,328. This latter format provides a fully encapsulated nucleic acid-lipid particle that protects the nucleic acid from nuclease degradation in serum, is nonimmunogenic, is small in size, and is suitable for repeat dosing.

For in vivo administration, administration can be in any manner known in the art, e.g., by injection, oral administration, inhalation (e.g., intransal or intratracheal), transdermal application, or rectal administration. Administration can be accomplished via single or divided doses. The pharmaceutical compositions can be administered parenterally, i.e., intraarticularly, intravenously, intraperitoneally, subcutaneously, or intramuscularly. In some embodiments, the pharmaceutical compositions are administered intravenously or intraperitoneally by a bolus injection (see, e.g., U.S. Pat. No. 5,286,634). Intracellular nucleic acid delivery has also been discussed in Straubringer et al., *Methods Enzymol.*, 101:512 (1983); Mannino et al., *Biotechniques*, 6:682 (1988); Nicolau et al., *Crit. Rev. Ther. Drug Carrier Syst.*, 6:239 (1989); and Behr, *Acc. Chem. Res.*, 26:274 (1993). Still other methods of administering lipid based therapeutics are described in, for example, U.S. Pat. Nos. 3,993,754; 4,145,410; 4,235,871; 4,224,179; 4,522,803; and 4,588,578. The lipid nucleic acid particles can be administered by direct injection at the site of disease or by injection at a site distal from the site of disease (see, e.g., Culver, HUMAN GENE THERAPY, MaryAnn Liebert, Inc., Publishers, New York. pp. 70-71(1994)).

The compositions of the present invention, either alone or in combination with other suitable components, can be made into aerosol formulations (i.e., they can be "nebulized") to be administered via inhalation (e.g., intranasally or intratracheally) (see, Brigham et al., *Am. J. Sci.*, 298:278 (1989)). Aerosol formulations can be placed into pressurized acceptable propellants, such as dichlorodifluoromethane, propane, nitrogen, and the like.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, compositions can be administered, for example, by intravenous infusion, orally, topically, intraperitoneally, intravesically, or intrathecally.

Formulations suitable for oral administration can consist of: (a) liquid solutions, such as an effective amount of the packaged nucleic acid suspended in diluents such as water, saline, or PEG 400; (b) capsules, sachets, or tablets, each containing a predetermined amount of the active ingredient, as liquids, solids, granules, or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

Generally, when administered intravenously, the nucleic acid-lipid formulations are formulated with a suitable pharmaceutical carrier. Many pharmaceutically acceptable carriers may be employed in the compositions and methods of the present invention. Suitable formulations for use in the present invention are found, for example, in REMINGTON'S PHARMACEUTICAL SCIENCES, Mack Publishing Company, Philadelphia, Pa., 17th ed. (1985). A variety of aqueous carriers may be used, for example, water, buffered water, 0.4% saline, 0.3% glycine, and the like, and may include glycoproteins for enhanced stability, such as albumin, lipoprotein, globulin, etc. Generally, normal buffered saline (135-150 mM NaCl) will be employed as the pharmaceutically acceptable carrier, but other suitable carriers will suffice. These compositions can be sterilized by conventional liposomal sterilization techniques, such as filtration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc. These compositions can be sterilized using the techniques referred to above or, alternatively, they can be produced under sterile conditions. The resulting aqueous solutions may be packaged for use or filtered under aseptic conditions and lyophilized, the lyophilized preparation being combined with a sterile aqueous solution prior to administration.

When preparing pharmaceutical preparations of the nucleic acid-lipid particles of the invention, it is preferable to use quantities of the particles which have been purified to reduce or eliminate empty particles or particles with nucleic acid associated with the external surface.

The methods of the present invention may be practiced in a variety of hosts. Preferred hosts include mammalian species, such as avian (e.g., ducks), primates (e.g., humans and chimpanzees as well as other nonhuman primates), canines, felines, equines, bovines, ovines, caprines, rodents (e.g., rats and mice), lagomorphs, and swine.

The amount of particles administered will depend upon the ratio of nucleic acid to lipid, the particular nucleic acid used, the disease state being diagnosed, the age, weight, and condition of the patient, and the judgment of the clinician, but will generally be between about 0.01 and about 50 mg per kilogram of body weight, preferably between about 0.1 and about 5 mg/kg of body weight, or about $10^8$-$10^{10}$ particles per injection.

B. Cells for delivery of interfering RNA

The compositions and methods of the present invention are used to treat a wide variety of cell types, in vivo and in vitro. Suitable cells include, e.g., hematopoietic precursor (stem) cells, fibroblasts, keratinocytes, hepatocytes, endothelial cells, skeletal and smooth muscle cells, osteoblasts, neurons, quiescent lymphocytes, terminally differentiated cells, slow or noncycling primary cells, parenchymal cells, lymphoid cells, epithelial cells, bone cells, and the like.

In vivo delivery of nucleic acid-lipid particles encapsulating an interfering RNA is suited for targeting cells of any cell type. The methods and compositions can be employed with cells of a wide variety of vertebrates, including mammals, such as, e.g, canines, felines, equines, bovines, ovines, caprines, rodents (e.g., mice, rats, and guinea pigs), lagomorphs, swine, and primates (e.g. monkeys, chimpanzees, and humans).

To the extent that tissue culture of cells may be required, it is well known in the art. For example, Freshney, Culture of Animal Cells, a Manual of Basic Technique, 3rd Ed., Wiley-Liss, New York (1994), Kuchler et al., Biochemical Methods in Cell Culture and Virology, Dowden, Hutchinson and Ross, Inc. (1977), and the references cited therein provide a general guide to the culture of cells. Cultured cell systems often will be in the form of monolayers of cells, although cell suspensions are also used.

C. Detection of SNALPs

In some embodiments, the nucleic acid-lipid particles are detectable in the subject at about 8, 12, 24, 48, 60, 72, or 96 hours, or 6, 8, 10, 12, 14, 16, 18, 19, 22, 24, 25, or 28 days after administration of the particles. The presence of the particles can be detected in the cells, tissues, or other biological samples from the subject. The particles may be detected, e.g., by direct detection of the particles, detection of the interfering RNA sequence, detection of the target sequence of interest (i.e., by detecting expression or reduced expression of the Filovirus sequence of interest), detection of a compound modulated by a Filovirus protein (e.g., interferon), detection of viral load in the subject, or a combination thereof.

1. Detection of Particles

Nucleic acid-lipid particles can be detected using any methods known in the art. For example, a label can be coupled directly or indirectly to a component of the SNALP or other lipid-based carrier system using methods well known in the art. A wide variety of labels can be used, with the choice of label depending on sensitivity required, ease of conjugation with the SNALP component, stability requirements, and available instrumentation and disposal provisions. Suitable labels include, but are not limited to, spectral labels such as fluorescent dyes (e.g., fluorescein and derivatives, such as fluorescein isothiocyanate (FITC) and Oregon Green™; rhodamine and derivatives such Texas red, tetrarhodimine isothiocynate (TRITC), etc., digoxigenin, biotin, phycoerythrin, AMCA, CyDyes™, and the like; radiolabels such as $^3H$, $^{125}I$, $^{35}S$, $^{14}C$, $^{32}P$, $^{33}P$, etc.; enzymes such as horse radish peroxidase, alkaline phosphatase, etc.; spectral colorimetric labels such as colloidal gold or colored glass or plastic beads such as polystyrene, polypropylene, latex, etc. The label can be detected using any means known in the art.

2. Detection of Nucleic Acids

Nucleic acids (i.e., siRNA that silence expression of a Filovirus gene) are detected and quantified herein by any of a number of means well known to those of skill in the art. The detection of nucleic acids proceeds by well known methods such as Southern analysis, Northern analysis, gel electrophoresis, PCR, radiolabeling, scintillation counting, and affinity chromatography. Additional analytic biochemical methods such as spectrophotometry, radiography, electrophoresis, capillary electrophoresis, high performance liquid chromatography (HPLC), thin layer chromatography (TLC), and hyperdiffusion chromatography may also be employed.

The selection of a nucleic acid hybridization format is not critical. A variety of nucleic acid hybridization formats are known to those skilled in the art. For example, common formats include sandwich assays and competition or displacement assays. Hybridization techniques are generally described in, e.g., "Nucleic Acid Hybridization, A Practical Approach," Eds. Hames and Higgins, IRL Press (1985).

The sensitivity of the hybridization assays may be enhanced through use of a nucleic acid amplification system which multiplies the target nucleic acid being detected. In vitro amplification techniques suitable for amplifying sequences for use as molecular probes or for generating nucleic acid fragments for subsequent subcloning are known. Examples of techniques sufficient to direct persons of skill through such in vitro amplification methods, including the polymerase chain reaction (PCR) the ligase chain reaction (LCR), Qβ-replicase amplification and other RNA polymerase mediated techniques (e.g., NASBA®) are found in Sambrook et al., In *Molecular Cloning: A Laboratory Manual*, Cold Spring Harbor Laboratory Press (2000); and Ausubel et al., SHORT PROTOCOLS IN MOLECULAR BIOLOGY, eds., Current Protocols, Greene Publishing Associates, Inc. and John Wiley & Sons, Inc. (2002); as well as U.S. Pat. No. 4,683,202; PCR Protocols, A Guide to Methods and Applications (Innis et al. eds.) Academic Press Inc. San Diego, Calif. (1990); Arnheim & Levinson (Oct. 1, 1990), *C&EN*36; *The Journal Of NIH Research,* 3:81 (1991); Kwoh et al., *Proc. Natl. Acad. Sci. USA,* 86:1173 (1989); Guatelli et al., *Proc. Natl. Acad. Sci. USA,* 87:1874 (1990); Lomell et al., *J. Clin. Chem.,* 35:1826 (1989); Landegren et al., *Science,* 241:1077 (1988); Van Brunt, *Biotechnology,* 8:291 (1990); Wu and Wallace, *Gene,* 4:560 (1989); Barringer et al., *Gene,* 89:117 (1990); and Sooknanan and Malek, *Biotechnology,* 13:563 (1995). Improved methods of cloning in vitro amplified nucleic acids are described in U.S. Pat. No. 5,426,039. Other methods described in the art are the nucleic acid sequence based amplification (NASBA®, Cangene, Mississauga, Ontario) and Q Beta Replicase systems. These systems can be used to directly identify mutants where the PCR or LCR primers are designed to be extended or ligated only when a select sequence is present. Alternatively, the select sequences can be generally amplified using, for example, nonspecific PCR primers and the amplified target region later probed for a specific sequence indicative of a mutation.

Oligonucleotides for use as probes, e.g., in in vitro amplification methods, for use as gene probes, or as inhibitor components are typically synthesized chemically according to the solid phase phosphoramidite triester method described by Beaucage and Caruthers, *Tetrahedron Letts.,* 22(20):1859 1862 (1981), e.g., using an automated synthesizer, as described in Needham VanDevanter et al., *Nucleic Acids Res.,* 12:6159 (1984). Purification of oligonucleotides, where necessary, is typically performed by either native acrylamide gel electrophoresis or by anion exchange HPLC as described in Pearson and Regnier, *J. Chrom.,* 255:137 149 (1983). The sequence of the synthetic oligonucleotides can be verified using the chemical degradation method of Maxam and Gilbert (1980) in Grossman and Moldave (eds.) Academic Press, New York, *Methods in Enzymology,* 65:499.

An alternative means for determining the level of transcription is in situ hybridization. In situ hybridization assays are well known and are generally described in Angerer et al., *Methods Enzymol.,* 152:649 (1987). In an in situ hybridization assay cells are fixed to a solid support, typically a glass slide. If DNA is to be probed, the cells are denatured with heat or alkali. The cells are then contacted with a hybridization solution at a moderate temperature to permit annealing of specific probes that are labeled. The probes are preferably labeled with radioisotopes or fluorescent reporters.

D. Detection of an Immune Response

An immune response induced by the siRNA (i.e., siRNA that silences expression of a Filovirus gene) described herein can be long-lived and can be detected long after administration of the siRNA or nucleic acid-lipid particles containing the siRNA. An immune response to the siRNA can be detected by using immunoassays that detect the presence or absence of cytokines and growth factors e.g., produced by responder cells.

Suitable immunoassays include the double monoclonal antibody sandwich immunoassay technique of David et al. (U.S. Pat. No. 4,376,110); monoclonal-polyclonal antibody sandwich assays (Wide et al., in Kirkham and Hunter, eds., *Radioimmunoassay Methods*, E. and S. Livingstone, Edinburgh (1970)); the "Western blot" method of Gordon et al. (U.S. Pat. No. 4,452,901); immunoprecipitation of labeled ligand (Brown et al., *J. Biol. Chem.* 255:4980-4983 (1980)); enzyme-linked immunosorbent assays (ELISA) as described, for example, by Raines et al., *J. Biol. Chem.,* 257:5154-5160 (1982); immunocytochemical techniques, including the use of fluorochromes (Brooks et al., *Clin. Exp. Immunol.,* 39:477 (1980)); and neutralization of activity (Bowen-Pope et al., *Proc. Natl. Acad. Sci. USA,* 81:2396-2400 (1984)). In addition to the immunoassays described above, a number of other immunoassays are available, including those described in U.S. Pat. Nos. 3,817,827; 3,850,752; 3,901,654; 3,935,074; 3,984,533; 3,996,345; 4,034,074; and 4,098,876.

Monoclonal antibodies that specifically bind cytokines and growth factors (e.g., IL-6, IL-12, TNF-α, IFN-α, and IFN-γ can be generated using methods known in the art (see, e.g., Kohler and Milstein, *Nature,* 256: 495-497 (1975); and Harlow and Lane, ANTIBODIES, A LABORATORY MANUAL, Cold Spring Harbor Publication, New York (1999)). Generation of monoclonal antibodies has been previously described and can be accomplished by any means known in the art (see, e.g., Buhring et al., in Hybridoma, Vol. 10, No. 1, pp. 77-78 (1991)). For example, an animal such as a guinea pig or rat, preferably a mouse, is immunized with an immunogenic polypeptide, the antibody-producing cells, preferably splenic lymphocytes, are collected and fused to a stable, immortalized cell line, preferably a myeloma cell line, to produce hybridoma cells which are then isolated and cloned. See, e.g., U.S. Pat. No. 6,156,882. In some methods, the monoclonal antibody is labeled to facilitate detection.

E. Detection of Filovirus Load

Filovirus load can be detected using any means known in the art. Typically, filovirus load is detected in a biological sample from the subject. For example, viral load in the subject's blood can be detected by measuring Filovirus antigens using an immunoassay such as an ELISA (see, e.g., Meissner et al., *Virology*, 300:236-43 (2002); and Ksiazek et al., *J. Clin. Microbiol.*, 30:947-950 (1992)). Viral load can also be detected by amplifying Filovirus nucleic acids (see, e.g., Drosten et al., *J. Clin. Microbiol.*, 40: 2323-2330 (2002)) or by conventional plaque assay using monolayers of Vero or Vero E6 cells (see, e.g., Jahrling, Filoviruses and Arenaviruses, In *Manual of Clinical Microbiology*, Eds. Baron, Pfaller, Tenover, and Yolken, ASM Press, Washington, D.C. (1999)).

VIII. Examples

The present invention will be described in greater detail by way of the following examples. The following examples are offered for illustrative purposes, and are not intended to limit the present invention in any manner. Those of skill in the art will readily recognize a variety of noncritical parameters which can be changed or modified to yield essentially the same results.

Example 1

Materials and Methods siRNA: All siRNA used in these studies were chemically synthesized by Dharmacon Inc. (Chicago, Ill.) or Trilink Biotechnologies, Inc. (San Diego, Calif.) and received as desalted, pre-annealed duplexes.

Lipid Encapsulation of siRNA: Unless otherwise indicated, siRNAs were encapsulated into liposomes composed of the following lipids: synthetic cholesterol (Sigma; St. Louis, Mo.), the phospholipid DSPC (1,2-distearoyl-sn-glycero-3-phosphocholine; Avanti Polar Lipids; Alabaster, Ala.), the PEG-lipid PEG-cDMA (3-N-[(-Methoxy poly(ethylene glycol)2000)carbamoyl]-1,2-dimyrestyloxy-propylamine), and the cationic lipid DLinDMA (1,2-Dilinoleyloxy-3-(N,N-dimethyl)aminopropane) in the molar ratio 48:20:2:30. The resulting SNALPs were dialyzed in PBS and filter sterilized through a 0.2 μm filter prior to use. Particle sizes ranged from 71 to 84 nm and typically 90-95% of the siRNA was found to be encapsulated within the liposome. For vehicle controls, empty liposomes with identical lipid composition were formed in the absence of siRNA.

Cell culture studies: siRNAs (60 pmol) were transfected into Vero cells using Oligofectamine (Invitrogen; Carlsbad, Calif.) according to the manufacturer's instructions. At 0, 24, or 48 hours after transfection, cultures were infected with Ebola-Zaire at a MOI of 1.0. Culture fluids were collected at 24, 48, and 96 hours for determination of infectious Ebola-Zaire, and Vero cells were collected for immunofluorescence staining.

Polyplex treatment and Ebola challenge of guinea pigs: Strain 13 guinea pigs were bred at the U.S. Army Medical Research Institute of Infectious Diseases (USAMRIID). siRNAs (30 nmol ttal) were mixed with In vivo jetPEI® (Qbiogene, Inc.; Carlsbad, Calif.) according to the manufacturer's instructions at an N/P ratio of 5 at room temperature for 20 min. Guinea pigs were treated intravenously with 300 μl of the In vivo jetPEI® polyplexes, corresponding to 8 mg/kg siRNA, by retroorbital injection. Three hours after treatment, guinea pigs were challenged by subcutaneous injection with 1,000 plaque forming units (pfu) of guinea pig-adapted Ebola-Zaire. The guinea pigs received additional treatments of the In vivo jetPEI® polyplexes at 24, 48, and 96 hours after the Ebola-Zaire challenge. Blood was collected by cardiac puncture and processed as plasma for analysis of viremia.

SNALP treatment and Ebola challenge of guinea pigs: SNALP-formulated siRNAs were administered intravenously at a concentration of 1 mg/ml in PBS by retroorbital injection 1 hour after challenge of strain 13 guinea pigs by subcutaneous injection with 1000 pfu of guinea pig-adapted Ebola-Zaire. The guinea pigs received additional treatments of the SNALP-formulated siRNAs at 24, 48, 72, 96, 120, and 144 hours after the Ebola-Zaire challenge. Blood was collected by cardiac puncture and processed as plasma for analysis of viremia. Animals were carefully monitored for signs of disease and survival during the time course of the study.

In vivo cytokine induction: 6-8 week old CD1 ICR mice were obtained from Harlan (Indianapolis, Ind.) and subject to a three week quarantine and acclimation period prior to use. siRNA and lipid formulations were administered as a single intravenous injection in the lateral tail vein in 0.2 ml PBS. Injections were administered over a period of 3-5 seconds. Blood was collected by cardiac puncture 6 hours after administration and processed as plasma for cytokine analysis. Mouse IFN-α and IFN-β were quantified using sandwich ELISA kits (PBL Biomedical; Piscataway, N.J.).

Immunofluorescence Assay: Cells were fixed with 10% neutral-buffered formalin for 24 hours to inactivate infectious Ebola-Zaire. After fixation, cells were washed with copious amounts of PBS and processed for immunofluorescence staining for viral proteins. Briefly, cells were incubated in Ready to Use Proteinase K (Dako; Carpinteria, Calif.) at room temperature for 10 min. Cells were washed in PBS and blocked in normal goat serum (KPL Laboratories; Gaithursburg, Md.) for 20 min at room temperature. Viral antigen was detected by incubating cells in a mouse monoclonal antibody against the guinea pig-adapted Ebola-Zaire for 20 min at room temperature, rinsed in PBS, and incubated with an anti-mouse Alexa Flour® 488 conjugate (Invitrogen Corp.; Carlsbad, Calif.) for 20 min at room temperature. Nuclei were counterstained with DAPI to aid in visualization. Percentage of antigen-positive cells was determined by examining random fields for fluorescence.

Example 2

Selection of Candidate L-pol VP24 VP30 VP35 and NP siRNA

Candidate L-pol, VP24, VP30, VP35, and NP sequences were identified by scanning the sequence to identify AA dinucleotide motifs and the 19 nucleotides 3' of the motif. The following candidate sequences were eliminated: (1) sequences comprising a stretch of 4 or more of the same base in a row; (2) sequences comprising homopolymers of Gs; (3) sequences comprising triple base motifs (GGG, CCC, AAA, or TTT); (4) sequences comprising stretches of 7 or more G/Cs in a row; and (5) sequences comprising direct repeats of 4 or more bases resulting in internal fold-back structures.

Reynold's Rational Design criteria was then applied to the remaining candidate sequences to identify sequences with:
1. 30%-52% GC content;
2. At least 3 A/Us at positions 15-19 (sense);
3. Absence of internal repeats;
4. A at position 19 (sense);
5. A at position 3 (sense);
6. U at position 10 (sense);
7. No G/C at position 19 (sense); and
8. No G at position 13 (sense).

Next, the following criteria were removed to identify additional candidate sequences of interest: 30-52% GC; the requirement for a AA leader sequence; and triplet motifs. BLASTn was used to identify sequences that do not cross-hybridize in humans. The candidate sequences are shown in Tables 1-13. Additional siRNA sequences that target Ebola virus or Marburg virus gene expression are shown in Tables 14-15.

Lengthy table referenced here

US07838658-20101123-T00001

Please refer to the end of the specification for access instructions.

Lengthy table referenced here

US07838658-20101123-T00002

Please refer to the end of the specification for access instructions.

Lengthy table referenced here

US07838658-20101123-T00003

Please refer to the end of the specification for access instructions.

Lengthy table referenced here

US07838658-20101123-T00004

Please refer to the end of the specification for access instructions.

Lengthy table referenced here

US07838658-20101123-T00005

Please refer to the end of the specification for access instructions.

Lengthy table referenced here

US07838658-20101123-T00006

Please refer to the end of the specification for access instructions.

Lengthy table referenced here

US07838658-20101123-T00007

Please refer to the end of the specification for access instructions.

Lengthy table referenced here

US07838658-20101123-T00008

Please refer to the end of the specification for access instructions.

Lengthy table referenced here

US07838658-20101123-T00009

Please refer to the end of the specification for access instructions.

Lengthy table referenced here

US07838658-20101123-T00010

Please refer to the end of the specification for access instructions.

Lengthy table referenced here

US07838658-20101123-T00011

Please refer to the end of the specification for access instructions.

Lengthy table referenced here

US07838658-20101123-T00012

Please refer to the end of the specification for access instructions.

Lengthy table referenced here

US07838658-20101123-T00013

Please refer to the end of the specification for access instructions.

Lengthy table referenced here

US07838658-20101123-T00014

Please refer to the end of the specification for access instructions.

Lengthy table referenced here

US07838658-20101123-T00015

Please refer to the end of the specification for access instructions.

Example 3

Uptake Properties of siRNA

Cy3-labeled siRNA complexed with cationic lipid-containing liposomes was administered to mice intravenously through their tail vein. Cell nuclei were counterstained with DAPI. The siRNA was taken up by Kupfer cells and resident liver macrophages.

Example 4 siRNA Targeting Ebola L-pol Inhibits Ebola Virus Replication In Vitro

Figure 2:
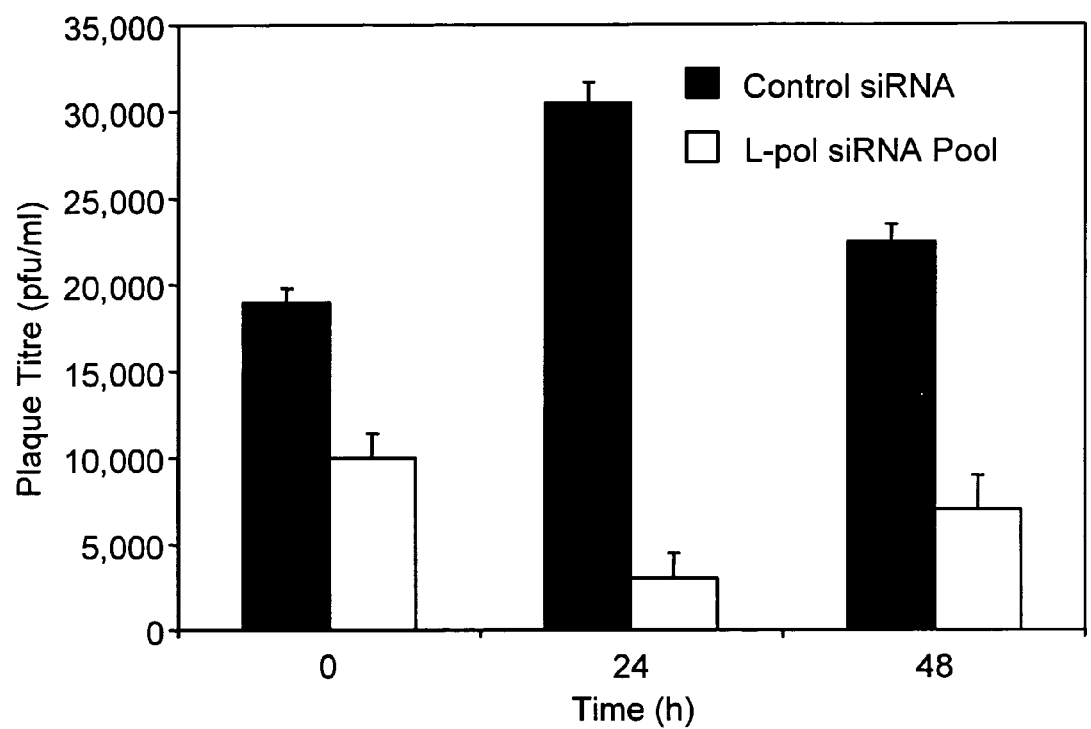
FIG. 2 illustrates data demonstrating that the production of Ebola virus progeny was inhibited in Vero cells transfected with siRNA targeting Ebola L-pol as determined by plaque assay.
Figure 3:
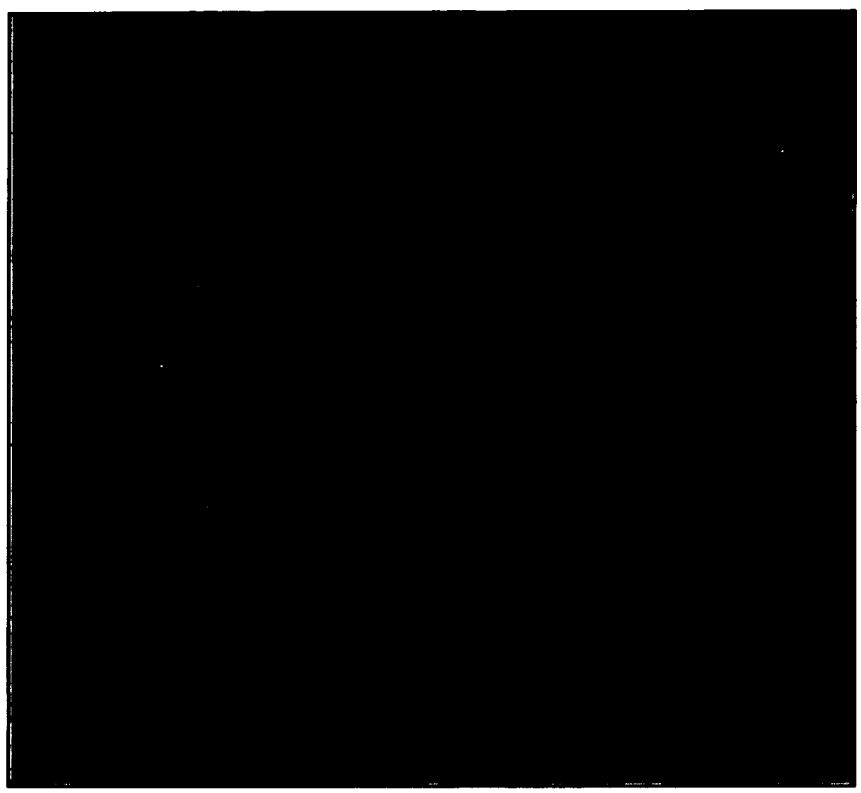
FIG. 3 illustrates data demonstrating that the production of Ebola virus progeny was inhibited in Vero cells transfected with siRNA targeting Ebola L-pol as determined by immunofluorescence antibody staining.
Figure 3:
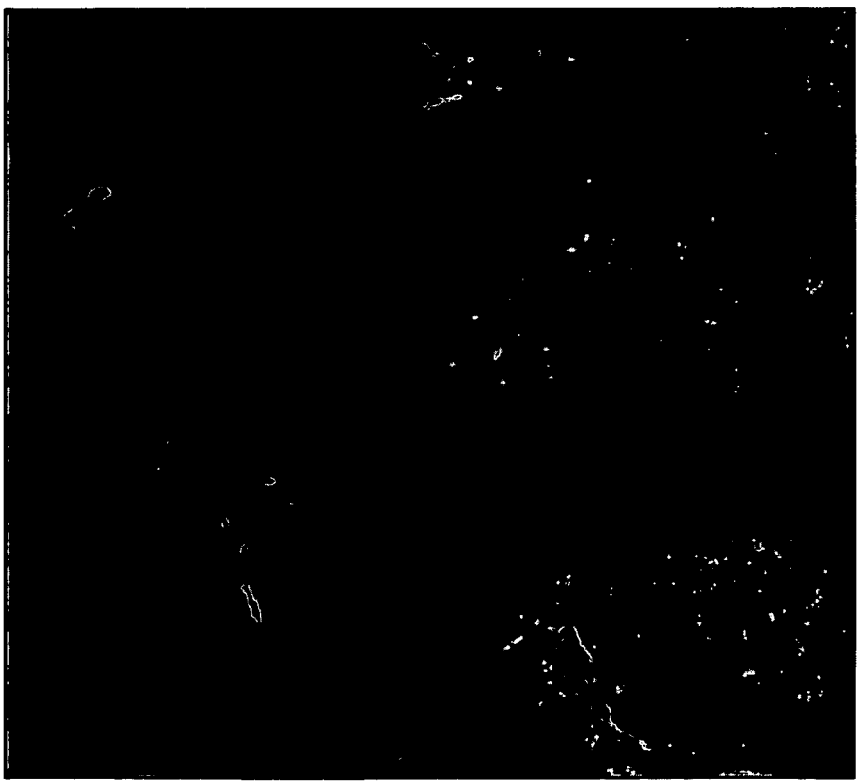

A pool of siRNAs targeting Ebola-Zaire L-pol was complexed with cationic-lipid containing liposomes to form lipoplexes and contacted with Vero cells. The siRNAs had the following sequences: EK1, EK2, EK3, and EK4 (see, Table 1). At various time points after transfection (0, 24, or 48 hours), the transfected cells were infected with Ebola-Zaire at an MOI of 1.0. Cells and culture fluids were harvested 24 hours later to determine virus production. FIG. 2 shows that the siRNA pool inhibited the production of infectious Ebola-Zaire by 2-fold to 10-fold, depending on when the transfected cells were infected. FIG. 3 shows that an 83±14% (P=0.006, Student's T-test) reduction in the number of cells expressing Ebola virus protein was demonstrated by immunofluorescence antibody staining. Individual testing of the four siRNAs targeting Ebola-Zaire L-pol yielded similar results. Thus, lipoplexes containing siRNA targeting Ebola-Zaire L-pol inhibited Ebola replication in vitro.

Example 5 siRNA Targeting Ebola L-pol Reduces Viral Load In Vivo

Figure 4:
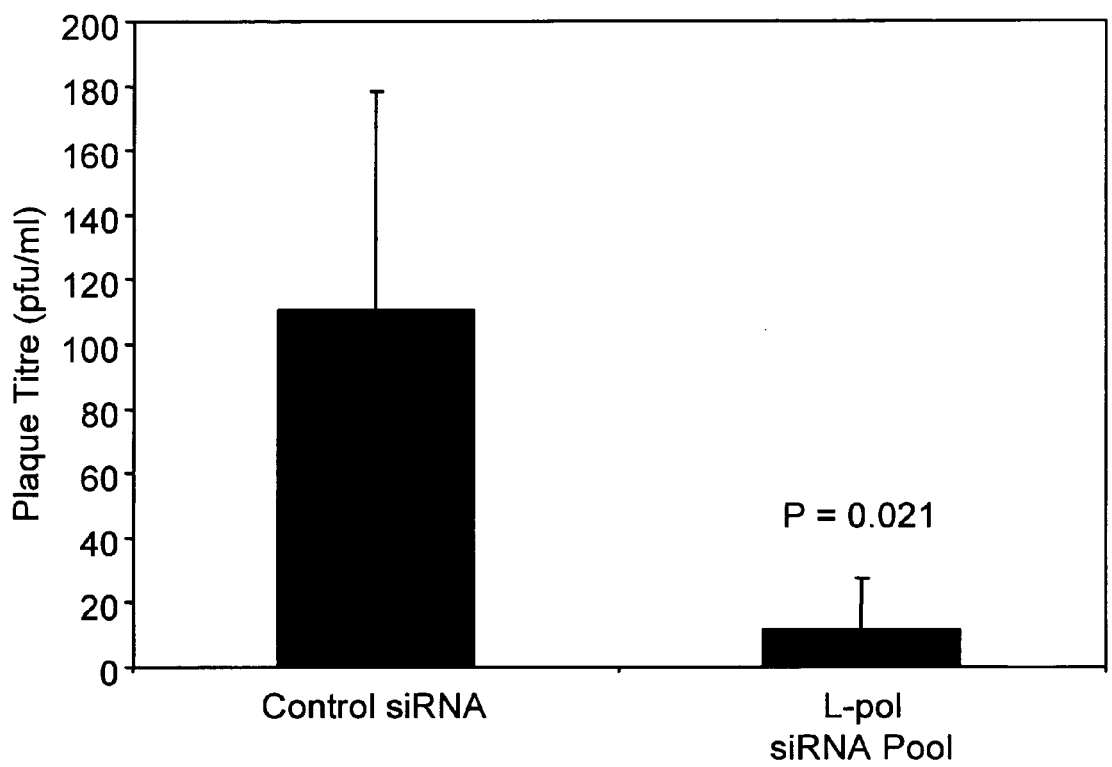
FIG. 4 illustrates data demonstrating that guinea pigs treated with siRNA targeting Ebola L-pol complexed with PEI had a reduced viral load in their plasma.

Guinea pigs were treated with either the pool of siRNAs targeting Ebola-Zaire L-pol (i.e., EK1, EK2, EK3, and EK4) (5 animals) or an irrelevant scrambled siRNA sequence (5 animals). The siRNAs were complexed with polyethylenimine (PEI) to form polyplexes and injected retroorbitally 3 hours before challenge with 1,000 pfu of Ebola-Zaire. Animals received equivalent doses of siRNAs (8 mg/kg) at 24, 48, and 96 hours after Ebola-Zaire challenge. FIG. 4 shows that a significant reduction in plasma viremia (P=0.021) was demonstrated at day 4 after Ebola-Zaire challenge in the animals receiving the pool of siRNAs targeting Ebola-Zaire L-pol compared to those given the control siRNA sequence. In fact, the L-pol siRNA pool reduced viral load by over 80%.

Example 6

Figure 5:
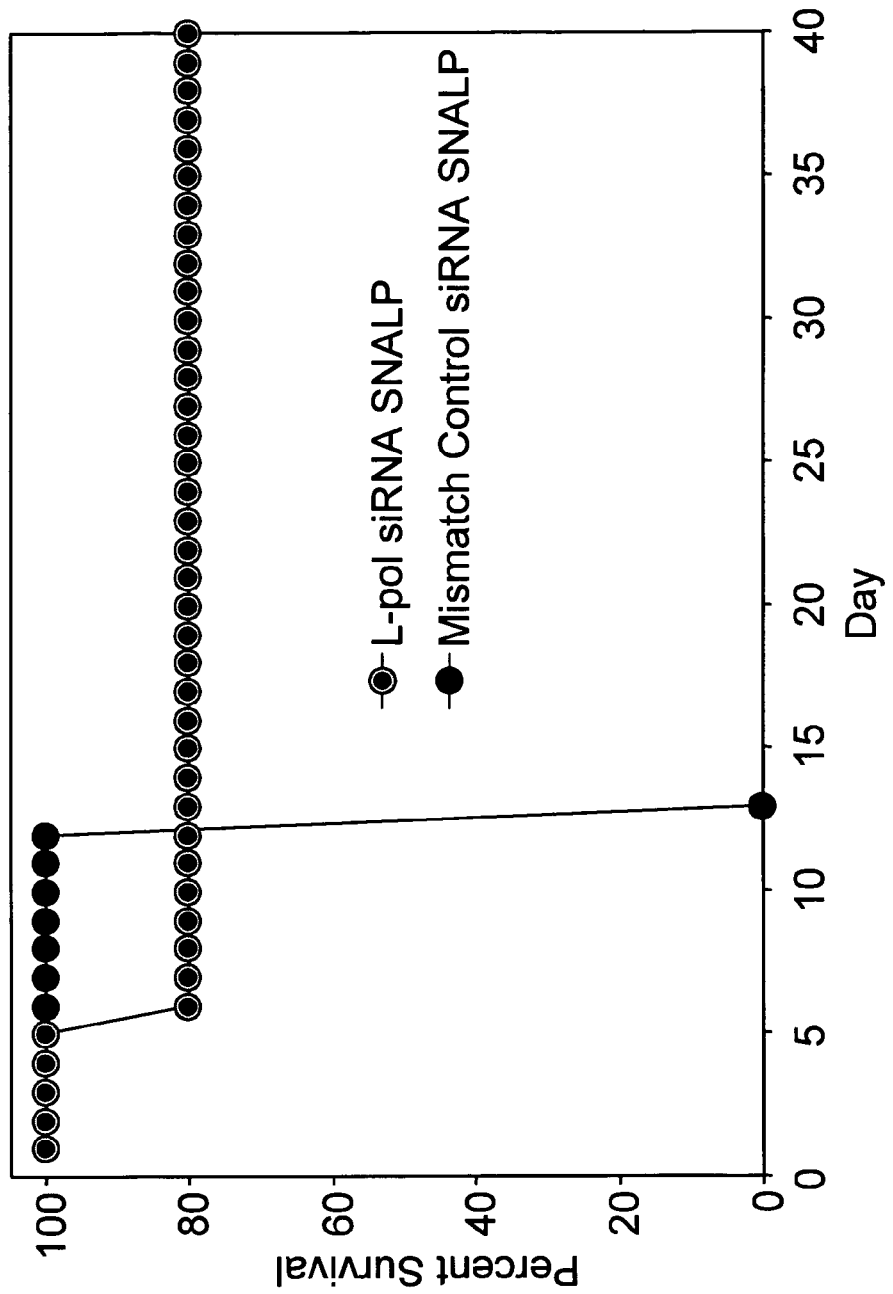
FIG. 5 illustrates data demonstrating that administration of 4 doses of SNALP encapsulating 1 mg/kg siRNA targeting Ebola L-pol protected guinea pigs challenged with a lethal dose of Ebola virus.

SNALP Encapsulating siRNA Targeting Ebola L-pol Protect from Ebola Challenge Guinea pigs were challenged with 1,000 pfu of infectious Ebola-Zaire. One hour following viral challenge, SNALP (DLinDMA:PEG-cDMA:DSPC:Chol in the molar ratio 30:2:20:48) encapsulating a cocktail of siRNA targeting Ebola-Zaire L-pol (i.e., EK1, EK2, EK3, and EK4) were administered to the guinea pigs retroorbitally once per day for 4 days at a dose of 1 mg siRNA per kg. FIG. 5 shows that 80% of the guinea pigs receiving SNALP encapsulating siRNA targeting Ebola-Zaire L-pol survived beyond 40 days, while none of the control animals survived past 14 days. Plasma viremia levels were not detected at day 7 in any of the animals treated with the L-pol siRNA pool, but ranged from about 3.5 to 4.5 log10 pfu/ml in the control animals.

Example 7

Figure 6:
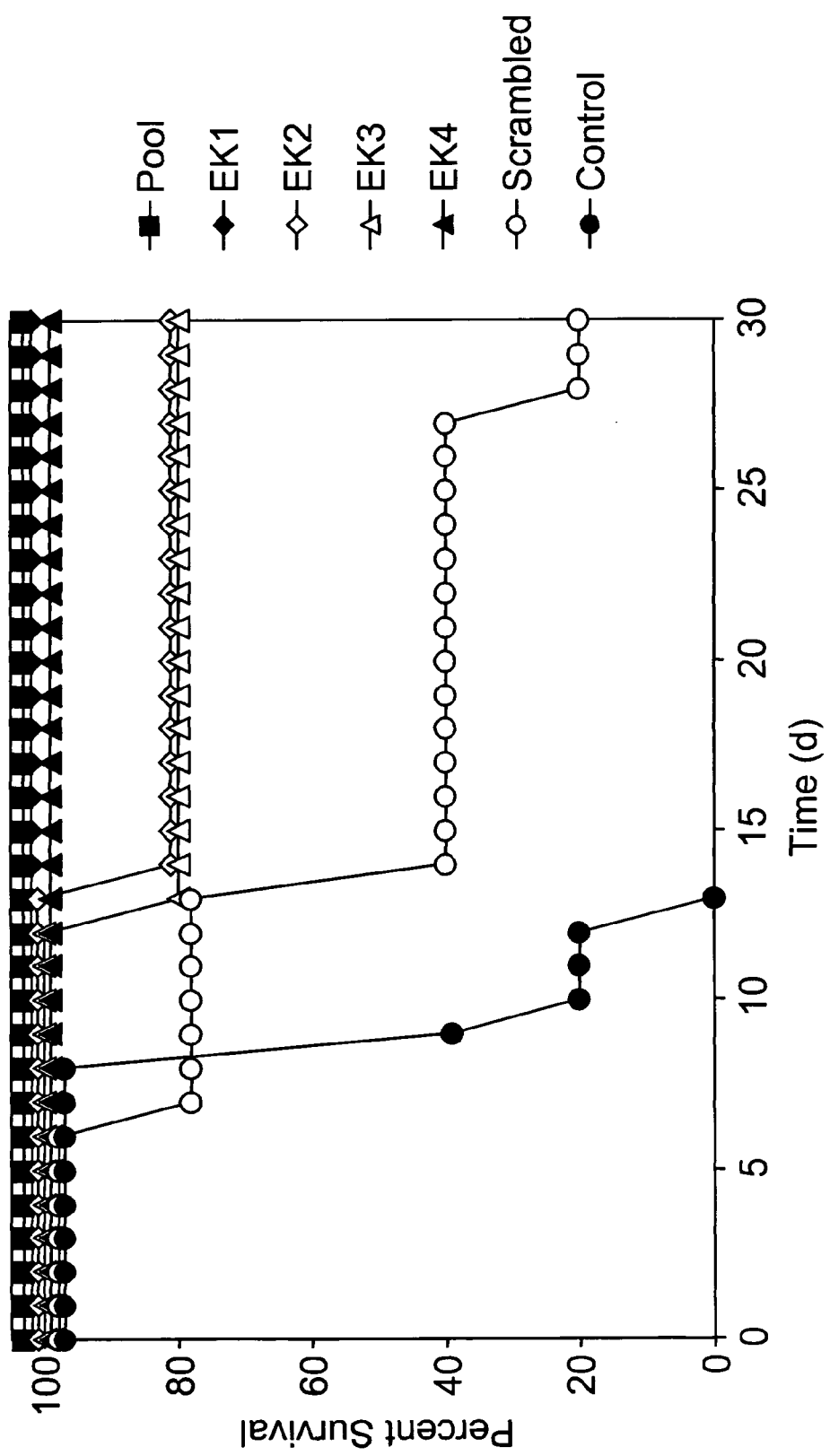
FIG. 6 illustrates data demonstrating that administration of 6 doses of SNALP encapsulating 0.75 mg/kg siRNA targeting Ebola L-pol protected guinea pigs challenged with a lethal dose of Ebola virus.

SNALP Encapsulating siRNA Targeting Ebola L-pol Protect from Ebola Challenge Guinea pigs were challenged with 1,000 pfu of infectious Ebola-Zaire. One hour following viral challenge, SNALP (DLinDMA:PEG-cDMA:DSPC:Chol in the molar ratio 30:2:20:48) encapsulating either individual siRNA targeting Ebola-Zaire L-pol (i.e., EK1, EK2, EK3, or EK4) or a pool of siRNA targeting Ebola-Zaire L-pol (i.e., EK1, EK2, EK3, and EK4) were administered once per day for 6 days to the guinea pigs retroorbitally at a dose of 0.75 mg siRNA per kg. PBS or SNALP encapsulating scrambled siRNA sequences was administered to control animals. FIG. 6 shows that 100% of the guinea pigs that received SNALP encapsulating EK1 or EK4 or the siRNA pool containing EK1, EK2, EK3, and EK4 survived beyond 30 days, 80% of the guinea pigs that received SNALP encapsulating EK2 or EK3 survived beyond 30 days, while none of the control animals that received PBS survived past 14 days and only 20% of the control animals that received scrambled siRNA survived past 30 days.

Example 8

Figure 7:
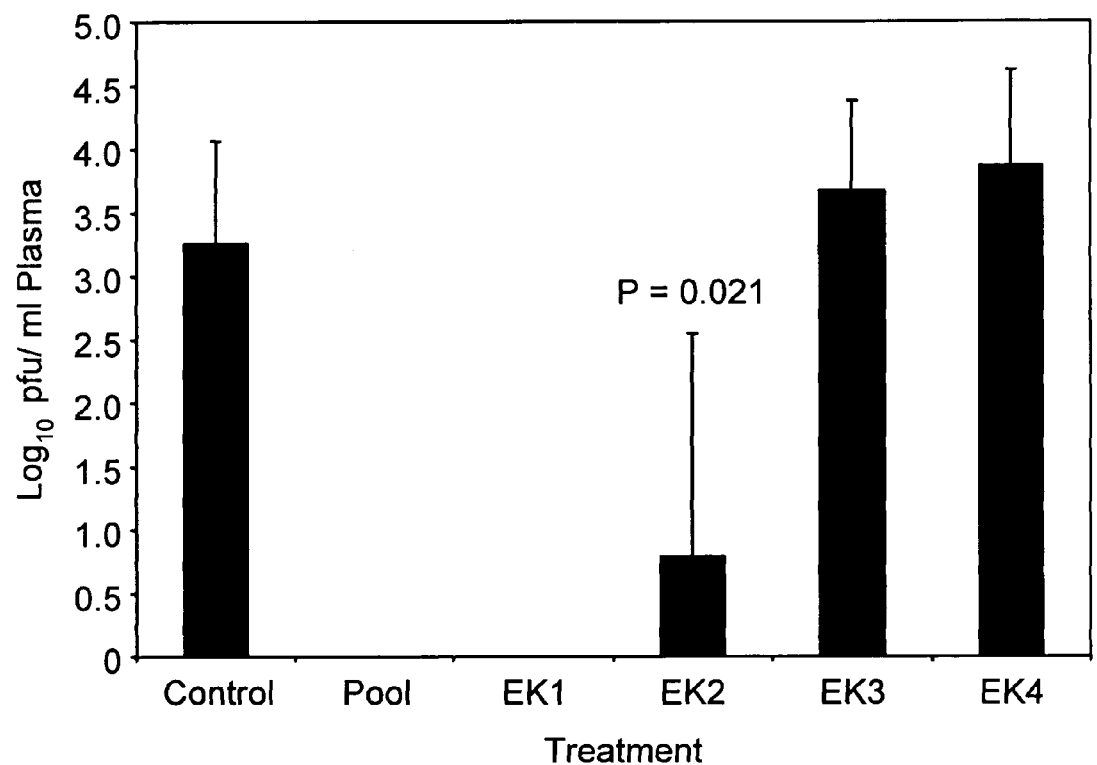
FIG. 7 illustrates data demonstrating that administration of 6 doses of SNALP encapsulating 0.75 mg/kg siRNA targeting Ebola L-pol inhibited Ebola viral replication in vivo.

SNALP Encapsulating siRNA Targeting Ebola L-pol Inhibit Ebola Virus Replication In Vivo Guinea pigs were challenged with 1,000 pfu of infectious Ebola-Zaire. One hour following viral challenge, SNALP (DLinDMA:PEG-cDMA:DSPC:Chol in the molar ratio 30:2:20:48) encapsulating either individual siRNA targeting Ebola-Zaire L-pol (i.e., EK1, EK2, EK3, or EK4) or a pool of siRNA targeting Ebola-Zaire L-pol (i.e., EK1, EK2, EK3, and EK4) were administered to the guinea pigs retroorbitally once a day for 6 days at a dose of 0.75 mg siRNA per kg. PBS or SNALP encapsulating scrambled siRNA sequences was administered to control animals. On day 7 following administration of SNALP, plasma viral load was measured. Guinea pigs that received SNALP encapsulating EK1 or the pool containing EK1, EK2, EK3, and EK4 exhibited no detectable viral load. Guinea pigs that received SNALP encapsulating EK2 exhibited a viral load 10 fold lower than that of control animals (P=0.021). The results are shown in FIG. 7.

Example 9

SNALP Encapsulating siRNA Targeting Ebola L-pol Protect from Ebola Challenge Mice were challenged with 1,000 pfu of infectious Ebola-Zaire. Following viral challenge, mice were administered intravenously through their tail vein one of the SNALP formulations shown in Table 16. Groups of 10 mice were administered: (1) SNALP encapsulating EK1 siRNA targeting Ebola-Zaire L-pol (SNALP 1, 3, 4, or 5 of Table 16); (2) PBS (virus only control); or (3) SNALP encapsulating a control β-galactosidase siRNA sequence (SNALP 2 of Table 16).

TABLE 16

Summary of the SNALP formulations used in this study.

| SNALP | siRNA | Lipid Composition | Nucleic Acid:Lipid Ratio (mg:mg) | Final siRNA Concentration (mg/ml) | SNALP Size[1] (nm) |
|---|---|---|---|---|---|
| 1 | EK1 | PEG-cDMA:DLinDMA:DSPC:Chol (2:30:20:48) | 1:12.8 (0.08) | 0.1 | 83 (0.15) |
| 2 | β-gal 478 | PEG-cDMA:DLinDMA:DSPC:Chol (2:30:20:48) | 1:12.8 (0.08) | 0.1 | 83 (0.15) |
| 3 | EK1 | PEG-cDMA:DLinDMA:DSPC:Chol (2:40:10:48) | 1:25 (0.04) | 0.1 | 83 (0.18) |
| 4 | EK1 | PEG-cDMA:DLinDMA:DSPC:Chol (2:40:10:48) | 1:25 (0.04) | 0.1 | 130 (0.14) |
| 5 | EK1 | PEG-cDMA:DLinDMA:DPPE (2:70:28) | 1:31 (0.03) | 0.1 | 119 (0.17) |

[1]The number in parentheses indicates the polydispersity value, which refers to an estimate of the width of the distribution of the particle size measurements.

Figure 8:
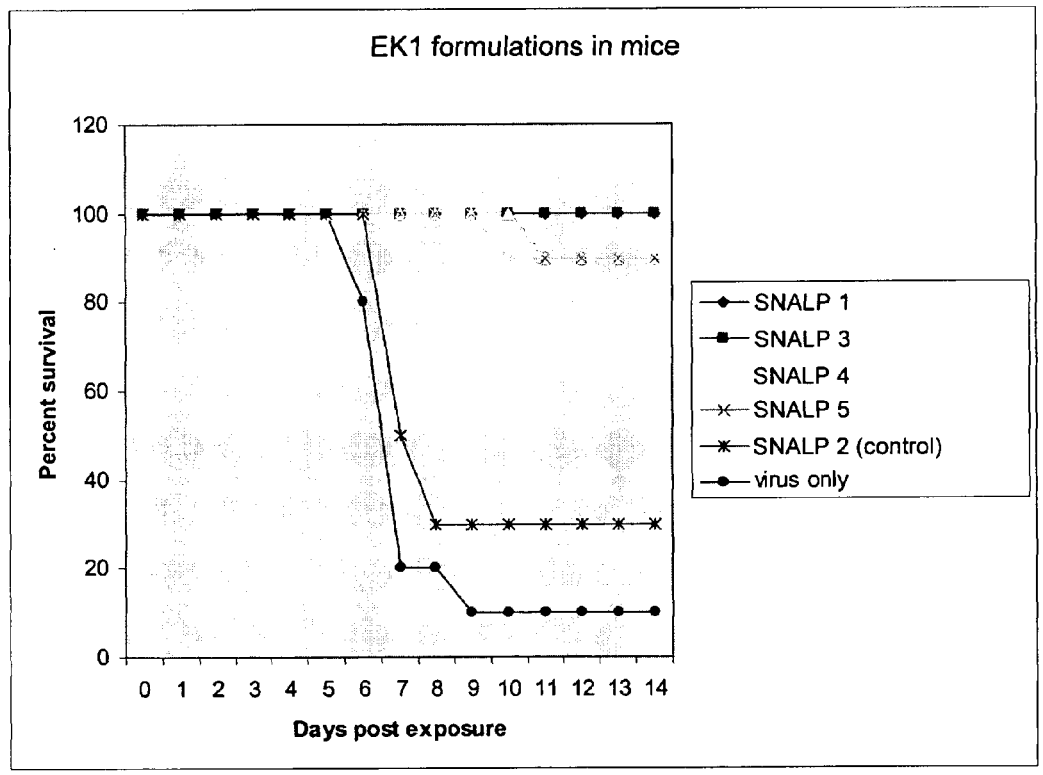
FIG. 8 illustrates data demonstrating that administration of SNALP encapsulating siRNA targeting Ebola L-pol protected mice challenged with a lethal dose of Ebola virus.

FIG. 8 shows that 100% of the mice that received SNALP 1 or 3 encapsulating EK1 siRNA survived the length of the 14 day study, 90% of the mice that received SNALP 4 or 5 encapsulating EK1 siRNA survived the length of the 14 day study, while only 10% of the control animals that received PBS and only 30% of the control animals that received β-galactosidase siRNA (SNALP 2) survived the length of the 14 day study.

Example 10

SNALP Encapsulating siRNA Targeting Ebola L-pol Have Immunostimulatory Effects

Figure 9:
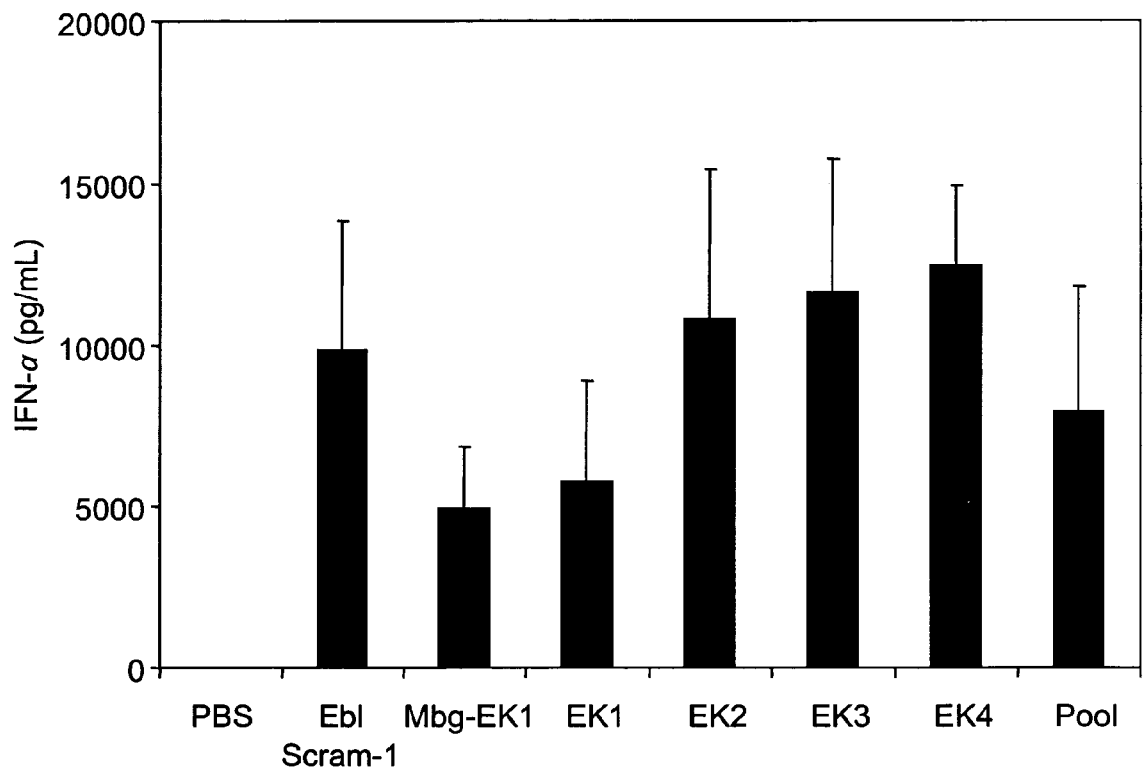
FIG. 9 illustrates data demonstrating that IFN-α was detected in the serum of mice following a single intravenous administration of SNALP encapsulating siRNA targeting Ebola L-pol or Marburg L-pol.
Figure 10:
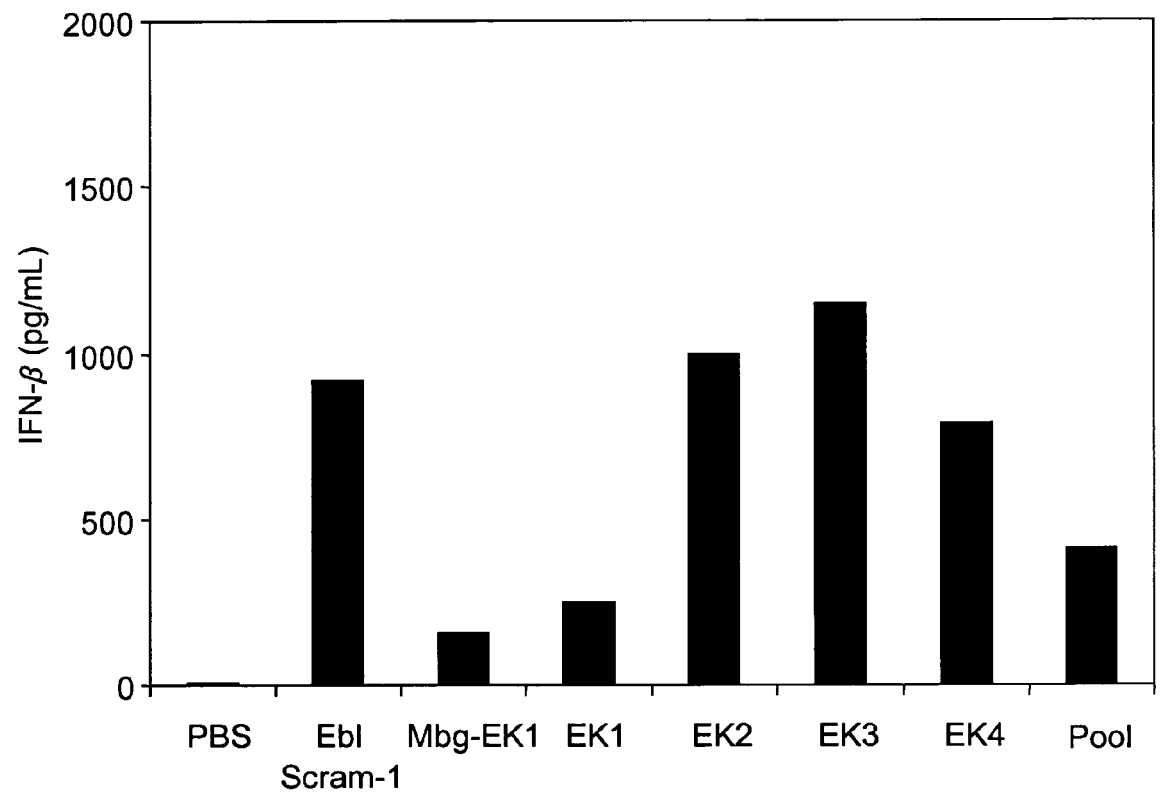
FIG. 10 illustrates data demonstrating that IFN-α was detected in the serum of mice following a single intravenous administration of SNALP encapsulating siRNA targeting Ebola L-pol or Marburg L-pol.

SNALP (DLinDMA:PEG-cDMA:DSPC:Chol in the molar ratio 30:2:20:48) encapsulating either individual siRNA targeting Ebola-Zaire L-pol (i.e., EK1, EK2, EK3, or EK4), a pool of siRNA targeting Ebola-Zaire L-pol (i.e., EK1, EK2, EK3, and EK4), or an siRNA targeting Marburg L-pol (i.e., Mbg-EK1) were administered to female Balb/C mice at 5 mg siRNA/kg. PBS or SNALP encapsulating scrambled siRNA sequences was administered to control animals. Plasma IFN-α and IFN-β were measured 6 hours after administration of the SNALP using methods described above. Mice produced IFN-α and IFN-β regardless of siRNA sequence. The results are shown in FIGS. 9 and 10.

It is to be understood that the above description is intended to be illustrative and not restrictive. Many embodiments will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications, patents, PCT publications, and Accession Nos. are incorporated herein by reference for all purposes.

LENGTHY TABLES

The patent contains a lengthy table section. A copy of the table is available in electronic form from the USPTO web site (http://seqdata.uspto.gov/?pageRequest=docDetail&DocID=US07838658B2). An electronic copy of the table will also be available from the USPTO upon request and payment of the fee set forth in 37 CFR 1.19(b)(3).

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US07838658B2). An electronic copy of the "Sequence Listing" will also be available from the USPTO upon request and payment of the fee set forth in 37 CFR 1.19(b)(3).

What is claimed is:

1. An siRNA molecule for silencing Ebola virus L-polymerase (L-pol) expression comprising a double-stranded sequence consisting of SEQ ID NO:23 and SEQ ID NO:24.

2. The siRNA molecule in accordance with claim 1, wherein said double-stranded sequence comprises a hairpin loop structure.

3. A pharmaceutical composition comprising an siRNA molecule in accordance with claim 1 and a phamaceutically acceptable carrier.

4. A nucleic acid-lipid particle comprising: an siRNA molecule in accordance with claim 1; a cationic lipid; and a non-cationic lipid.

5. The nucleic acid-lipid particle in accordance with claim 4, wherein said cationic lipid is a member selected from the group consisting of N,N-dioleyl-N,N-dimethylammonium chloride (DODAC), N,N-distearyl-N,N-dimethylammonium bromide (DDAB), N-(1-(2,3-dioleoyloxy)propyl)-N,N,N-trimethylammonium chloride (DOTAP), N-(1-(2,3-dioleyloxy)propyl)-N,N,N-trimethylammonium chloride (DOTMA), N,N-dimethyl-2,3-dioleyloxypropylamine (DODMA), 1,2-DiLinoleyloxy-N,N-dimethylaminopropane (DLinDMA), 1,2-Dilinolenyloxy-N,N-dimethylaminopropane (DLendMA), and a mixture thereof.

6. The nucleic acid-lipid particle in accordance with claim 4, wherein said cationic lipid is DLinDMA.

7. The nucleic acid-lipid particle in accordance with claim 4, wherein said non-cationic lipid is an anionic lipid.

8. The nucleic acid-lipid particle in accordance with claim 4, wherein said non-cationic lipid is a neutral lipid.

9. The nucleic acid-lipid particle in accordance with claim 4, wherein said non-cationic lipid is a member selected from the group consisting of distearoylphosphatidylcholine (DSPC), dioleoylphosphatidylethanolamine (DOPE), palmitoyloleoyl-phosphatidylcholine (POPC), palmitoyloleoyl-phosphatidylethanolamine (POPE), palmitoyloleyol-phosphatidylglycerol (POPG), dipalmitoyl-phosphatidylethanolamine (DPPE), dimyristoyl-phosphatidylethanolamine (DMPE), distearoyl-phosphatidylethanolamine (DSPE), monomethyl-phosphatidylethanolamine, dimethyl-phosphatidylethanolamine, dielaidoyl-phosphatidylethanolamine (DEPE), stearoyloleoyl-phosphatidylethanolamine (SOPE), egg phosphatidylcholine (EPC), cholesterol, and a mixture thereof.

10. The nucleic acid-lipid particle in accordance with claim 4, wherein said non-cationic lipid is DSPC.

11. The nucleic acid-lipid particle in accordance with claim 4, further comprising a conjugated lipid that inhibits aggregation of particles.

12. The nucleic acid-lipid particle in accordance with claim 11, wherein said conjugated lipid that inhibits aggregation of particles is a member selected from the group consisting of a polyethyleneglycol (PEG)-lipid conjugate, a polyamide (ATTA)-lipid conjugate, and a mixture thereof.

13. The nucleic acid-lipid particle in accordance with claim 12, wherein said PEG-lipid is a member selected from the group consisting of a PEG-diacylglycerol, a PEG dialkyloxypropyl, a PEG-phospholipid, a PEG-ceramide, and a mixture thereof.

14. The nucleic acid-lipid particle in accordance with claim 12, wherein said conjugated lipid that inhibits aggregation of particles comprises a polyethyleneglycol (PEG)-dialkyloxypropyl (PEG-DAA) conjugate.

15. The nucleic acid-lipid particle in accordance with claim 14, wherein said PEG-DAA conjugate is a member selected from the group consisting of a PEG-dilauryloxypropyl ($C_{12}$), a PEG-dimyristyloxypropyl ($C_{14}$), a PEG-dipalmityloxypropyl ($C_{16}$), and a PEG-distearyloxypropyl ($C_{18}$).

16. The nucleic acid-lipid particle in accordance with claim 14, wherein said PEG-DAA conjugate is a PEG-dimyristyloxypropyl ($C_{14}$).

17. The nucleic acid-lipid particle in accordance with claim 4, wherein said cationic lipid comprises from about 20 mol % to about 50 mol % of the total lipid present in said particle.

18. The nucleic acid-lipid particle in accordance with claim 4, wherein said cationic lipid comprises about 40 mol % of the total lipid present in said particle.

19. The nucleic acid-lipid particle in accordance with claim 4, wherein said non-cationic lipid comprises from about 5 mol % to about 90 mol % of the total lipid present in said particle.

20. The nucleic acid-lipid particle in accordance with claim 4, wherein said non-cationic lipid comprises about 20 mol % of the total lipid present in said particle.

21. The nucleic acid-lipid particle in accordance with claim 14, wherein said PEG-DAA conjugate comprises from 0 mol % to about 20 mol % of the total lipid present in said particle.

22. The nucleic acid-lipid particle in accordance with claim 14, wherein said PEG-DAA conjugate comprises about 2 mol % of the total lipid present in said particle.

23. The nucleic acid-lipid particle in accordance with claim 4, further comprising cholesterol.

24. The nucleic acid-lipid particle in accordance with claim 23, wherein the cholesterol comprises from about 10 mol % to about 60 mol % of the total lipid present in said particle.

25. The nucleic acid-lipid particle in accordance with claim 23, wherein the cholesterol comprises about 48 mol % of the total lipid present in said particle.

26. The nucleic acid-lipid particle in accordance with claim 4, wherein said siRNA molecule in said nucleic acid-lipid particle is not substantially degraded after exposure of said particle to a nuclease at 37° C. for 20 minutes.

27. The nucleic acid-lipid particle in accordance with claim 4, wherein said siRNA molecule in said nucleic acid-lipid particle is not substantially degraded after incubation of said particle in serum at 37° C. for 30 minutes.

28. The nucleic acid-lipid particle in accordance with claim 4, wherein said siRNA molecule is fully encapsulated in said nucleic acid-lipid particle.

29. The nucleic acid-lipid particle in accordance with claim 4, wherein said particle has a siRNA:lipid ratio of from about 0.01 to about 0.2.

30. The nucleic acid-lipid particle in accordance with claim 4, wherein said particle has a siRNA:lipid ratio of from about 0.02 to about 0.1.

31. The nucleic acid-lipid particle in accordance with claim 4, wherein said particle has a siRNA:lipid ratio of about 0.04.

32. The nucleic acid-lipid particle in accordance with claim 4, wherein said particle has a median diameter of from about 50 nm to about 150 nm.

33. The nucleic acid-lipid particle in accordance with claim 4, wherein said particle has a median diameter of from about 70 nm to about 90 nm.

34. A pharmaceutical composition comprising a nucleic acid-lipid particle in accordance with claim 4 and a pharmaceutically acceptable carrier.

35. The nucleic acid-lipid particle in accordance with claim 4, wherein said non-cationic lipid comprises DSPC and cholesterol.

36. The nucleic acid-lipid particle in accordance with claim 10, wherein said DSPC comprises about 10 mol % of the total lipid present in said particle.

37. The nucleic acid-lipid particle in accordance with claim 4, wherein said cationic lipid comprises from about 2 mol % to about 60 mol % of the total lipid present in said particle.

38. The nucleic acid-lipid particle in accordance with claim 4, wherein said non-cationic lipid comprises dipalmitoylphosphatidylcholine (DPPC).

39. The nucleic acid-lipid particle in accordance with claim 4, wherein said non-cationic lipid comprises DPPC and cholesterol.

40. The siRNA molecule in accordance with claim 1, wherein said siRNA molecule comprises 3' overhangs of about 1 to about 4 nucleotides on one or both sides of the double-stranded sequence.

41. The siRNA molecule in accordance with claim 1, wherein said siRNA molecule comprises at least one modified nucleotide.

42. The siRNA molecule in accordance with claim 1, wherein said siRNA molecule comprises at least one modified nucleotide in one or both strands of the double-stranded sequence.

43. The siRNA molecule in accordance with claim 1, wherein said siRNA molecule comprises at least one 2'-O-methyl (2'OMe) nucleotide.

44. The siRNA molecule in accordance with claim 1, wherein said siRNA molecule comprises at least one 2'OMe nucleotide selected from the group consisting of a 2'OMe-guanosine nucleotide, 2'OMe-uridine nucleotide, 2'OMe-adenosine nucleotide, 2'OMe-cytosine nucleotide, and mixtures thereof.

45. The nucleic acid-lipid particle in accordance with claim 11, wherein said conjugated lipid that inhibits aggregation of particles comprises from about 0.5 mol % to about 20 mol % of the total lipid present in said particle.

* * * * *